(12) United States Patent
Yokoyama et al.

(10) Patent No.: US 11,618,730 B2
(45) Date of Patent: Apr. 4, 2023

(54) ORGANIC LIGHT-EMITTING ELEMENT, AND LIGHT-EMITTING MATERIAL AND COMPOUND FOR USE THEREIN

(71) Applicant: TOYOBO CO., LTD., Osaka (JP)

(72) Inventors: Masayuki Yokoyama, Shiga (JP); Kazutake Hagiya, Shiga (JP); Chihaya Adachi, Fukuoka (JP)

(73) Assignee: TOYOBO CO., LTD., Osaka (JP)

( * ) Notice: Subject to any disclaimer, the term of this patent is extended or adjusted under 35 U.S.C. 154(b) by 975 days.

(21) Appl. No.: 16/331,374

(22) PCT Filed: Sep. 8, 2017

(86) PCT No.: PCT/JP2017/032510
§ 371 (c)(1),
(2) Date: Mar. 7, 2019

(87) PCT Pub. No.: WO2018/047948
PCT Pub. Date: Mar. 15, 2018

(65) Prior Publication Data
US 2019/0194131 A1    Jun. 27, 2019

(30) Foreign Application Priority Data
Sep. 9, 2016 (JP) .............................. JP2016-176280

(51) Int. Cl.
*C07D 209/86* (2006.01)
*C07D 401/14* (2006.01)
(Continued)

(52) U.S. Cl.
CPC .......... *C07D 209/86* (2013.01); *C07C 13/567* (2013.01); *C07D 401/14* (2013.01);
(Continued)

(58) Field of Classification Search
None
See application file for complete search history.

(56) References Cited

U.S. PATENT DOCUMENTS

2014/0001451 A1    1/2014  Mizuki et al.
2014/0336379 A1   11/2014  Adachi et al.
(Continued)

FOREIGN PATENT DOCUMENTS

CN    103959502    7/2014
CN    104204132   12/2014
(Continued)

OTHER PUBLICATIONS

Notification of Reason for Refusal dated Oct. 4, 2021 in corresponding Korean Patent Application No. 10-20197009832, with English Machine Translation.
(Continued)

*Primary Examiner* — Jay Yang
(74) *Attorney, Agent, or Firm* — Wenderoth, Lind & Ponack, L.L.P.

(57) ABSTRACT

Using a compound that contains a structure where a carbazol-9-yl group substituted with a perfluoroalkyl group at the 2-position and the 7-position and a structural unit having a positive Hammett constant $\sigma_p$ (but excluding an aromatic hydrocarbon group) bond to each other directly or via a π-conjugated linking group, wherein at least a part of the carbazol-9-yl group and at least a part of the structural unit having a positive Hammett constant $\sigma_p$ and, if any, the π-conjugated linking group form a π-electron conjugated system, an organic light emitting device having a high emission efficiency can be provided.

14 Claims, 7 Drawing Sheets

(51) Int. Cl.
*C07D 403/10* (2006.01)
*C07D 413/14* (2006.01)
*C07D 417/14* (2006.01)
*C07D 495/22* (2006.01)
*H01L 51/50* (2006.01)
*C07D 403/14* (2006.01)
*C07D 487/16* (2006.01)
*C07C 13/567* (2006.01)
*C07D 487/04* (2006.01)
*C07D 471/06* (2006.01)
*C09K 11/06* (2006.01)
*C07F 9/572* (2006.01)
*H01L 51/00* (2006.01)

(52) U.S. Cl.
CPC ......... *C07D 403/10* (2013.01); *C07D 403/14* (2013.01); *C07D 413/14* (2013.01); *C07D 417/14* (2013.01); *C07D 471/06* (2013.01); *C07D 487/04* (2013.01); *C07D 487/16* (2013.01); *C07D 495/22* (2013.01); *C07F 9/572* (2013.01); *C09K 11/06* (2013.01); *H01L 51/50* (2013.01); *H01L 51/5012* (2013.01); *H01L 51/006* (2013.01); *H01L 51/007* (2013.01); *H01L 51/0058* (2013.01); *H01L 51/0067* (2013.01); *H01L 51/0072* (2013.01); *H01L 51/0074* (2013.01)

(56) References Cited

U.S. PATENT DOCUMENTS

| | | | |
|---|---|---|---|
| 2015/0105564 | A1 | 4/2015 | Adachi et al. |
| 2018/0062085 | A1 | 3/2018 | Bergmann et al. |
| 2018/0062086 | A1 | 3/2018 | Fabio et al. |
| 2019/0194130 | A1 | 6/2019 | Bergmann et al. |
| 2019/0194171 | A1* | 6/2019 | Bergmann .......... H01L 51/0072 |
| 2019/0198778 | A1 | 6/2019 | Bergmann et al. |
| 2019/0248741 | A1 | 8/2019 | Zink |
| 2021/0184134 | A1 | 6/2021 | Seifermann et al. |

FOREIGN PATENT DOCUMENTS

| | | |
|---|---|---|
| CN | 107778214 | 3/2018 |
| CN | 107778294 | 3/2018 |
| CN | 109071501 | 12/2018 |
| CN | 109415316 | 3/2019 |
| CN | 109415317 | 3/2019 |
| CN | 109641880 | 4/2019 |
| CN | 109661390 | 4/2019 |
| CN | 109996795 | 7/2019 |
| DE | 10 2016 108 335 | 12/2016 |
| DE | 10 2016 120 373 | 8/2017 |
| EP | 2 787 549 | 10/2014 |
| EP | 2 851 408 | 3/2015 |
| JP | 2003-335754 | 11/2003 |
| JP | 2004-288380 | 10/2004 |
| JP | 2008-85079 | 4/2008 |
| JP | 5366106 | 12/2013 |
| JP | 2015-172166 | 10/2015 |
| JP | 2016-17078 | 2/2016 |
| JP | 2017-103440 | 6/2017 |
| JP | 2018-70586 | 5/2018 |
| KR | 10-2015-0005583 | 1/2015 |
| WO | 2013/081088 | 6/2013 |
| WO | 2013/154064 | 10/2013 |
| WO | 2013/175789 | 11/2013 |
| WO | 2015/022987 | 2/2015 |
| WO | 2015/137136 | 9/2015 |
| WO | 2015/180524 | 12/2015 |
| WO | 2016/181846 | 11/2016 |
| WO | 2018/008673 | 1/2018 |
| WO | WO-2018/041933 A1 * | 3/2018 |

OTHER PUBLICATIONS

Extended European Search Report dated Apr. 21, 2020 in corresponding European Patent Application No. 17848886.2.
Office Action dated Jun. 22, 2021 in corresponding Japanese Patent Application No. 2018-538490, with English translation.
International Search Report dated Nov. 21, 2017 in International (PCT) Application No. PCT/JP2017/032510.
International Preliminary Report on Patentability dated Mar. 12, 2019 in International Application No. PCT/JP2017/032510, with English translation.
Gantenbein et al., "New 4,4'-Bis(9-carbazolyl)-Biphenyl Derivatives with Locked Carbazole-Biphenyl Junctions: High-Triplet State Energy Materials", Chem. Mater., vol. 27, No. 7, 2015, pp. 1772-1779.
Mei et al., "The inductive-effect of electron withdrawing trifluoromethyl for thermally activated delayed fluorescence: tunable emission from tetra- to penta-carbazole in solution processed blue OLEDs", Chem. Commun., vol. 51, 2015, pp. 13024-13027.
Office Action dated Feb. 3, 2021 in corresponding Taiwanese Patent Application No. 106130885, with English Translation.
Office Action dated Jan. 29, 2022 in corresponding Chinese Patent Application No. 201780055482.2, with English-language translation.
Office Action dated Jun. 29, 2022 in corresponding Chinese Patent Application No. 201780055482.2, with English translation.
The Decision of Rejection dated Oct. 14, 2022 in corresponding Chinese Patent Application No. 201780055482.2, with English language translation.

* cited by examiner

[Fig. 1]
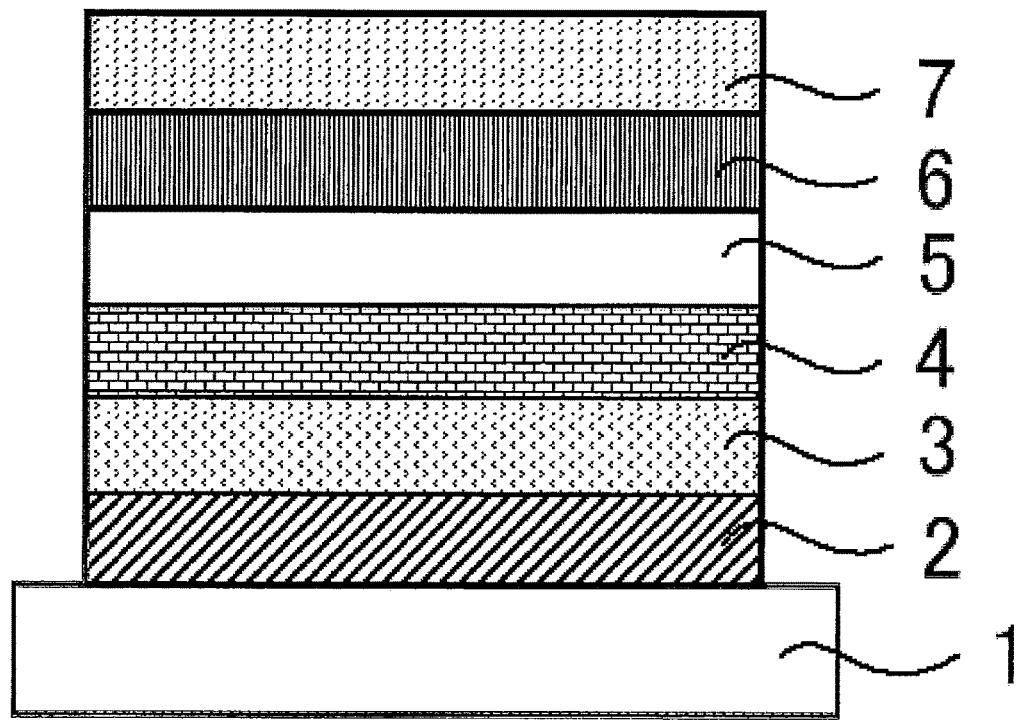

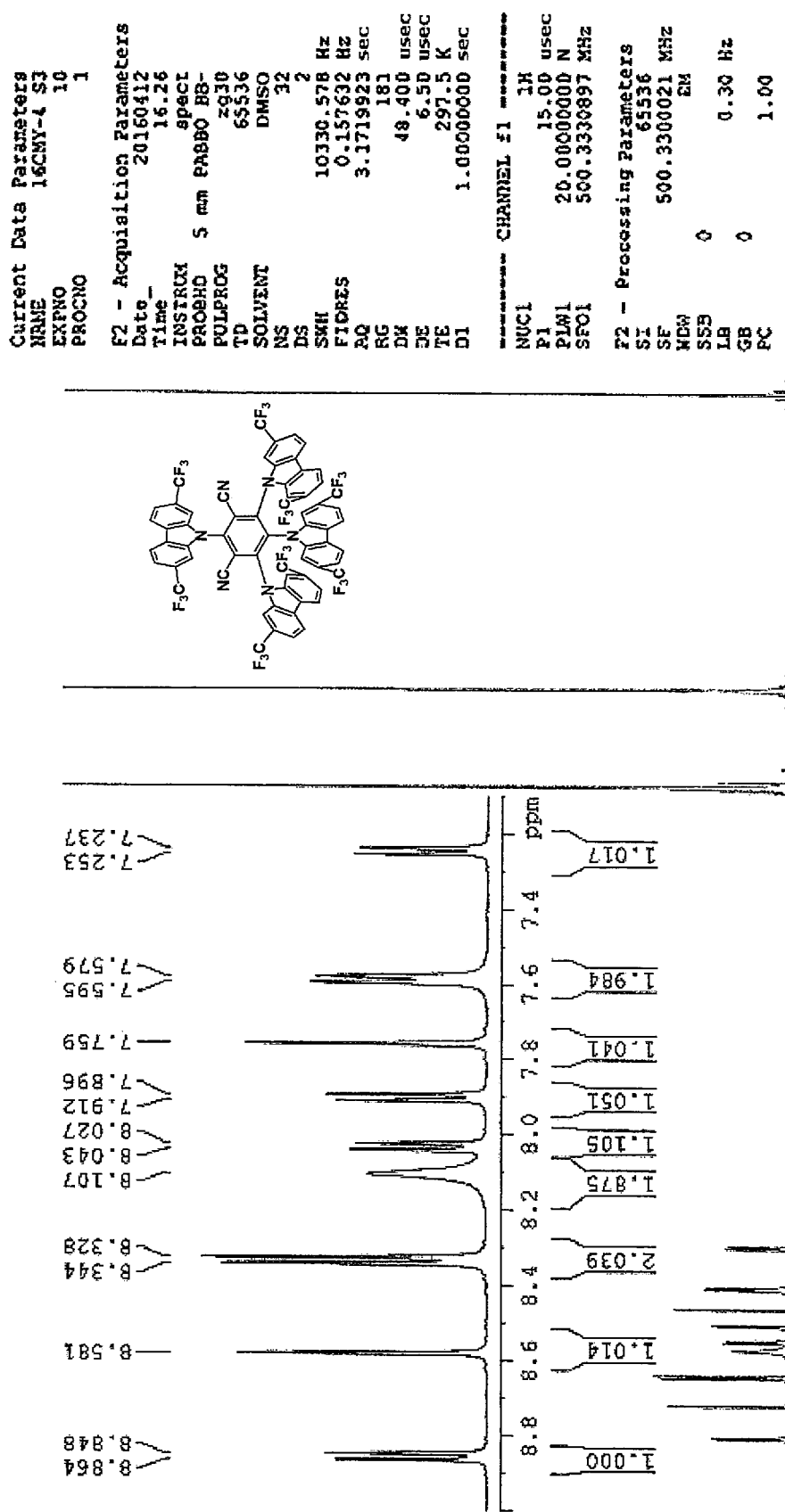
[Fig. 2]

[Fig. 3]
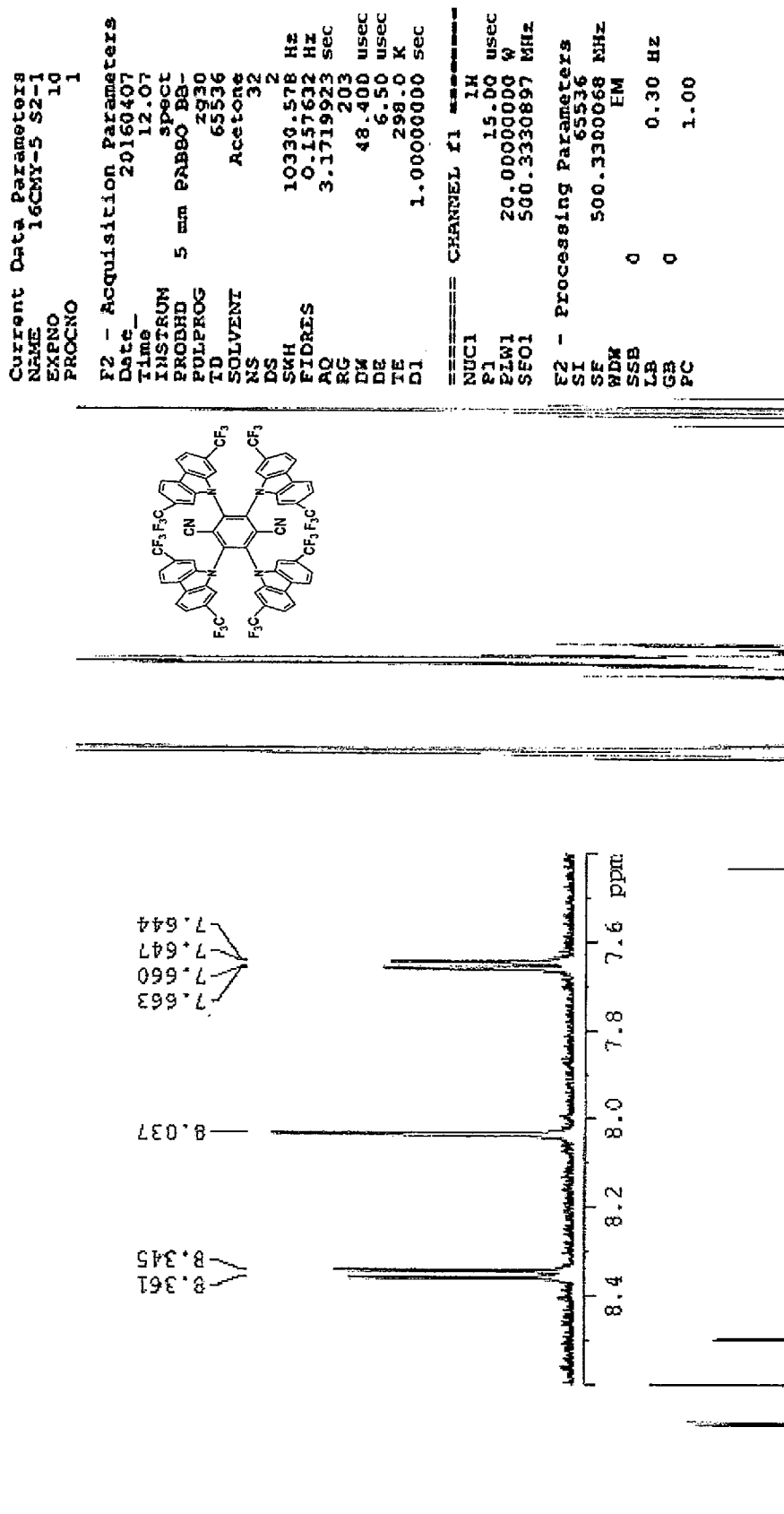

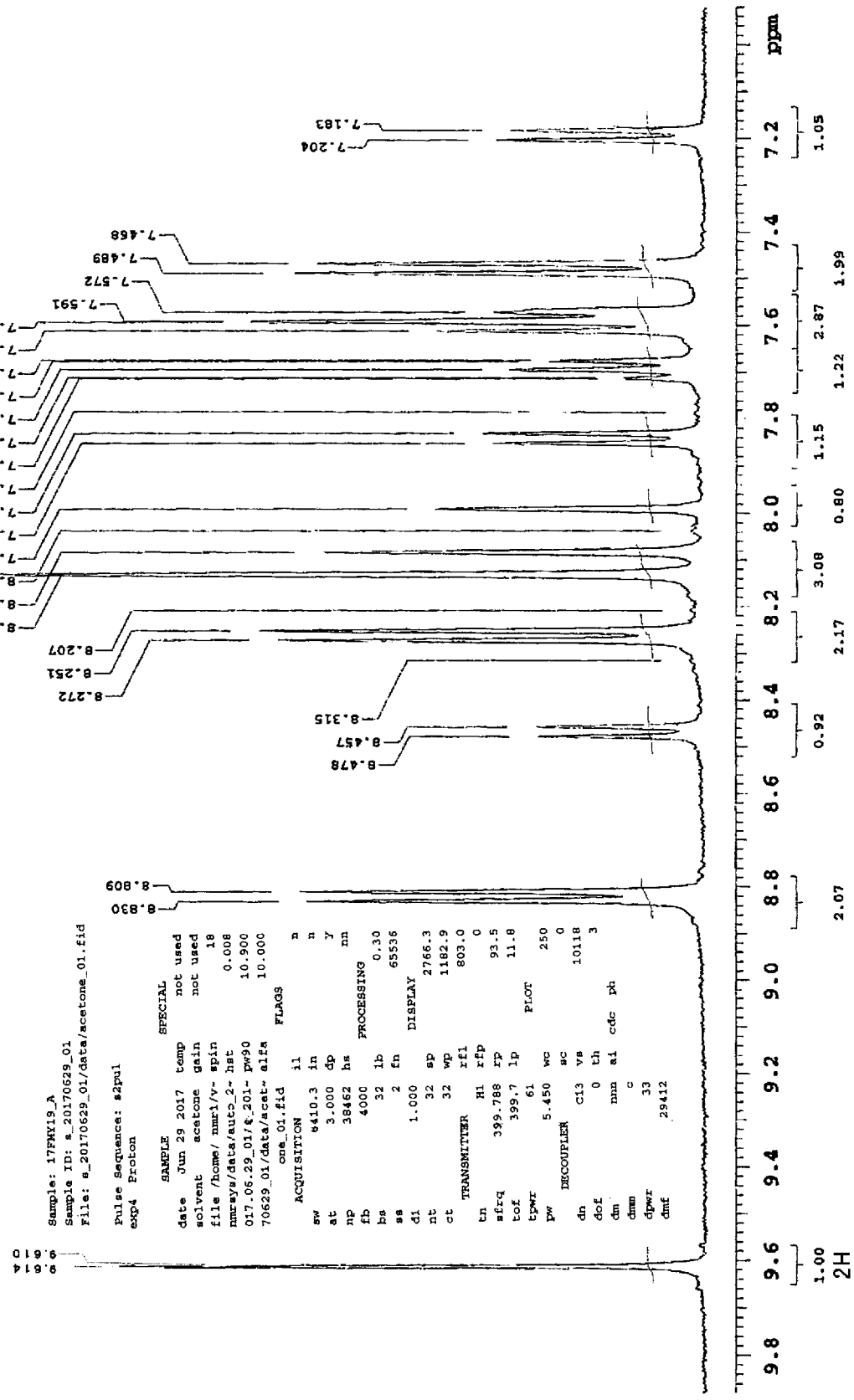
[Fig. 4]

[Fig. 5]
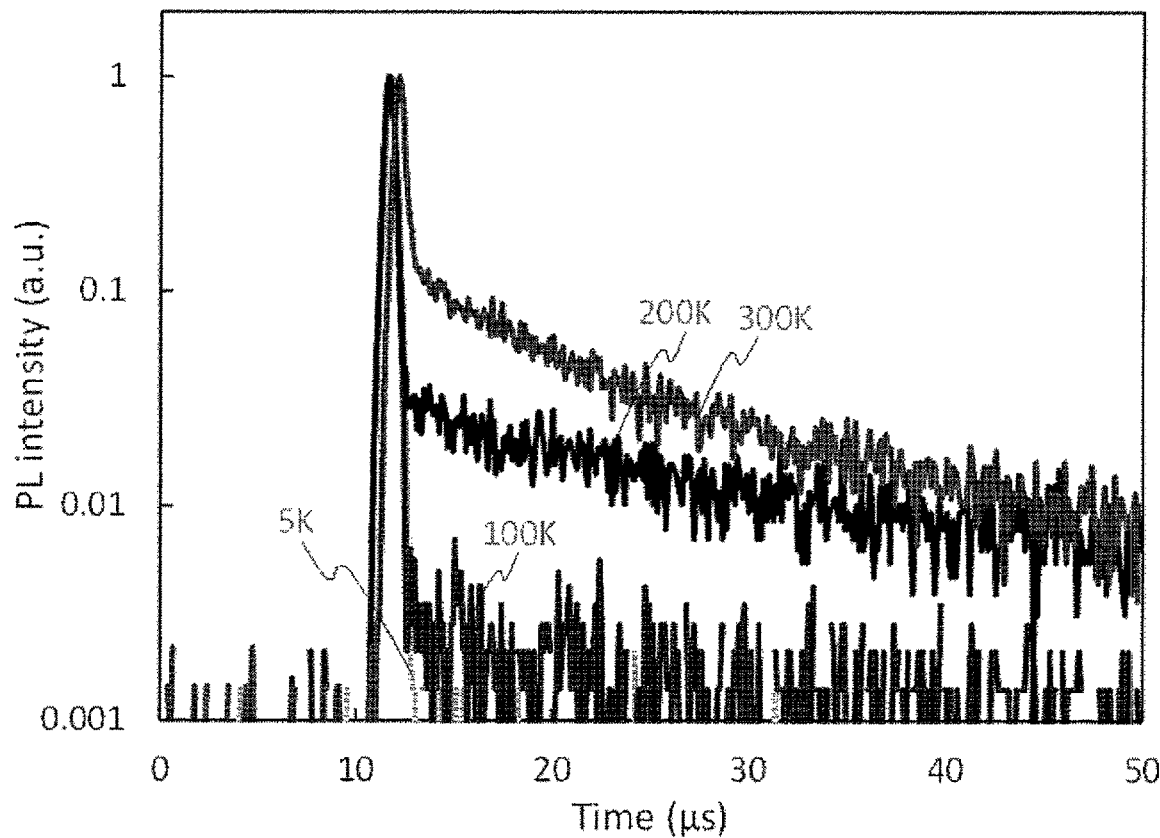
[Fig. 6]
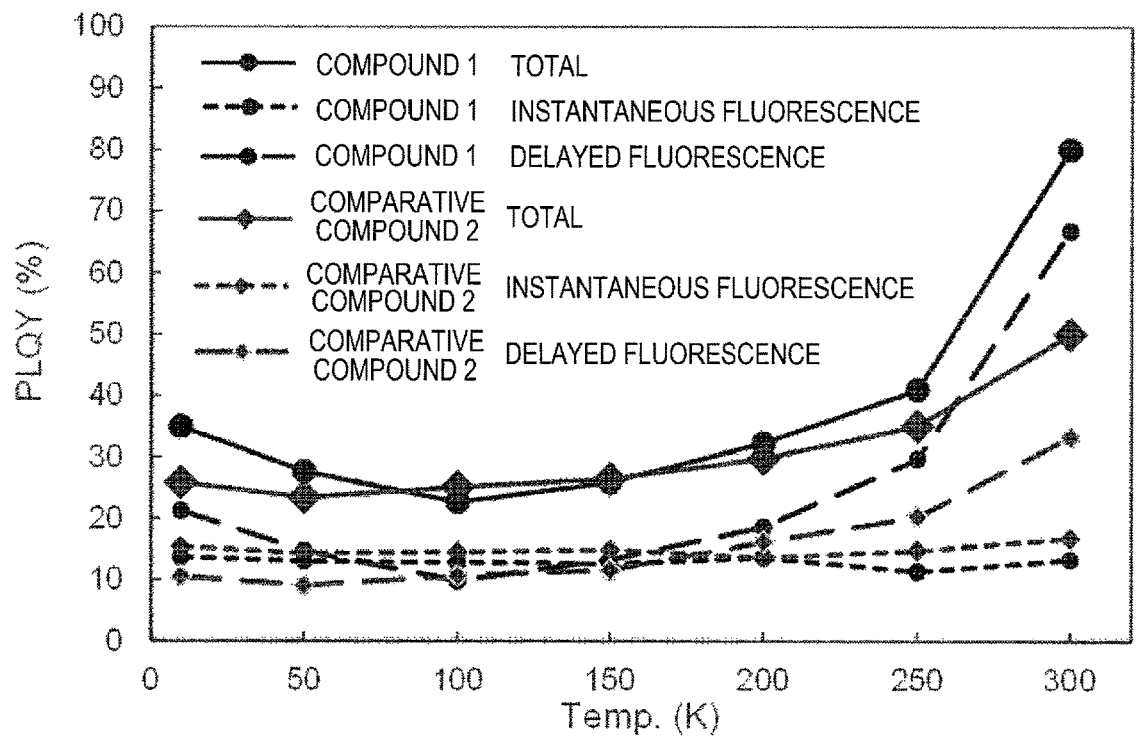

[Fig. 7]
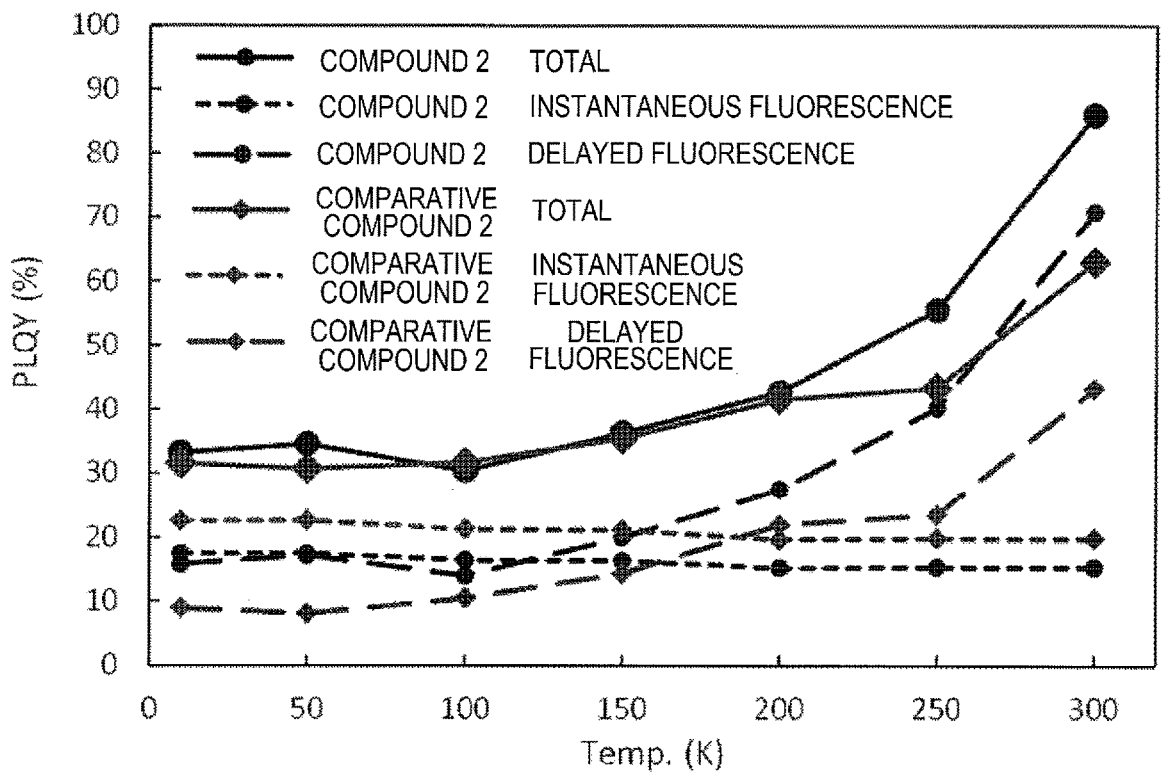
[Fig. 8]
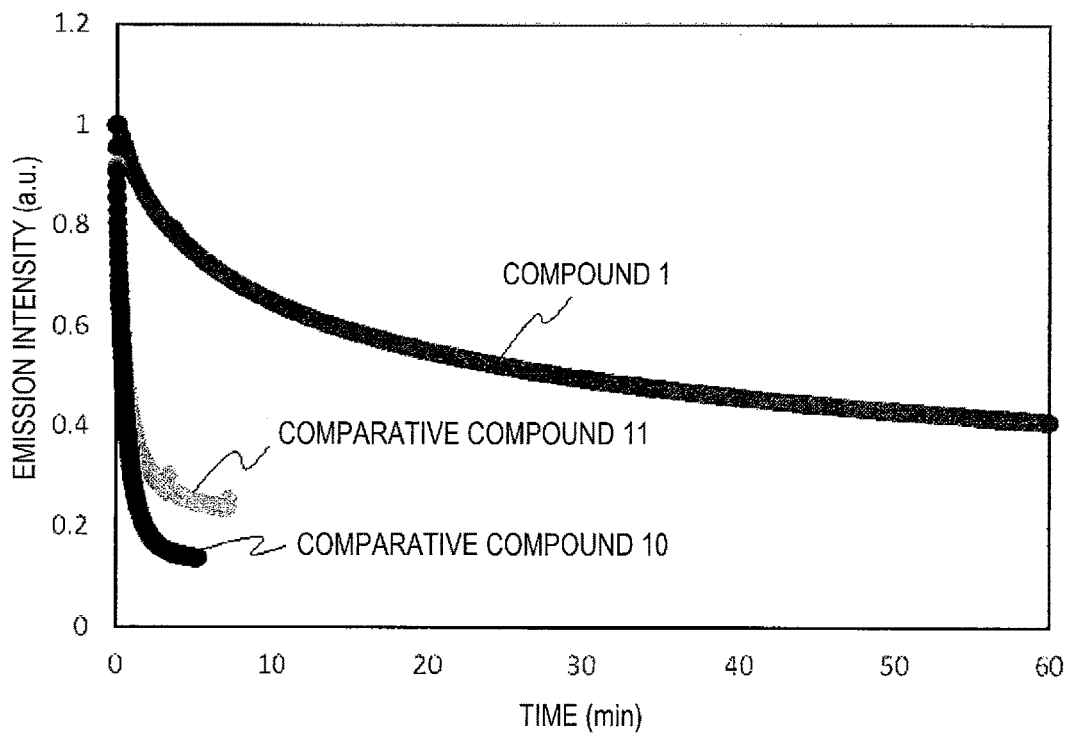

[Fig. 9]
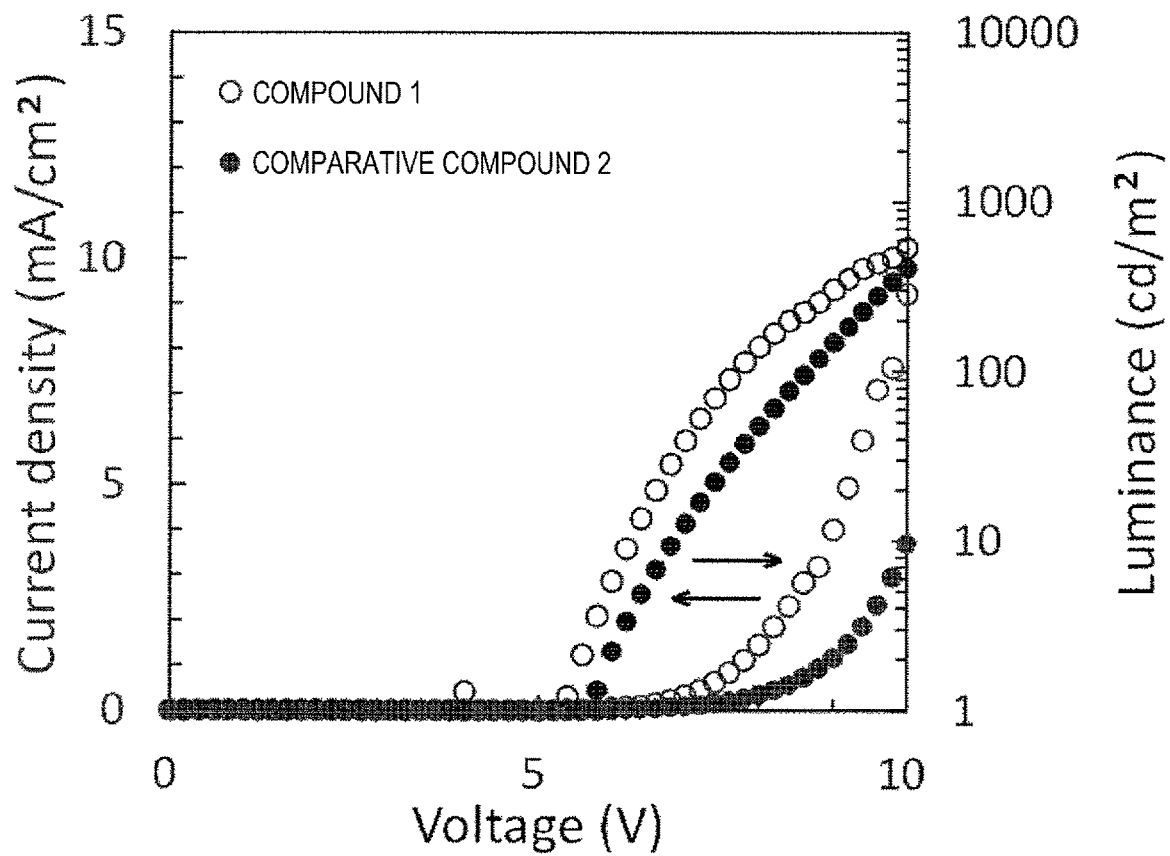
[Fig. 10]
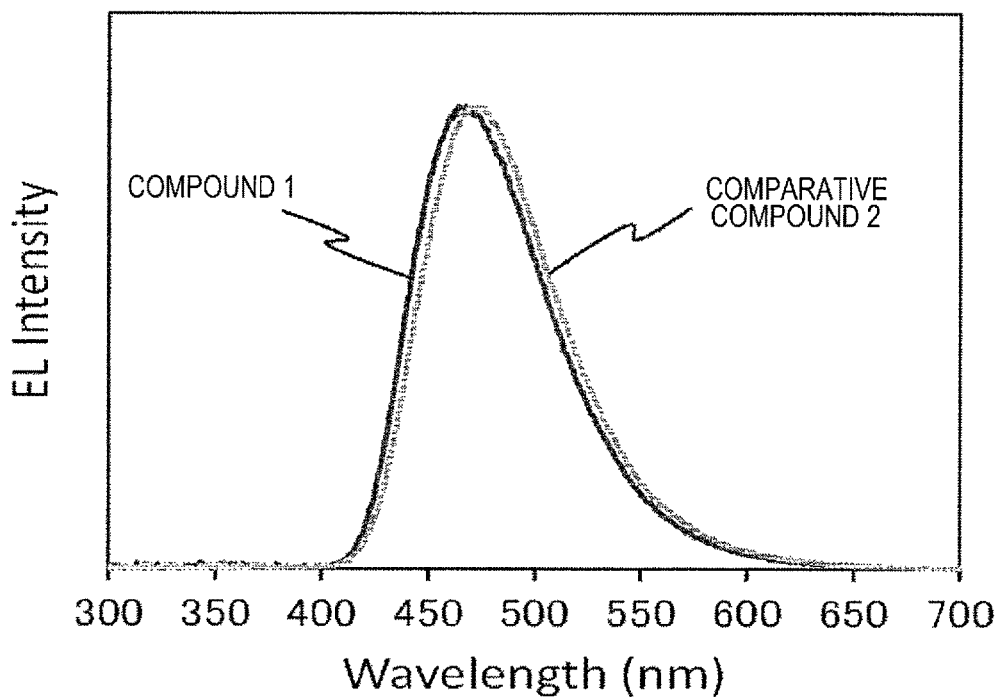

ORGANIC LIGHT-EMITTING ELEMENT, AND LIGHT-EMITTING MATERIAL AND COMPOUND FOR USE THEREIN

TECHNICAL FIELD

The present invention relates to a high-efficiency organic light emitting device. The invention also relates to a light emitting material and a compound for use for the organic light emitting device.

BACKGROUND ART

Studies for enhancing the emission efficiency of organic light emitting devices such as organic electroluminescent devices (organic EL devices) are being made actively. In particular, various contrivances are being made for increasing emission efficiency of organic light emitting devices by newly developing and combining an electron transport material, a hole transport material and a light emitting material that constitute an organic electroluminescent device. Among them, there are seen studies relating to an organic electroluminescent device that utilizes a compound having a carbazolyl group substituted with a perfluoroalkyl group.

For example, NPL 1 describes usability of 3,5,3',5'-tetramethyl-4,4'-bis[(2,7-ditrifluoromethyl)carbazol-9-yl]biphenyl as a matrix material for organic electroluminescent devices.

PTL 1 describes use of a cyanobenzene derivative represented by the following formula (3) as a light emitting material for organic light emitting devices. This defines that, in the formula (3), one of $R^{81}$ to $R^{85}$ is a cyano group, two of $R^{81}$ to $R^{85}$ each are a 9-carbazolyl group optionally substituted with a specific substituent, and the other two are hydrogen atoms. The literature lists a halogen atom and an alkyl group in the substituent group with which the 9-carbazolyl group may be substituted, and substituents composed of a combination of the substituents listed in that substituent group.

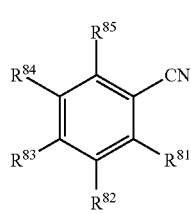

Formula (3)

PTL 2 describes the following compound F-9 as a fluorescent light emitting dopant. The literature also describes use of a host compound represented by the following formula (I) in a light emitting layer of an organic electroluminescent device. This defines that $X_{101}$ represents $NR_{101}$, an oxygen atom, a sulfur atom, $CR_{102}R_{103}$ or $SiR_{102}R_{103}$, $y_1$ to $y_8$ each represent $CR_{104}$ or a nitrogen atom, $R_{101}$ to $R_{104}$ each represent a hydrogen atom or a substituent, and $Ar_{101}$ and $Ar_{102}$ each represent an aromatic ring. The literature lists an aromatic hydrocarbon ring group, a fluoromethyl group and a cyano group in the substituent group represented by $R_{101}$ to $R_{104}$, further saying that the substituent may be further substituted with any of the substituents in the substituent group.

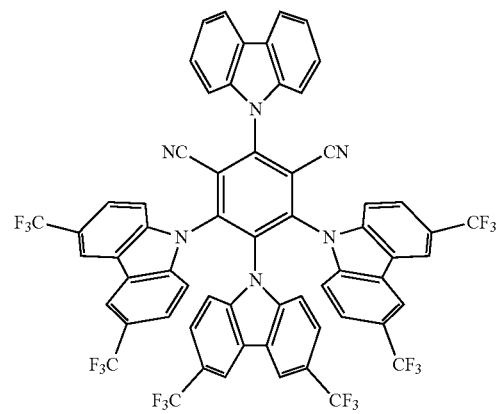

F-9

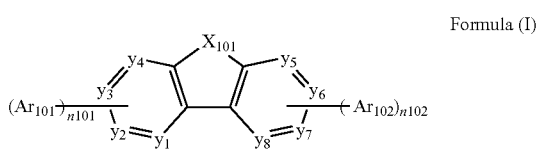

Formula (I)

NPL 2 describes $4CzCF_3Ph$ and $5CzCF_3Ph$, each of which is a material of a combination of trifluoromethylbenzene and carbazolyl groups.

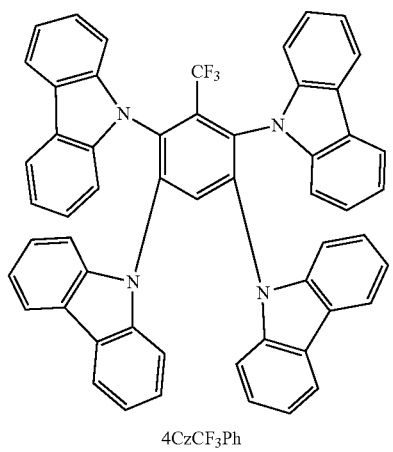

4CzCF$_3$Ph

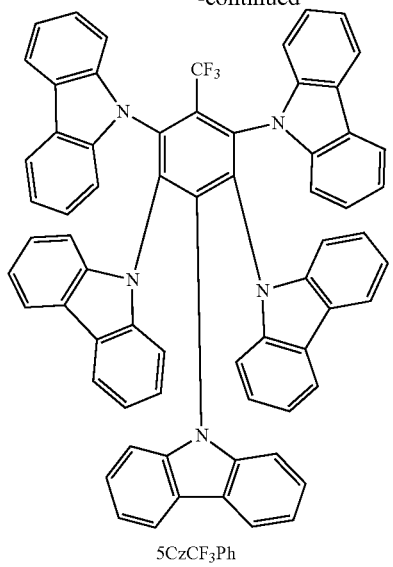

5CzCF$_3$Ph

PTL 3 describes use of a donor acceptor-type material represented by the formula (1) as a light emitting material for organic light emitting devices. As one example, the formula (206) is shown. $Z^1$ and $Z^2$ each represent a hydrogen atom, a cyano group, an optionally substituted aryl group, or an optionally substituted heteroaryl group.

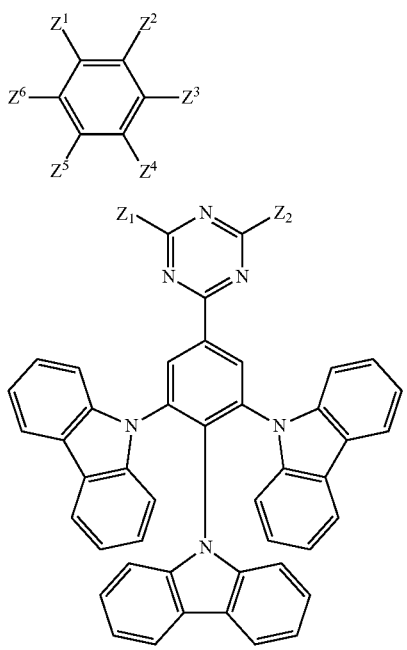

Formula (206)

CITATION LIST

Non-Patent Literature

NPL 1: Chem. Mater. 2015, 27, 1772-1779
NPL 2: Chem. Commun. 2015, 51, 13024-13027

Patent Literature

PTL 1: Japanese Patent 5366106
PTL 2: WO2015/022987
PTL 3: WO2016/181846

SUMMARY OF INVENTION

Technical Problem

As described above, each literature describes a formula including a compound having a carbazolyl group substituted with a perfluoroalkyl group, or a compound having such a structure. However, the present inventors have evaluated the emission characteristics of the compounds described in each literature and have known that the emission characteristics thereof could not be said to be always satisfactory.

First, regarding 3,5,3',5'-tetramethyl-4,4'-bis[(2,7-ditrifluoromethyl)carbazol-9-yl]biphenyl described in NPL 1, use thereof as a matrix material for organic electroluminescent devices is assumed, and the literature does not describe at all the emission characteristics of the compound. In addition, the compound does not have an acceptor-like group in the molecule and therefore could not effectively separate HOMO (highest occupied molecular orbital) and LUMO (lowest unoccupied molecular orbital) from each other, and consequently a high emission efficiency to be given by separation of HOMO and LUMO from each other could not be expected.

Regarding the compound F-9 in PTL 2, the present inventors have actually produced an organic electroluminescent device containing the compound in the light emitting layer therein and have evaluated the emission characteristics of the device, and have known that a sufficient emission efficiency could not be realized. The compound represented by the formula (I) in PTL 2 is used as a host compound, and the literature shows no investigations relating to the emission characteristics of the compound. Moreover, the formula (I) includes a very broad range of compounds, and the range includes a compound having a carbazolyl group substituted with a perfluoroalkyl group, but the compound having a carbazolyl group substituted with a perfluoromethyl group is not in the specific examples of the compound represented by the formula (I) listed in the literature.

On the other hand, PTL 1 describes use of a compound represented by the formula (3) (a cyanobenzene derivative having a carbazol-9-yl group) as a light emitting material. However, the literature does not say that a perfluoroalkyl group is preferred as the substituent for the carbazol-9-yl group, and does not show specific examples of a compound having such a structure.

4CzCF$_3$Ph and 5CzCF$_3$Ph described in NPL 2 each are a light emitting material using perfluoromethylbenzene as an electron acceptor and using a carbazolyl group as an electron donor. These compounds use a perfluoromethyl group as an acceptor, but nothing is investigated in the literature relating to a case of a carbazolyl group substituted with a perfluoromethyl group.

PTL 3 describes use of a compound represented by the formula (206) as a light emitting material. This says that an electron-donating modifier group is preferred as a modifier group or the donor group containing a carbazolyl group, but says nothing relating to a perfluoroalkyl group that is an electron-attracting modifier group.

In that situation, the present inventors have further investigated the compounds described in PTL 1 and have found that a compound having such a structure that an aromatic ring is substituted with an acceptor group such as a cyano group, a perfluoromethyl group or a triazinyl group, and a carbazol-9-yl group could be further more effective so far as the HOMO level and the LUMO level thereof could be lowered. When the HOMO level and the LUMO level are lowered, the compound could be hardly oxidized, and therefore in particular, when the LUMO level of a light emitting material is lowered, it may be expected that the deterioration thereof owing to reaction of the radical species and the excitons to form during the emission process with water and oxygen can be prevented. In addition, when the HOMO level is lowered along with the LUMO level, the HOMO-LUMO gap may be narrowed and the prolongation of the wavelength in emission can be prevented, and such is advantageous in the case where antioxidation is given in consideration of shortening of the emission wavelength. Consequently, it is expected to realize a more useful light emitting material by lowering the HOMO level and the LUMO level thereof. However, NPLs 1 and 2 and PTLs 1, 2 and 3 have no description relating to a means of lowering the HOMO level and the LUMO level.

Taking the problems in the conventional art as above in consideration, the present inventors have made further investigations relating to a compound having a structure where an aromatic ring is substituted with a carbazol-9-yl group and an acceptor group in point of the HOMO level and the LUMO level thereof for the purpose of realizing a high emission efficiency. In addition, the present inventors have made assiduous studies for the purpose of deriving a formula of a compound useful as a light emitting material and further generalizing the constitution of an organic light emitting device having a high emission efficiency.

Solution to Problem

For the purpose of attaining the above-mentioned object, the present inventors have assiduously studied and, as a result, have found that, in a compound where a carbazol-9-yl group and a structural unit having a positive Hammett constant $\sigma_p$ form a π-electron conjugated system, when both the 2-position and the 7-position of the carbazol-9-yl group each are substituted with a perfluoroalkyl group, then both the HOMO level and the LUMO level of the resultant compound lower as compared with those of the compound where the carbazol-9-yl group is not substituted with a perfluoroalkyl group, and in addition, the emission efficiency of the compound markedly increases and the emission wavelength thereof is shortened to give an emission spectrum having a narrow full width at half maximum. With that, the inventors have further found that the compound where the carbazol-9-yl group substituted with a perfluoroalkyl group at the specific sites and the structural unit having a positive Hammett constant $\sigma_p$ form a π-electron conjugated system is extremely useful as a light emitting material for organic electroluminescent devices. Further, the inventors have found that the compound of the type includes a compound useful as a delayed fluorescent material, and that, using the compound, an organic light emitting device having a high emission efficiency can be provided at low cost. Based on these findings, the present inventors provide herein the following invention as a means for solving the above-mentioned problems.

[1] A compound containing a structure where a carbazol-9-yl group substituted with a perfluoroalkyl group at the 2-position and the 7-position and a structural unit having a positive Hammett constant $\sigma_p$ (but excluding an aromatic hydrocarbon group) bond to each other directly or via a π-conjugated linking group, wherein at least a part of the carbazol-9-yl group and the structural unit having a positive Hammett constant $\sigma_p$ and, if any, the π-conjugated linking group form a π-conjugated system.

[2] The compound according to [1], having a structure represented by the following formula (1).

$$(D)m-A \qquad \text{Formula (1)}$$

In the formula (1), D represents a substituent having a negative Hammett constant $\sigma_p$, A represents a group of a structural unit having a positive Hammett constant $\sigma_p$, m represents an integer of 1 or more. When m is 2 or more, plural D's may be the same or different. At least one D is a group containing a carbazol-9-yl group substituted with a perfluoroalkyl group at the 2-position and the 7-position. At least a part of the carbazol-9-yl group and at least a part of the structure except an aromatic hydrocarbon group constituting A and, if any, a linking group that links the carbazol-9-yl group and the structure form a π-electron conjugated system.

[3] The compound according to [2], wherein at least one D in the formula (1) is a carbazol-9-yl group substituted with a perfluoroalkyl group at the 2-position and the 7-position.

[4] The compound according to [2], wherein all D's in the formula (1) each are a carbazol-9-yl group substituted with a perfluoroalkyl group at the 2-position and the 7-position.

[5] The compound according to any one of [2] to [4], wherein A in the formula (1) contains an aromatic ring.

[6] The compound according to [5], wherein A in the formula (1) contains an aromatic hydrocarbon ring.

[7] The compound according to [5] or [6], wherein A in the formula (1) contains an aromatic hetero ring.

[8] The compound according to any one of [2] to [7], wherein A in the formula (1) contains a fluorine atom, an acyl group, an acyloxy group, an alkoxycarbonyl group, an aryloxycarbonyl group, a cyano group, a phosphine oxide group, a sulfonyl group, a perfluoroalkyl group, a phosphine oxide group, an amide group, an alkoxy group, a pyridyl group, a pyrimidyl group or a triazyl group.

[9] The compound according to any one of [2] to [8], wherein A in the formula (1) does not contain a bromine atom, an iodine atom or a nitro group.

[10] The compound according to any one of [2] to [9], wherein the carbazol-9-yl group and the structure except an aromatic hydrocarbon group constituting A bond to each other via an aromatic ring.

[11] The compound according to [2], wherein the compound represented by the formula (1) is a compound represented by the following formula (2).

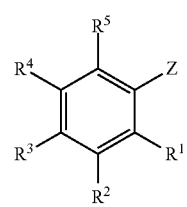

Formula (2)

In the formula (2), Z represents a cyano group, a perfluoroalkyl group, a substituted or unsubstituted triazinyl group, or a substituted or unsubstituted pyrimidinyl group, at least one of $R^1$ to $R^5$ represents a carbazol-9-yl group substituted with a perfluoroalkyl group at the 2-position and the 7-position, and the remaining $R^1$ to $R^5$ each independently represent a hydrogen atom or a substituent.

[12] The compound according to [11], wherein $R^2$ in the formula (2) is a cyano group or a perfluoromethyl group.

[13] The compound according to [12], wherein $R^1$, and $R^3$ to $R^5$ each represent a carbazol-9-yl group substituted with a perfluoroalkyl group at the 2-position and the 7-position.

[14] The compound according to [11], wherein $R^3$ in the formula (2) is a cyano group or a perfluoromethyl group.

[15] The compound according to [14], wherein $R^1$ and $R^2$ and $R^4$ and $R^5$ in the formula (2) each are a carbazol-9-yl group substituted with a perfluoroalkyl group at the 2-position and the 7-position.

[16] The compound according to any one of [1] to [15], wherein the carbazol-9-yl group substituted with a perfluoroalkyl group at the 2-position and the 7-position has a structure represented by the following formula (11).

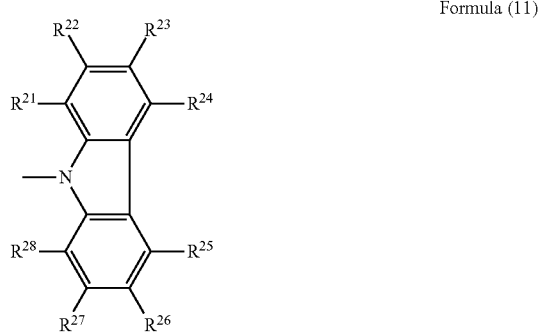

Formula (11)

In the formula (11), $R^{21}$, $R^{23}$ to $R^{26}$, and $R^{28}$ each independently represent a hydrogen atom or a substituent, and $R^{22}$ and $R^{27}$ each represent a perfluoroalkyl group.

[17] The compound according to [16], wherein at least one of $R^{21}$, $R^{23}$ to $R^{26}$, and $R^{28}$ in the formula (11) is a substituted or unsubstituted carbazolyl group.

[18] The compound according to [17], wherein $R^{23}$ in the formula (11) is a substituted or unsubstituted carbazolyl group.

[19] The compound according to [17], wherein $R^{23}$ and $R^{26}$ in the formula (11) each are a substituted or unsubstituted carbazolyl group.

[20] The compound according to any one of [17] to [19], wherein the carbazolyl group is substituted with a cyano group.

[21] The compound according to any one of [2] to [20], wherein the number of the carbazol rings existing in the molecule of the compound represented by the formula (1) is 4 or less.

[22] A light emitting material containing a compound of any one of [1] to [21].

[23] An organic light emitting device containing a compound of any one of [1] to [21].

[24] The organic light emitting device according to [23], having a light emitting layer containing a compound of any one of [1] to [21] on a substrate.

[25] The organic light emitting device according to [23] or [24], which emits delayed fluorescence.

[26] The organic light emitting device according to any one of [23] to [25], which is an organic electroluminescent device.

[27] A delayed fluorescent material having a structure represented by the above-mentioned formula (1).

Advantageous Effects of Invention

The compound of the present invention has both a deep HOMO level and a deep LUMO level and has a high emission efficiency. Accordingly, the compound of the present invention is useful as a light emitting material, and when used as a light emitting material in an organic light emitting device, an organic light emitting device having excellent emission characteristics can be realized. In addition, the compound of the present invention can emit delayed fluorescence, and therefore can be used as a delayed fluorescent material. Using a delayed fluorescent material of the compound of the present invention in an organic light emitting device, an organic light emitting device having an extremely high emission efficiency can be realized.

BRIEF DESCRIPTION OF DRAWINGS

FIG. 1 This is a schematic cross-sectional view showing a layer configuration example of an organic electroluminescent device.

FIG. 2 This is an $^1$H NMR spectrum of a compound 1.

FIG. 3 This is an $^1$H NMR spectrum of a compound 2.

FIG. 4 This is an $^1$H NMR spectrum of a compound 4.

FIG. 5 This shows a transient decay curve of emission intensity of a compound 1-doped film.

FIG. 6 This is a graph showing temperature dependency of the photoluminescence quantum yield of a compound 1 and a comparative compound 2.

FIG. 7 This is a graph showing temperature dependency of the photoluminescence quantum yield of a compound 2 and a comparative compound 4.

FIG. 8 This is a graph showing a time-dependent change of emission intensity in continuous exposure to 365 nm excited light of a sealed device using a compound 1, a comparative compound 5 or a comparative compound 6.

FIG. 9 This is a graph showing current density-voltage-luminance characteristic of an organic electroluminescent device using a compound 1.

FIG. 10 This shows an emission spectrum of an organic electroluminescent device using a compound 1 or a comparative compound 2.

DESCRIPTION OF EMBODIMENTS

The contents of the invention will be described in detail below. The constitutional elements may be described below with reference to representative embodiments and specific examples of the invention, but the invention is not limited to the embodiments and the examples. In the description, a numerical value range expressed using "A to B" denotes a range including numerical values before and after "to" as a minimum value and a maximum value, respectively.

[Compound of Invention]

The compound of the present invention is a compound containing a structure where a carbazol-9-yl group substituted with a perfluoroalkyl group at the 2-position and the 7-position and a structural unit having a positive Hammett constant $\sigma_p$ (but excluding an aromatic hydrocarbon group) bond to each other directly or via a π-conjugated linking group, wherein at least a part of the carbazol-9-yl group and the structural unit having a positive Hammett constant $\sigma_p$ and, if any, the π-conjugated linking group form a π-conjugated system. The light emitting material of the present invention is characterized by containing the compound of the present invention, and the organic light emitting device of the present invention is characterized by also containing the compound of the present invention.

The compound of the present invention has a carbazol-9-yl group substituted with a perfluoroalkyl group at the 2-position and the 7-position. The perfluoroalkyl group as referred to herein is an alkyl group where all the hydrogen atoms bonding to the carbon atom are substituted with fluorine atoms, and may be linear, branched or cyclic. The carbon number of the perfluoroalkyl group is not specifically limited but is preferably 1 to 6, more preferably 1 to 3. Specific examples of the group include a trifluoromethyl group, a pentafluoroethyl group, a heptafluoropropyl group, a heptafluoroisopropyl group, a nonafluorobutyl group, a nonafluoro-t-butyl group, an undecafluoropentyl group, a tridecafluorohexyl group, and an undecafluorocyclohexyl group.

The carbazol-9-yl group substituted with a perfluoroalkyl group at the 2-position and the 7-position preferably has a structure represented by the following formula (11).

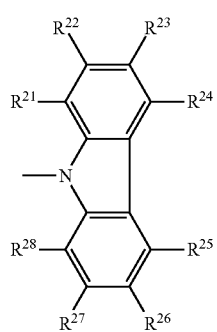

Formula (11)

In the formula (11), $R^{21}$, $R^{23}$ to $R^{26}$, and $R^{28}$ each independently represent a hydrogen atom or a substituent, and $R^{22}$ and $R^{27}$ each represent a perfluoroalkyl group.

When the formula has a substituent in $R^{21}$, $R^{23}$ to $R^{26}$, and $R^{28}$, any of them may be a substituent, and the number of the substituents is not specifically limited. For example, the number of the substituents in $R^{21}$, $R^{23}$ to $R^{26}$, and $R^{28}$ is preferably 0 to 4, more preferably 0 to 2, and may be, for example, preferably 0. When the number of the substituent in $R^{21}$, $R^{23}$ to $R^{26}$, and $R^{28}$ is 0, the Hammett constant $\sigma_p$ of the group represented by the formula (11) is −0.4 or so. When the number of the substituents in $R^{21}$, $R^{23}$ to $R^{26}$, and $R^{28}$ is 2 or more, the two or more substituents may be the same as or different from each other, but are preferably the same. When the formula has a substituent in $R^{21}$, $R^{23}$ to $R^{26}$, and $R^{28}$, preferably, at least one of $R^{23}$ to $R^{26}$ is a substituent. For example, a case where $R^{23}$ and $R^{26}$ are substituents, and a case where $R^{24}$ and $R^{25}$ are substituents are preferred, and a case where $R^{23}$ and $R^{26}$ are substituents is more preferred. When $R^{23}$ and $R^{26}$ are substituents, the oxidation resistance of the compound may tend to be improved. It is presumed that, in the case, the 3-position and the 6-position of the carbazol-9-yl group each are protected with a substituent so as to make the compound hardly oxidized, and accordingly, the compound can be prevented from being dimerized and the stability thereof can therefore improve. The substituent represented by $R^{23}$ and $R^{26}$ is preferably an alkyl group having 1 to 10 carbon atoms, an aryl group or a heteroaryl group, more preferably an alkyl group having 1 to 5 carbon atoms, or an aryl group, and even more preferably a methyl group, a tert-butyl group or a phenyl group.

A case where $R^{21}$, $R^{23}$ to $R^{26}$, and $R^{28}$ each are a perfluoroalkyl group as a substituent is not excluded from the present invention. However, an organic light emitting device using a compound where $R^{23}$ and $R^{26}$ each are a perfluoroalkyl group exhibits more excellent performance than an organic light emitting device using a compound where $R^{23}$ and $R^{26}$ each are not a perfluoroalkyl group.

Examples of the substituent that $R^{21}$, $R^{23}$ to $R^{26}$, and $R^{28}$ in the formula (11) may represent include a hydroxy group, a halogen atom, a cyano group, an alkyl group having 1 to 20 carbon atoms, an alkoxy group having 1 to 20 carbon atoms, an alkylthio group having 1 to 20 carbon atoms, an alkyl-substituted amino group having 1 to 20 carbon atoms, an acyl group having 2 to 20 carbon atoms, an aryl group having 6 to 40 carbon atoms, a heteroaryl group having 3 to 40 carbon atoms, a diarylamino group having 12 to 40 carbon atoms, a substituted or unsubstituted carbazolyl group having 12 to 40 carbon atoms, an alkenyl group having 2 to 10 carbon atoms, an alkynyl group having 2 to 10 carbon atoms, an alkoxycarbonyl group having 2 to 10 carbon atoms, an alkylsulfonyl group having 1 to 10 carbon atoms, a haloalkyl group having 1 to 10 carbon atoms, an amide group, an alkylamide group having 2 to 10 carbon atoms, a trialkylsilyl group having 3 to 20 carbon atoms, a trialkylsilylalkyl group having 4 to 20 carbon atoms, a trialkylsilylalkenyl group having 5 to 20 carbon atoms, a trialkylsilylalkynyl group having 5 to 20 carbon atoms, and a nitro group. Among these specific examples, those that may be substituted may be substituted with a substituent. More preferred substituents include a halogen atom, a cyano group, a substituted or unsubstituted alkyl group having 1 to 20 carbon atoms, an alkoxy group having 1 to 20 carbon atoms, a substituted or unsubstituted aryl group having 6 to 40 carbon atoms, a substituted or unsubstituted heteroaryl group having 3 to 40 carbon atoms, a substituted or unsubstituted diarylamino group having 12 to 40 carbon atoms, and a substituted or unsubstituted carbazolyl group having 12 to 40 carbon atoms. Even more preferred substituents include a fluorine atom, a chlorine atom, a cyano group, a substituted or unsubstituted alkyl group having 1 to 10 carbon atoms, a substituted or unsubstituted alkoxy group having 1 to 10 carbon atoms, a substituted or unsubstituted dialkylamino group having 1 to 10 carbon atoms, a substituted or unsubstituted aryl group having 6 to 15 carbon atoms, and a substituted or unsubstituted heteroaryl group having 3 to 12 carbon atoms.

Above all, $R^{23}$ and $R^{26}$ in the formula (11) each are preferably substituents, more preferably an alkyl group having 1 to 20 carbon atoms or an aryl group having 6 to 40 carbon atoms, even more preferably an alkyl group having 1 to 10 carbon atoms, or an aryl group having 6 to 15 carbon atoms.

The alkyl group referred to in this description may be linear, branched or cyclic, and more preferably has 1 to 6 carbon atoms. Specific examples of the group include a methyl group, an ethyl group, a propyl group, a butyl group, a t-butyl group, a pentyl group, a hexyl group, an isopropyl group, and a cyclohexyl group. The alkoxy group may be linear, branched or cyclic, and more preferably has 1 to 6 carbon atoms. Specific examples of the group include a methoxy group, an ethoxy group, a propoxy group, a butoxy group, a t-butoxy group, a pentyloxy group, a hexyloxy group, and an isopropoxy group. Two alkyl groups of the dialkylamino group may be the same as or different from each other, but are preferably the same. Two alkyl groups of the dialkylamino group may be each independently linear, branched or cyclic, more preferably each having 1 to 6 carbon atoms. Specific examples of the groups include a methyl group, an ethyl group, a propyl group, a butyl group, a pentyl group, a hexyl group, and an isopropyl group. The aryl group may be a single ring or a fused ring, and specific examples thereof include a phenyl group and a naphthyl group. The heteroaryl group may be a single ring or a fused ring, and specific examples thereof include a pyridyl group, a pyridazyl group, a pyrimidyl group, a triazyl group, a triazolyl group, a benzotriazolyl group, and a carbazolyl group. These heteroaryl groups may be groups bonding via the hetero atom, or may be groups bonding via the carbon atom constituting the heteroaryl ring. A part or all of hydrogen atoms existing in the groups described in this section may be substituted with a substituent. For example, a part or all of hydrogen atoms of the alkyl group, the aryl group and the heteroaryl group may be substituted with fluorine atoms.

At least one of $R^{21}$, $R^{23}$ to $R^{26}$, and $R^{28}$ may be, for example, a carbazolyl group, and examples of the carbazolyl group include a carbazol-2-yl group, a carbazol-3-yl group, and a carbazol-9-yl group. When at least one of $R^{21}$, $R^{23}$ to $R^{26}$, and $R^{28}$ is a carbazolyl group, HOMO can be broadly delocalized to improve the emission characteristics and the stability of the material. When at least one of $R^{21}$, $R^{23}$ to $R^{26}$, and $R^{28}$ is a carbazolyl group, the carbazolyl group may be unsubstituted or substituted with a substituent. Preferably, a carbazolyl group substituted with a group having a positive Hammett constant $\sigma_p$ is used. With that, charge transfer may be prevented between the carbazolyl group substituted with a perfluoroalkyl group and the carbazolyl group of $R^{21}$, $R^{23}$ to $R^{26}$, and $R^{28}$ therefore realizing more efficient light emission. For example, as one example of the case, a carbazolyl group substituted with a perfluoroalkyl group or a cyano group may be mentioned. In the case where the carbazolyl group represented by $R^{21}$, $R^{23}$ to $R^{26}$, and $R^{28}$ is substituted with a perfluoroalkyl group or a cyano group, the substituting position of the perfluoroalkyl group and the cyano group is not specifically limited, but examples of the case include an embodiment of a carbazol-2-yl group substituted at least at the 6-position and the 8-position, an embodiment of a carbazol-3-yl group substituted at the 7-position and an embodiment of a carbazol-9-yl group substituted at least at the 2-position and the 7-position. In the case where the carbazolyl group represented by $R^{21}$, $R^{23}$ to $R^{26}$, and $R^{28}$ is substitutable at the 3-position, the 6-position and the 9-position, examples of the substituent include an alkyl group having 1 to 20 carbon atoms, and an aryl group having 6 to 40 carbon atoms, more limitatively including an alkyl group having 1 to 10 carbon atoms and an aryl group having 6 to 15 carbon atoms. When the carbazolyl group is substituted at any of the 3-position, 6-position and the 9-position, the compound of the type is hardly oxidized and can be prevented from being dimerized. For the reason, the compound of the type is advantageous in point of stability. In the case where any of $R^{21}$, $R^{23}$ to $R^{26}$, and $R^{28}$ is a carbazolyl group, for example, at least one of $R^{23}$ to $R^{26}$ may be a carbazolyl group, or both $R^{23}$ and $R^{26}$ each may be a carbazolyl group. However, from the viewpoint of practicality, the number of the carbazol rings existing in the molecule of the compound represented by the formula (1) is preferably 4 or less.

The compound of the present invention has a structural unit having a positive Hammett constant $\sigma_p$. The "structural unit having a positive Hammett constant $\sigma_p$" as referred to herein means an electron-attracting structural unit, and does not include an atomic group containing both an electron-attracting structural unit and an electron-donating structural unit and exhibiting an electron-attracting property as a whole, such as an atomic group of an electron attracting structural unit substituted with an electron-donating structural unit. In the case where such an atomic group is contained as a part of the structure of the compound of the present invention, a virtual atomic group where the electron-donating structural unit contained in that atomic group is substituted with a hydrogen atom is simulated, and when the virtual atomic group has a positive Hammett $\sigma_p$, then the electron-attracting structural unit contained in the virtual atomic group is considered to have a positive Hammett constant $\sigma_p$. Preferred examples of the structural unit having a positive Hammett constant $\sigma_p$ (namely, the electron-attracting structural unit) include an aromatic heterocyclic group (for example, a pyridine ring group, a pyrimidine ring group, a triazine ring group), a cyano group, —CO— and —SO$_2$—. An aromatic hydrocarbon ring group such as a group of a benzene ring may also be included in the structural unit having a positive Hammett constant $\sigma_p$, but the compound of the present invention has at least one structural unit having a positive Hammett constant $\sigma_p$ in addition to such an aromatic hydrocarbon ring group.

The Hammett constant $\sigma_p$ is one propounded by L. P. Hammett, and is one to quantify the influence of a substituent on acid dissociation equilibrium of a para-substituted benzoic acid. Specifically, this is a constant ($\sigma_p$) peculiar to the substituent in the following expression that is established between a substituent of a para-substituted benzoic acid and the acid dissociation equilibrium constant thereof.

$$\sigma_p = \log K_x - \log K_H$$

In the above expression, $K_H$ represents an acid dissociation equilibrium constant of a benzoic acid not having a substituent, and $K_x$ represents an acid dissociation equilibrium constant of a benzoic acid substituted with a substituent at the para-position thereof. Regarding the description of the Hammett constant $\sigma_p$ and the numeral value of each substituent, reference may be made to Hansch, C. et. al., Chem. Rev., 91, 165-195 (1991).

A positive Hammett constant $\sigma_p$ means that the substituent is an acceptor-like group (electron-attracting group), and a negative Hammett constant $\sigma_p$ means that the substituent is a donor-type group (electron-donating group).

The structural unit having a positive Hammett constant $\sigma_p$ contained in the compound of the present invention preferably has a Hammett constant $\sigma_p$ of 0.05 or more, more preferably 0.1 or more, even more preferably 0.3 or more. Preferred examples of the substituent having a positive Hammett constant $\sigma_p$ include a fluorine atom, an acyl group, an acyloxy group, an alkoxycarbonyl group, an aryloxycarbonyl group, a cyano group, a phosphine oxide group, a sulfonyl group, a perfluoroalkyl group, a phosphine oxide group, an amide group, an alkoxy group, a pyridyl group, a pyrimidyl group, and a triazyl group, and these groups not substituted with an electron-donating group can be considered to be the above-mentioned "structural unit having a positive Hammett constant $\sigma_p$". From the viewpoint of light emission performance, durability and electrochemical stability, preferably, a structural unit except a bromine atom, an iodine atom and a nitro group is selected as the structural unit having a positive Hammett constant $\sigma_p$, but in the case where even when the structural unit has a bromine atom, an iodine atom or a nitro group, it may not have any negative influence on the light emission performance, the durability and the electrochemical stability of the compound to such a degree as to detract from the practicability of the compound, the structural unit of the type may be selected.

The compound of the present invention has a structure where a carbazol-9-yl group substituted with a perfluoroalkyl group at the 2-position and the 7-position and a structural unit having a positive Hammett constant $\sigma_p$ (but excluding an aromatic hydrocarbon group) bond to each other directly or via a π-conjugated linking group. With that, in this, at least a part of the carbazol-9-yl group and the structural unit having a positive Hammett constant $\sigma_p$ and, if any, the π-conjugated linking group form a π-electron conjugated system. The π-conjugated linking group is not specifically limited in point of the type thereof so far at the group may form a π-electron conjugated system, for which employable here is hyperconjugation through interaction with a π* orbital where the σ-orbital electrons are spatially near to each other or a vacant p-orbital. Specifically, an aromatic hydrocarbon linking group, or a hyperconjugated methylene ($CH_2$) group, $CF_2$ group, or $C(CF_3)_2$ group is preferably used as the π-conjugated linking group. The aromatic hydrocarbon ring to constitute the aromatic hydrocarbon linking group preferably has 6 to 40 carbon atoms, and is more preferably a benzene ring or a condensed ring having a structure where plural benzene rings are condensed. Examples of the aromatic hydrocarbon ring include a benzene ring, a naphthalene ring, a fluorene ring, a phenanthrene ring, an anthracene ring, a triphenylene ring, a pyrene ring, a chrysene ring, a tetracene ring, a benzopyrene ring, a perylene ring, a coronene ring, a corannulene ring, a phenalene ring, and a triangulene ring; a benzene ring and a naphthalene ring are preferred; and a benzene ring is more preferred. Specific examples of the aromatic hydrocarbon linking group include a phenylene group, a 1,2-naphthylene group, a 1,3-naphthylene group, a 1,4-naphthylene group, a 1,5-naphthylene group, a 1,8-naphthylene group, a 2,3-naphthylene group, a 2,6-naphthylene group, and a 2,7-naphthylene group.

[Compound Represented by Formula (1)]

The compound of the present invention is preferably one having a structure represented by the following formula (1). Also preferably, the light emitting material of the present invention contains a compound represented by the following formula (1). Further, the organic light emitting device of the present invention preferably contain a compound represented by the following formula (1). The compound represented by the formula (1) is described below.

(D)m–A  Formula (1)

In the formula (1), D represents a substituent having a negative Hammett constant $\sigma_p$. At least one D is a group containing a carbazol-9-yl group substituted with a perfluoroalkyl group at the 2-position and the 7-position. m represents an integer of 1 or more, and is preferably 2 or more, and may be, for example, 3 or more or 4 or more. When m is 2 or more, one or 2 or more of plural D's each may be a carbazol-9-yl group substituted with a perfluoroalkyl group at the 2-position and the 7-position. All of plural D's each may be a carbazol-9-yl group substituted with a perfluoroalkyl group at the 2-position and the 7-position, or a part of D's may be a carbazol-9-yl group substituted with a perfluoroalkyl group at the 2-position and the 7-position., but preferably all D's each are a carbazol-9-yl group substituted with a perfluoroalkyl group at the 2-position and the 7-position. When two or more D's each are a carbazol-9-yl group substituted with a perfluoroalkyl group at the 2-position and the 7-position, they may be the same or different, but are preferably the same.

When m is 2 or more an a part of plural D's each are a carbazol-9-yl group substituted with a perfluoroalkyl group at the 2-position and the 7-position, examples of the substituent having a negative Hammett constant $\sigma_p$ that the remaining D's may represent include a substituted amino group, an alkoxy group and an alkyl group. Here, the substituent that the substituted amino group may have includes an aryl group having 6 to 40 carbon atoms, an alkyl group having 1 to 20 carbon atoms, and an alkenyl group having 2 to 10 carbon atoms, and those substituents may bond to each other to form a heteroaryl group. Preferred examples of the substituted amino group and the heteroaryl group include those represented by the following formulae (12) to (15).

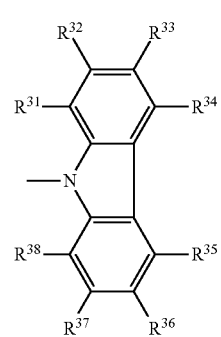

Formula (12)

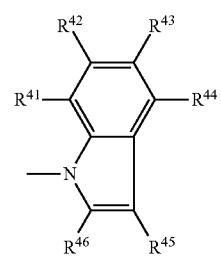

Formula (13)

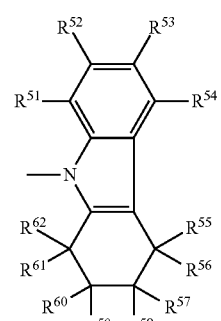

Formula (14)

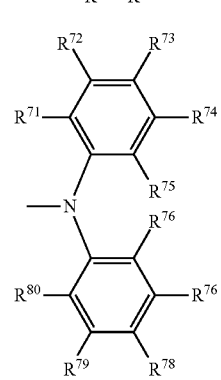

Formula (15)

In the formula (12), $R^{31}$ to $R^{38}$ each independently represent a hydrogen atom or a substituent. However, $R^{32}$ and $R^{37}$ each are a substituent except a perfluoroalkyl group. In the formulae (13) to (15), $R^{41}$ to $R^{46}$, $R^{51}$ to $R^{62}$ and $R^{71}$ to $R^{80}$ each independently represent a hydrogen atom or a substituent. Regarding the substituents in the formulae (12) to (15), the substituting position and the substituting number thereof are not specifically limited. The number of the substituents is preferably 0 to 6, more preferably 0 to 4 and is also preferably 0 to 2. When the formula has plural substituents, they may be the same as or different from each other, but are preferably the same.

In the case where the group represented by the formula (12) has a substituent, preferably, any of $R^{32}$ to $R^{37}$ is a substituent. Preferred examples of the case include a case where $R^{32}$ and $R^{37}$ are substituents, a case where $R^{33}$ and $R^{36}$ are substituents, and a case where $R^{34}$ and $R^{35}$ are substituents.

In the case where the group represented by the formula (13) has a substituent, preferably, any of $R^{42}$ to $R^{46}$ is a substituent. Preferred examples of the case include a case where $R^{42}$ is a substituent and a case where $R^{43}$ is a substituent.

In the case where the group represented by the formula (14) has a substituent, preferably, any of $R^{52}$ to $R^{60}$ is a substituent. Preferred examples of the case include a case where any of $R^{52}$ to $R^{54}$ is a substituent and a case where any of $R^{55}$ to $R^{60}$ is a substituent.

In the case where the group represented by the formula (15) has a substituent, preferably, any of $R^{72}$ to $R^{74}$ and $R^{77}$ to $R^{79}$ is a substituent. Preferred examples of the case include a case where $R^{72}$ and $R^{79}$ are substituent, a case where $R^{73}$ and $R^{78}$ are substituent, a case where $R^{74}$ and $R^{77}$ are substituents, and a case where $R^{72}$, $R^{74}$, $R^{77}$ and $R^{79}$ are substituents. In particular, a case where $R^{74}$ and $R^{77}$ are substituents and a case where $R^{72}$, $R^{74}$, $R^{77}$ and $R^{79}$ are substituents are more preferred. In these cases, more preferably, the substituents each are independently a substituted or unsubstituted alkyl group having 1 to 20 carbon atoms, or a substituted or unsubstituted aryl group having 6 to 40 carbon atoms, and even more preferably, an unsubstituted alkyl group having 1 to 6 carbon atoms, an unsubstituted aryl group having 6 to 10 carbon atoms, or an aryl group having 6 to 10 carbon atoms and substituted with an aryl group having 6 to 10 carbon atoms. $R^{75}$ and $R^{76}$ may bond to each other to form a linking group. The carbon number of the linking chain to constitute the liking group is preferably 1 or 2. Specific examples of the linking chain include —O—, —S—, —C(=O)—, —N($R^{81}$)—, —C($R^{82}$)($R^{83}$)—, and —C(=O)—N($R^{84}$)—. Here, $R^{81}$ to $R^{84}$ each independently represent a hydrogen atom or a substituent, and examples of the substituent include an alkyl group having 1 to 10 carbon atoms and an aryl group having 6 to 14 carbon atoms. $R^{75}$ and $R^{76}$ may bond to each other to form a cyclic structure (spiro structure).

Regarding the preferred ranges and specific examples of the substituent that $R^{31}$ to $R^{38}$ in the formula (12), $R^{41}$ to $R^{46}$ in the formula (13), $R^{51}$ to $R^{62}$ in the formula (14), and $R^{71}$ to $R^{80}$ in the formula (15) may have, reference may be made to the preferred ranges and the specific examples of the substituent that $R^{21}$, $R^{23}$ to $R^{26}$, and $R^{28}$ in the formula (11) mentioned hereinabove.

In the formula (1), A represents a group of a structural unit having a positive Hammett constant $\sigma_p$. The "structural unit having a positive Hammett constant $\sigma_p$" as referred to herein has the same semantic content as that described in the section of [Compound of Invention] given hereinabove. A may be composed of a single structural unit having a positive Hammett constant $\sigma_p$ (electron-attracting structural unit) alone, or may be composed of two or more kinds of structural units each having a positive Hammett constant $\sigma_p$ and bonding to each other. In the case where two or more kinds of structural units each having a positive Hammett constant $\sigma_p$ bond to each other, all the bonding structural units each having a positive Hammett constant $\sigma_p$ is considered to be an atomic group A.

Preferably, A contains an aromatic ring as the structural unit having a positive Hammett constant $\sigma_p$. The aromatic ring may be an aromatic hydrocarbon ring or an aromatic hetero ring, but is preferably an aromatic hydrocarbon ring. Regarding the aromatic hydrocarbon ring, reference may be made to the description in the section of [Compound of Invention] given hereinabove. The hetero atom of the aromatic hetero ring is preferably at least any of N, O and S. Also preferably, the carbon number of the aromatic hetero ring is 3 to 40, and more preferably, the ring is a 5-membered ring, a 6-membered ring, or a condensed ring having a structure formed through condensation of a 5-membered ring and a 6-membered ring. Examples of the aromatic hetero ring include a furan ring, a thiophene ring, a pyrrole ring, an oxazole ring, an isoxazole ring, a thiazole ring, an isothiazole ring, an imidazole ring, a pyrazole ring, a furazan ring, a pyridine ring, a pyridazine ring, a pyrimidine ring, a pyrazine ring, a triazine ring, a thiadiazole ring, and an imide ring; and a furan ring, a thiophene ring, a pyrrole ring, an oxazole ring, an isoxazole ring, a thiazole ring, an isothiazole ring, an imidazole ring, a pyrazole ring, a furazan ring, a triazine ring, a thiadiazole ring and an imide ring are preferred. Of the substituents bonding to the aromatic ring contained in A in the formula (1), the substituent having a negative Hammett constant $\sigma_p$ corresponds to D, and the substituent having a positive Hammett constant $\sigma_p$ is considered to be a part of A.

In the formula (1), at least a part of the carbazol-9-yl group and at least a part of the structure except an aromatic hydrocarbon group constituting A, and, if any, a linking group that links the carbazol-9-yl group and the structure form a π-electron conjugated system.

The compound represented by the formula (1) is preferably a compound represented by the following formula (2).

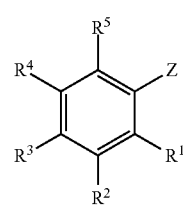

Formula (2)

In the formula (2), Z represents a cyano group, a perfluoroalkyl group, a substituted or unsubstituted triazinyl group, or a substituted or unsubstituted pyrimidinyl group, at least one of $R^1$ to $R^5$ represents a carbazol-9-yl group substituted with a perfluoroalkyl group at the 2-position and the 7-position, and the remaining $R^1$ to $R^5$ each independently represent a hydrogen atom or a substituent. $R^1$ to $R^5$ may also be each independently a cyano group, a perfluoroalkyl group, a substituted or unsubstituted triazinyl group or a substituted or unsubstituted pyrimidinyl group. In the case where any one of Z and $R^1$ to $R^5$ is a cyano group or a perfluoroalkyl group, examples of a combination of these groups include a combination of Z and $R^2$, and a combination of Z and $R^3$. In the case where any two of Z and $R^1$ to $R^5$ each are a cyano group or a perfluoroalkyl group, examples of a combination of these groups include a combination of Z and $R^1$ and $R^2$ and a combination of Z and $R^1$ and $R^3$. In the case where any three of Z and $R^1$ to $R^5$ each are a cyano group or a perfluoroalkyl group, an example of a combination of these groups include a combination of Z and $R^1$ and $R^3$ and $R^4$. Among these, preferred is a case where Z and $R^2$, or Z and $R^3$ each are a cyano group or a perfluoroalkyl group. When at least one of Z and $R^1$ to $R^5$ is a group selected from a cyano group, a perfluoroalkyl group, a substituted or unsubstituted triazinyl group or a substituted or unsubstituted pyrimidinyl group, the groups may be the same or different.

In the formula (2), at least one of $R^1$ to $R^5$ is a carbazol-9-yl group substituted with a perfluoroalkyl group at the 2-position and the 7-position. Regarding the description and the preferred range of the carbazol-9-yl group substituted with a perfluoroalkyl group at the 2-position and the 7-position, reference may be made to the description and the preferred range of the carbazol-9-yl group substituted with a perfluoroalkyl group at the 2-position and the 7-position in the section of [Compound of Invention] given hereinabove. When 2 or more of $R^1$ to $R^5$ each are a carbazol-9-yl group substituted with a perfluoroalkyl group at the 2-position and the 7-position, they may be the same or different.

In the case where at least one of $R^1$ to $R^5$ is a carbazol-9-yl group substituted with a perfluoroalkyl group at the 2-position and the 7-position, the group may be any of $R^1$ to $R^3$. In the case where any two of the groups each are a carbazol-9-yl group substituted with a perfluoroalkyl group at the 2-position and the 7-position, examples of the case include a case of a combination of $R^1$ and $R^2$, a combination of $R^2$ and $R^3$, a combination of $R^3$ and $R^4$, a combination of $R^1$ and $R^3$, and a combination of $R^2$ and $R^4$; and a combination of $R^2$ and $R^3$, or a combination of $R^3$ and $R^4$ is preferred. In the case where any three of the groups each are a carbazol-9-yl group substituted with a perfluoroalkyl group at the 2-position and the 7-position, an example of the case is a combination of $R^1$ and $R^3$ and $R^4$. In the case where any four of the groups each are a carbazol-9-yl group substituted with a perfluoroalkyl group at the 2-position and the 7-position, examples of the case include a case of a combination of $R^1$ and $R^3$ and $R^4$ and $R^5$, and a case of a combination of $R^1$ and $R^2$ and $R^4$ and $R^5$.

As described above, in the formula (2), Z represents a cyano group, a perfluoroalkyl group, a substituted or unsubstituted triazinyl group, or a substituted or unsubstituted pyrimidinyl group, at least one of $R^1$ to $R^5$ represents a carbazol-9-yl group substituted with a perfluoroalkyl group at the 2-position and the 7-position, and the remaining $R^1$ to $R^5$ each independently represent a hydrogen atom or a substituent.

Examples of the substituent that $R^1$ to $R^5$ may represent, and preferred examples of the substituent with which the triazinyl group and the pyrimidinyl group may be substituted include a hydroxy group, a halogen atom, an alkyl group having 1 to 20 carbon atoms, an alkoxy group having 1 to 20 carbon atoms, an alkylthio group having 1 to 20 carbon atoms, an alkyl-substituted amino group having 1 to 20 carbon atoms, an acyl group having 2 to 20 carbon atoms, an aryl group having 6 to 40 carbon atoms, a heteroaryl group having 3 to 40 carbon atoms, an alkenyl group having 2 to 10 carbon atoms, an alkynyl group having 2 to 10 carbon atoms, an alkoxycarbonyl group having 2 to 10 carbon atoms, an alkylsulfonyl group having 1 to 10 carbon atoms, an amide group, an alkylamide group having 2 to 10 carbon atoms, a trialkylsilyl group having 3 to 20 carbon atoms, a trialkylsilylalkyl group having 4 to 20 carbon atoms, a trialkylsilylalkenyl group having 5 to 20 carbon atoms, a trialkylsilylalkynyl group having 5 to 20 carbon atoms, and a nitro group. Of these specific examples, those substitutable with a substituent may be substituted. More preferred examples of the substituent include a hydroxy group, a halogen atom, a substituted or unsubstituted alkyl group having 1 to 20 carbon atoms, a substituted or unsubstituted alkoxy group having 1 to 20 carbon atoms, a substituted or unsubstituted dialkylamino group having 1 to 20 carbon atoms, a substituted or unsubstituted aryl group having 6 to 40 carbon atoms, and a substituted or unsubstituted heteroaryl group having 3 to 40 carbon atoms. Even more preferred examples of the substituent include a hydroxy group, a fluorine atom, a chlorine atom, a substituted or unsubstituted alkyl group having 1 to 10 carbon atoms, a substituted or unsubstituted alkoxy group having 1 to 10 carbon atoms, a substituted or unsubstituted dialkylamino group having 1 to 10 carbon atoms, a substituted or unsubstituted aryl group having 6 to 15 carbon atoms, and a substituted or unsubstituted heteroaryl group having 3 to 12 carbon atoms. Even more preferred are a hydroxy group, a fluorine atom and a chlorine atom.

Preferred examples of the substituent that $R^1$ to $R^5$ may represent further include the groups represented by the above-mentioned formulae (12) to (15). Regarding the description and the preferred ranges of the groups represented by the formulae (12) to (15), reference may be made to the description and the preferred ranges of the groups represented by the formulae (12) to (15) in the formula (1) given hereinabove.

In the formula (2), preferably, three or less of $R^1$ to $R^5$ are hydrogen atoms, more preferably two or less are hydrogen atoms, and also preferably, none of these is a hydrogen atom.

One preferred combination is, for example, a case where in the formula (2), Z and $R^2$ each are a cyano group or a perfluoromethyl group, and at least one of $R^1$ and $R^4$ is a carbazol-9-yl group substituted with a perfluoroalkyl group at the 2-position and the 7-position; another preferred combination is a case where Z and $R^3$ each are a cyano group or a perfluoromethyl group, and at least one of $R^1$, $R^2$, $R^4$ and $R^5$ is a carbazol-9-yl group substituted with a perfluoroalkyl group at the 2-position and the 7-position. A more preferred combination is, for example, a case where in the formula (2), Z is a cyano group or a perfluoromethyl group, and all of $R^1$ to $R^5$ each are a carbazol-9-yl group substituted with a perfluoroalkyl group at the 2-position and the 7-position. Another more preferred combination is a case where Z is a cyano group or a perfluoromethyl group, and $R^1$, $R^2$, $R^4$ and $R^5$ each are a carbazol-9-yl group substituted with a perfluoroalkyl group at the 2-position and the 7-position. Still another preferred combination is a case where Z and $R^2$ each are a cyano group or a perfluoromethyl group, and $R^1$, $R^3$, $R^4$ and $R^5$ each are a carbazol-9-yl group substituted with a perfluoroalkyl group at the 2-position and the 7-position. Still another preferred combination is a case where Z and $R^3$ each are a cyano group or a perfluoromethyl group, and $R^1$, $R^3$, $R^4$ and $R^5$ each are a carbazol-9-yl group substituted with a perfluoroalkyl group at the 2-position and the 7-position.

The compound represented by the formula (2) may be controlled in point of the symmetry and the linearity of the molecular structure thereof by selecting the substituting position and the substituting number of the carbazol-9-yl group substituted with a perfluoroalkyl group at the 2-position and the 7-position on the benzene ring, the bonding site of the carbazolyl group to the benzene ring, the substituting position and the substituting number of the carbazolyl group to be introduced into that carbazolyl group, and the bonding site of the carbazolyl group to that carbazolyl group. For example, when the symmetry of the molecule is high, it is advantageous in that the electron transition probability is high. On the other hand, a linear molecule is preferred since the polarization is large and the quantum yield increases. Introduction of a cyano group, a perfluoroalkyl group or a hetero ring acts to increase molecular polarity.

In the following, specific examples of the compound of the present invention are show, but the compounds for use in the present invention should not be limitatively interpreted by these specific examples. In the formulae, Y represents a substituent selected from a cyano group or a perfluoromethyl group.

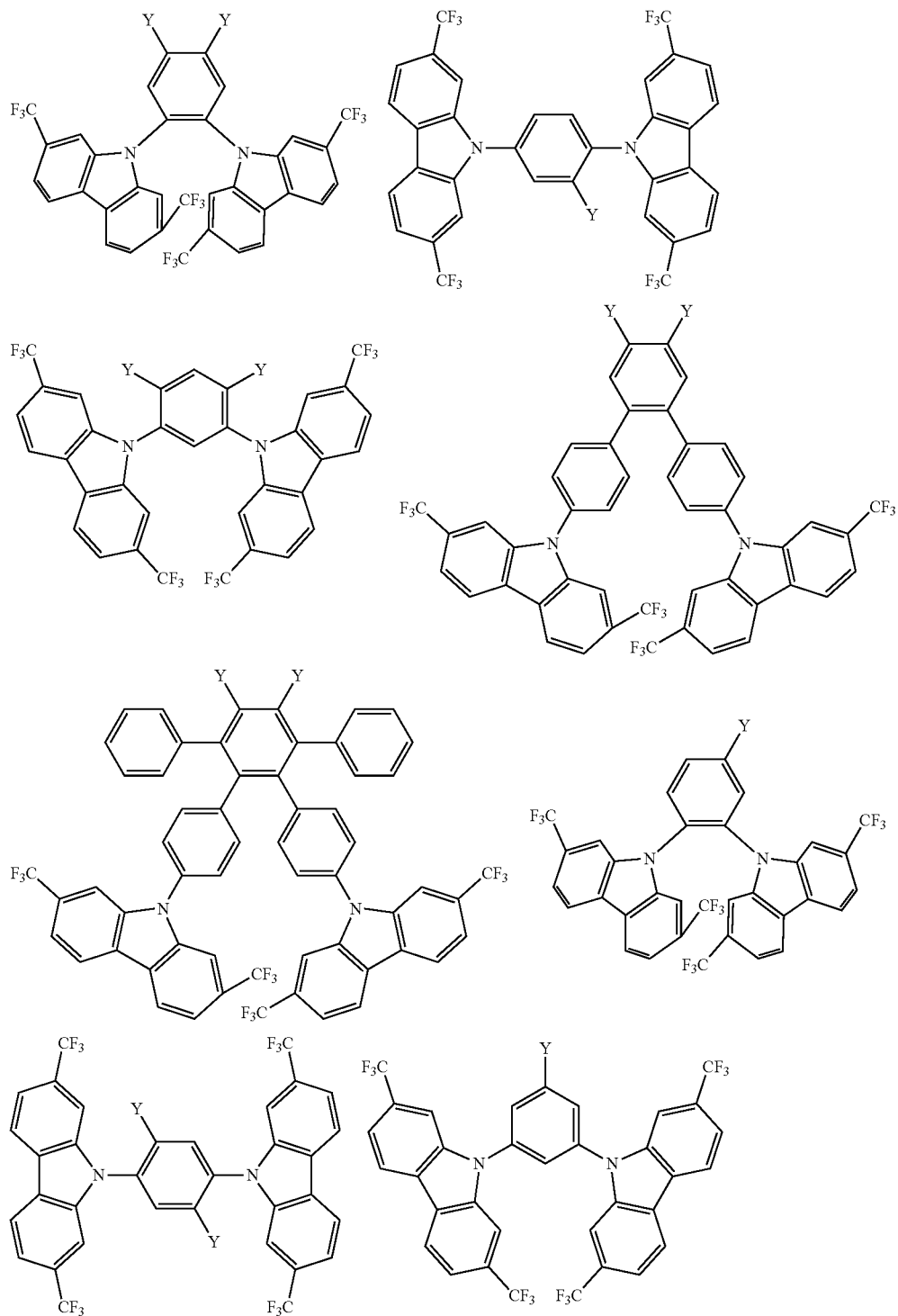

-continued
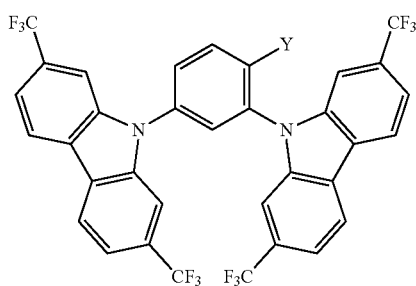 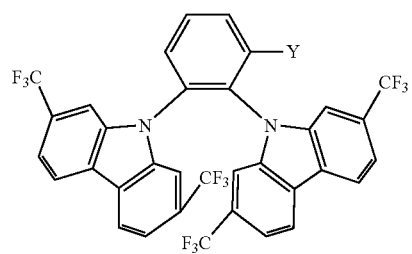
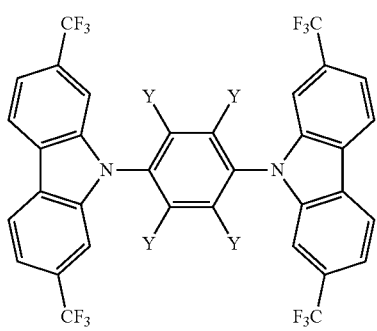 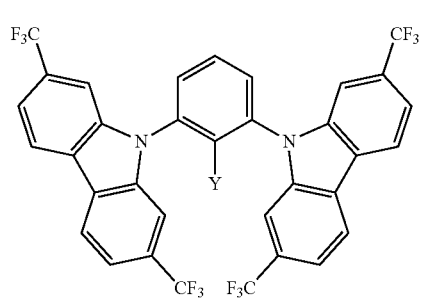
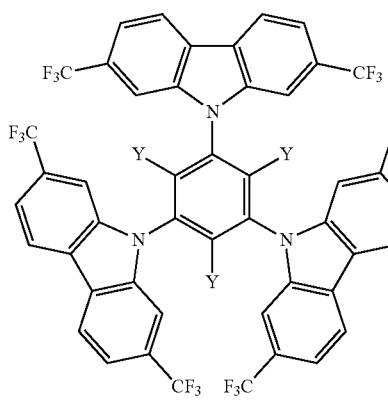 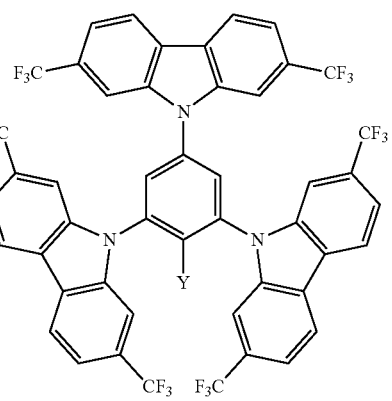
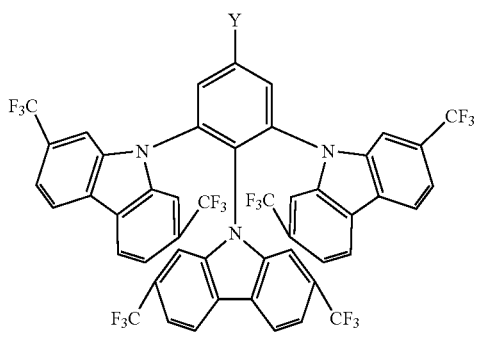 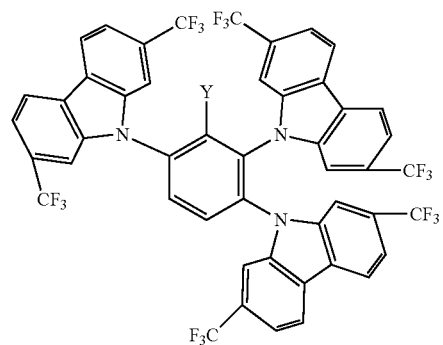

23
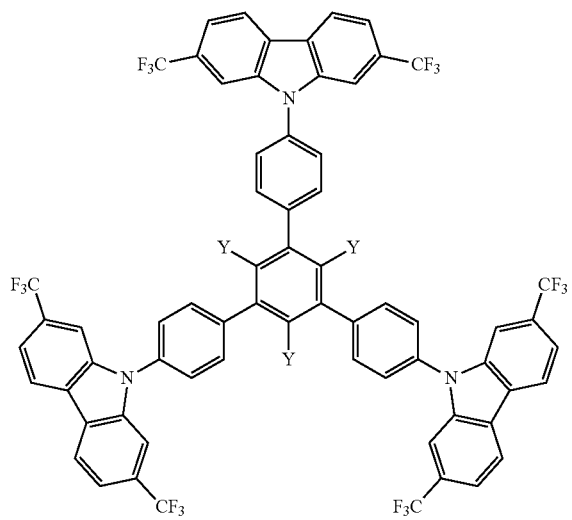
24
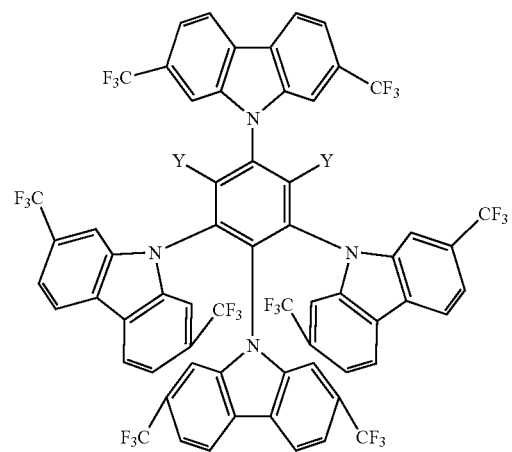
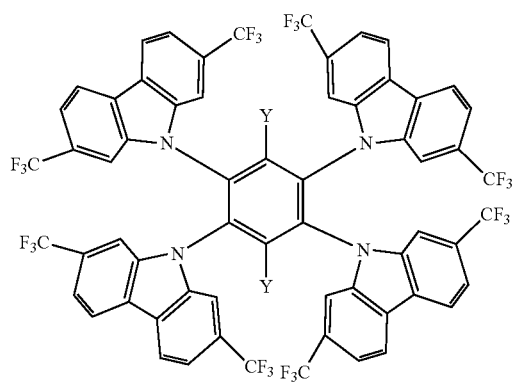
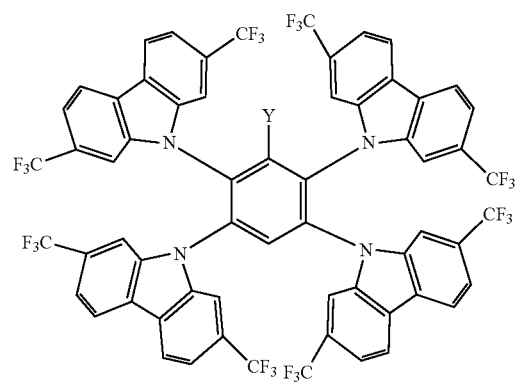
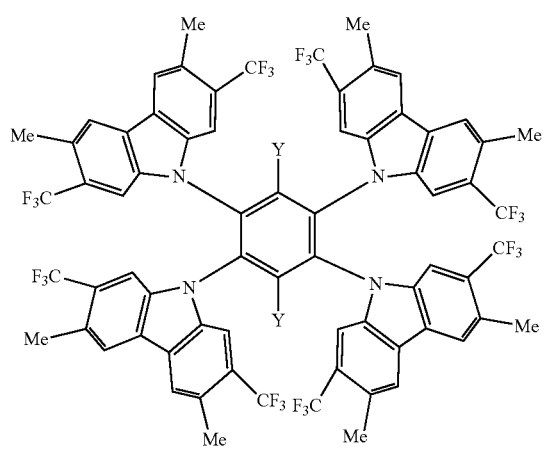
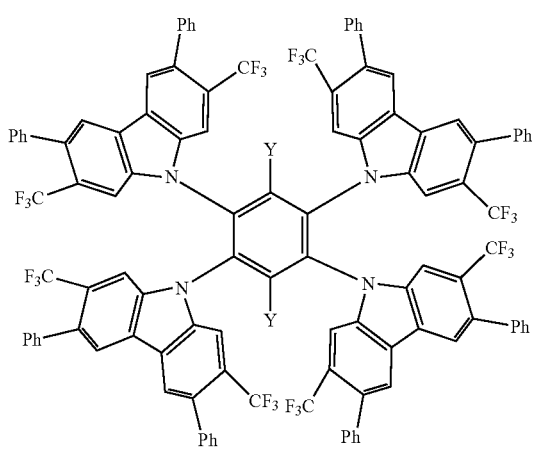

-continued
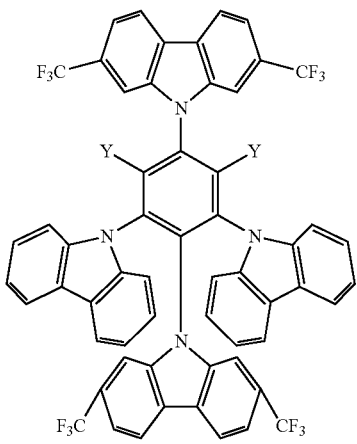
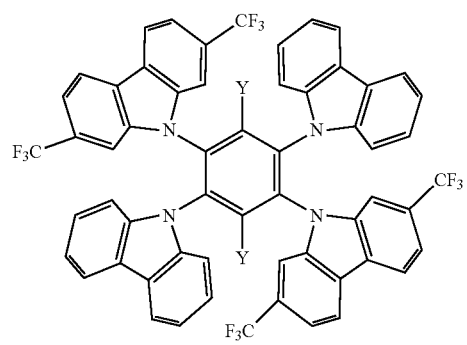
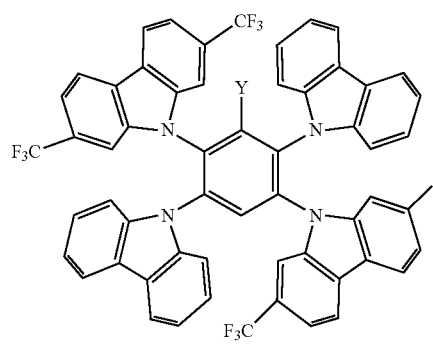
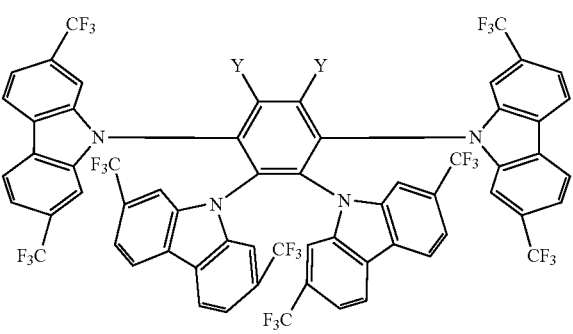
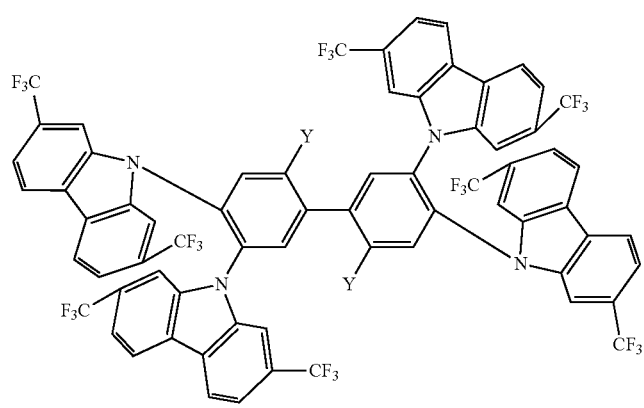
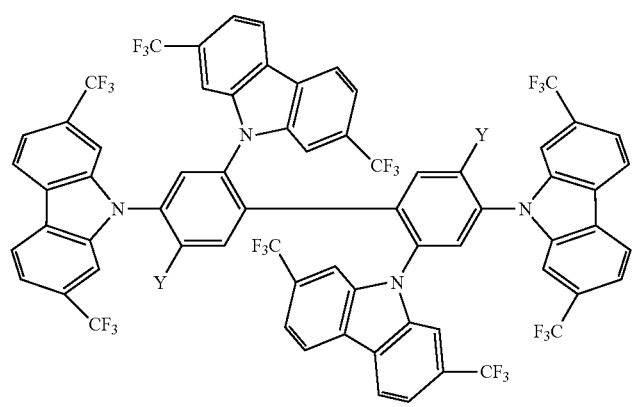

-continued
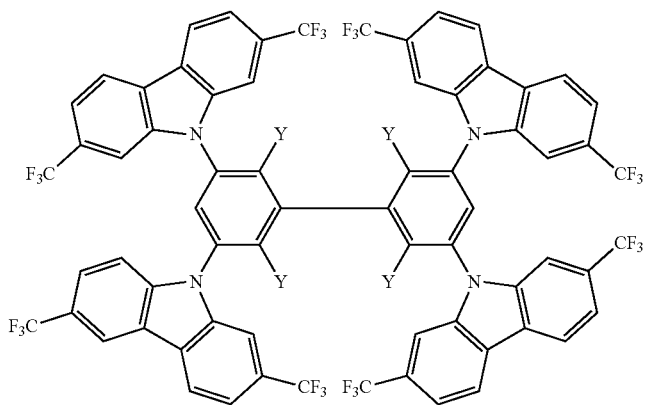
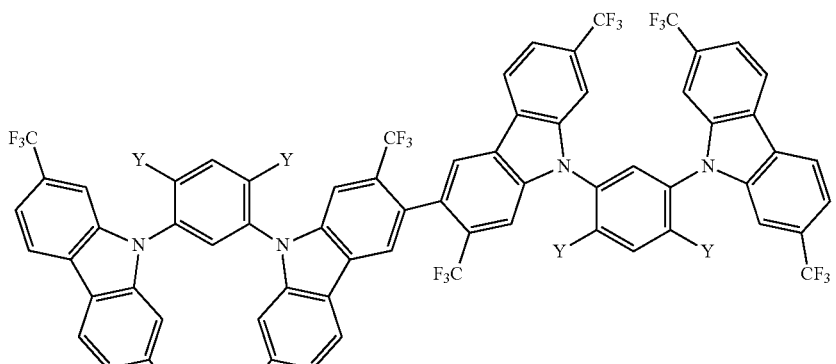
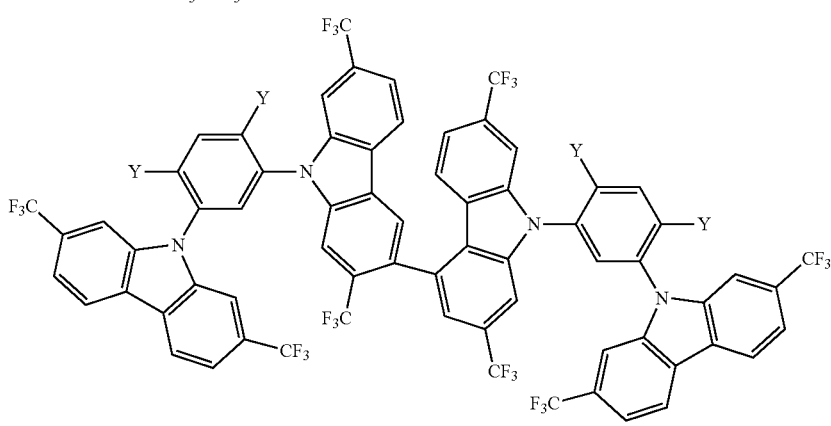
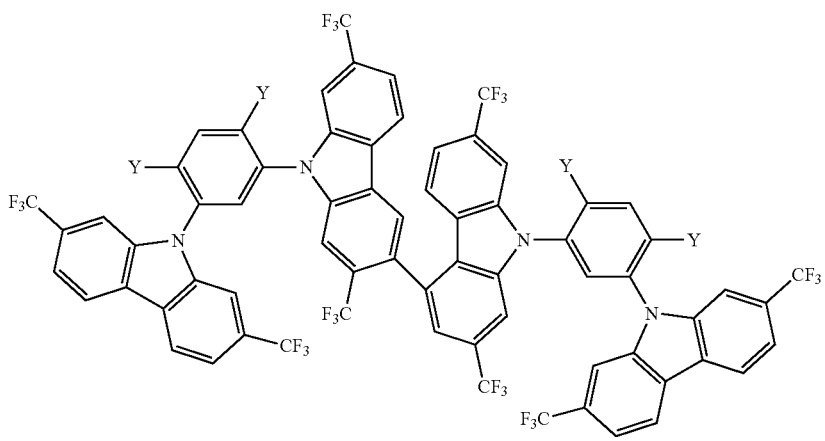

-continued
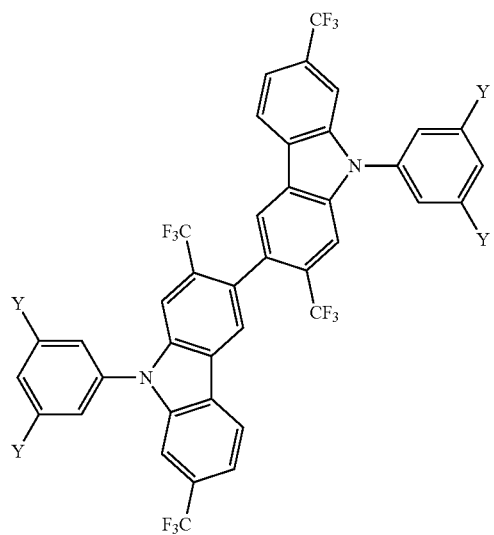
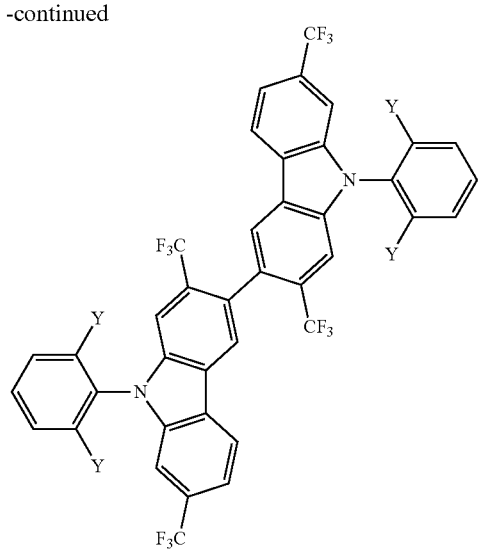
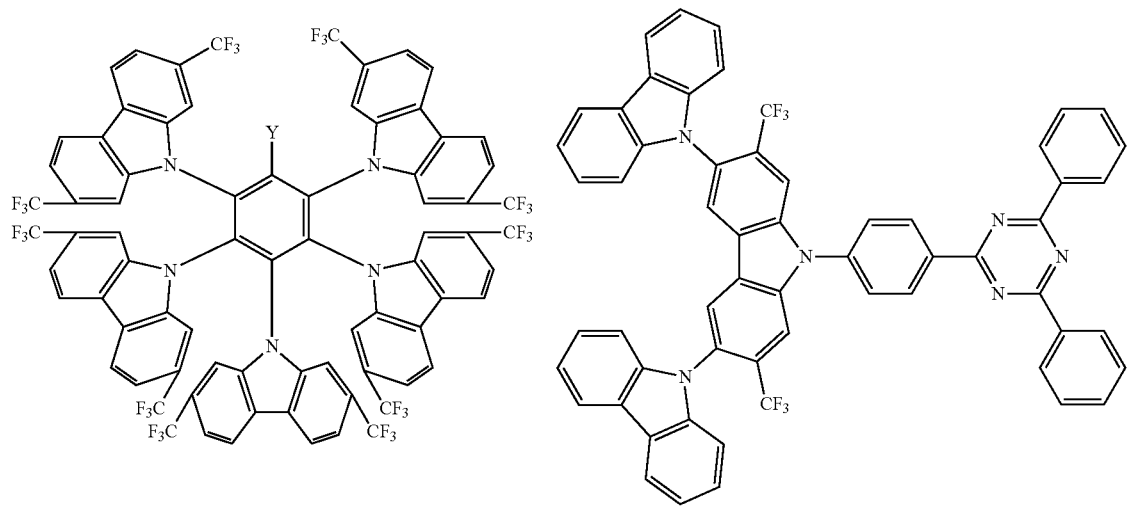
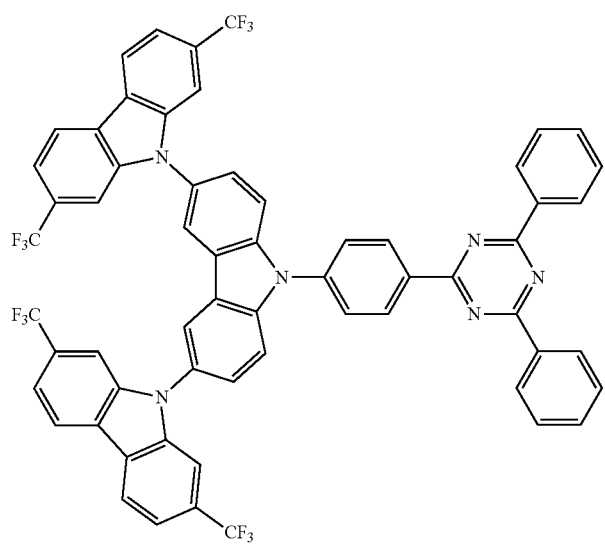

-continued
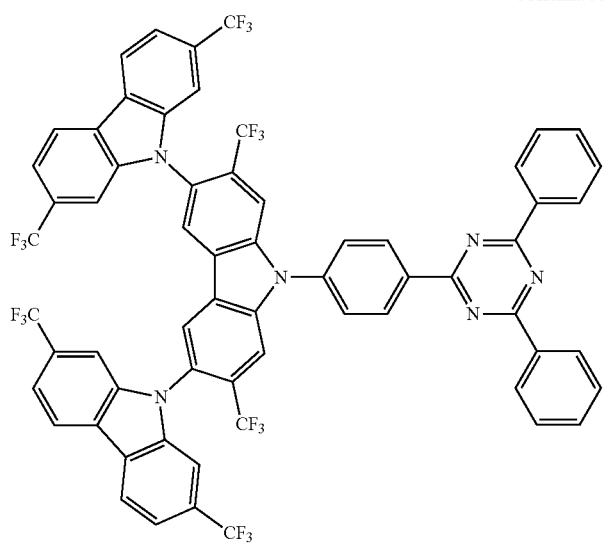
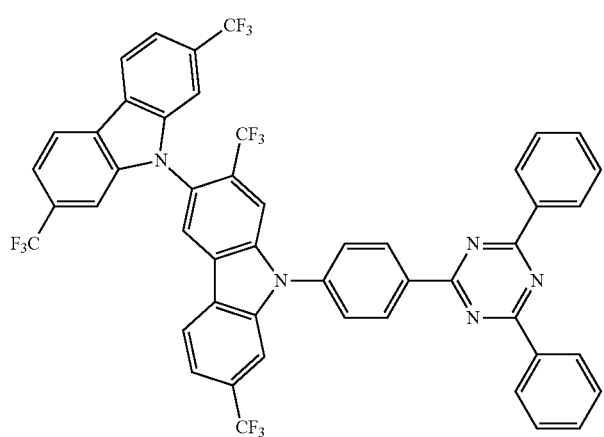
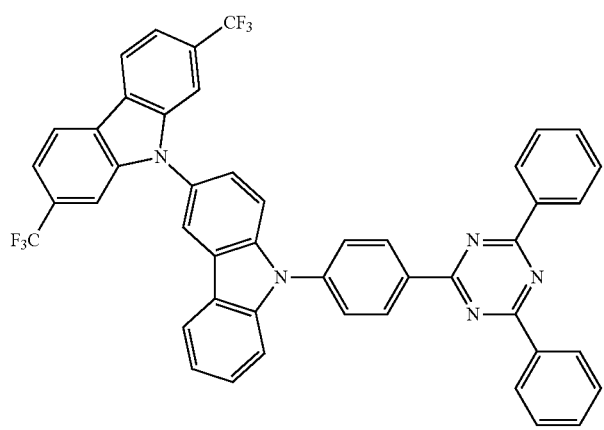

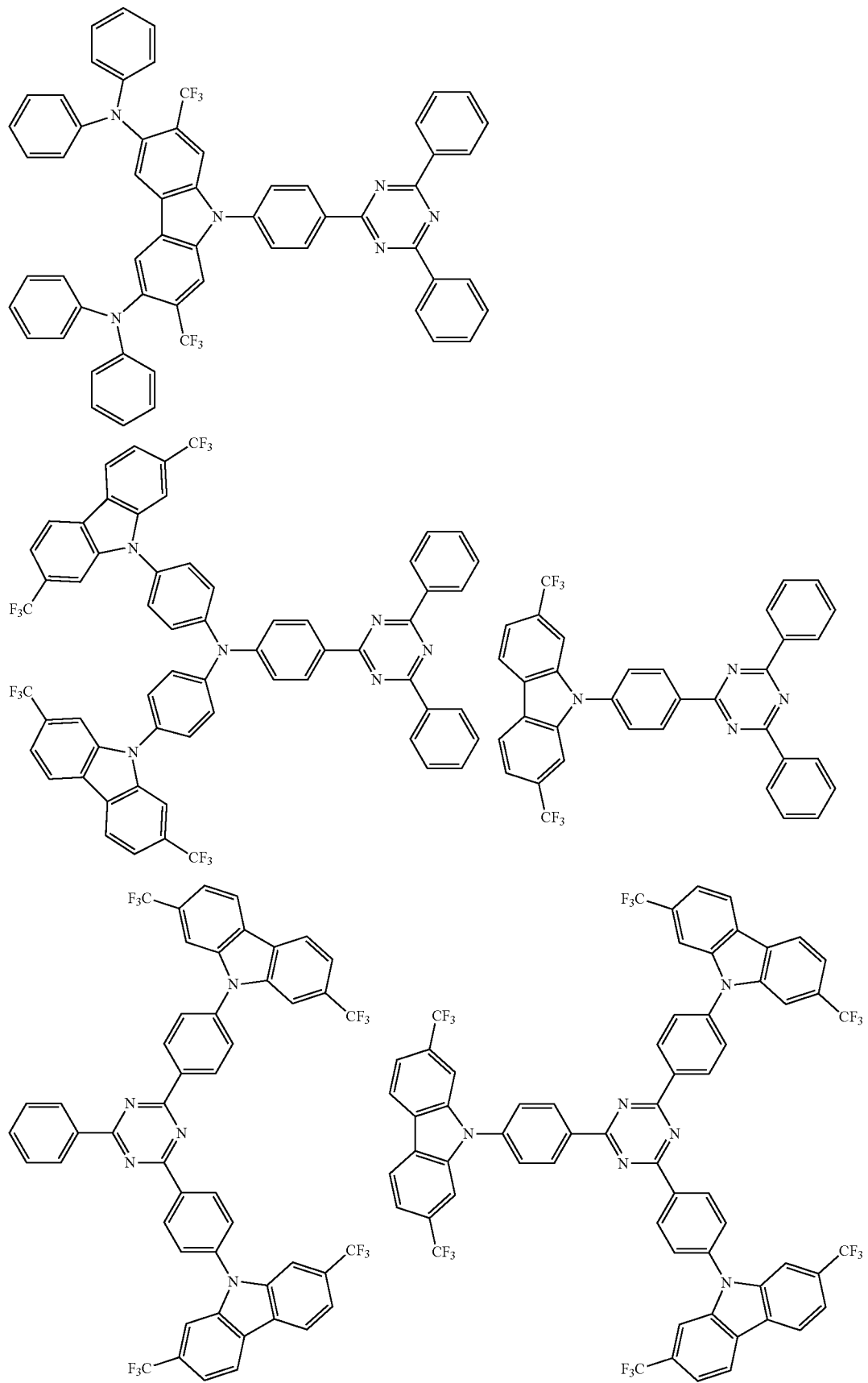

-continued
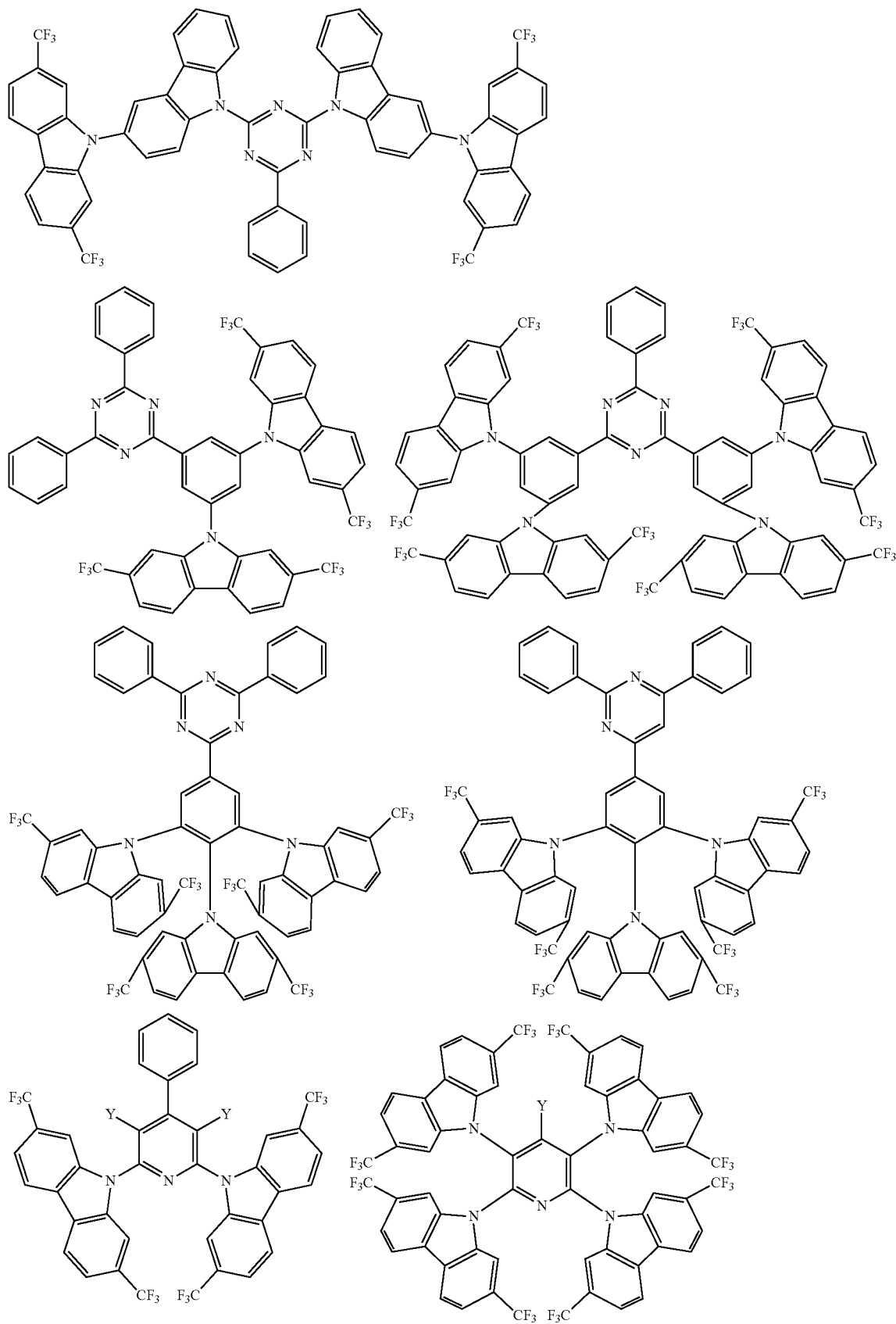

-continued
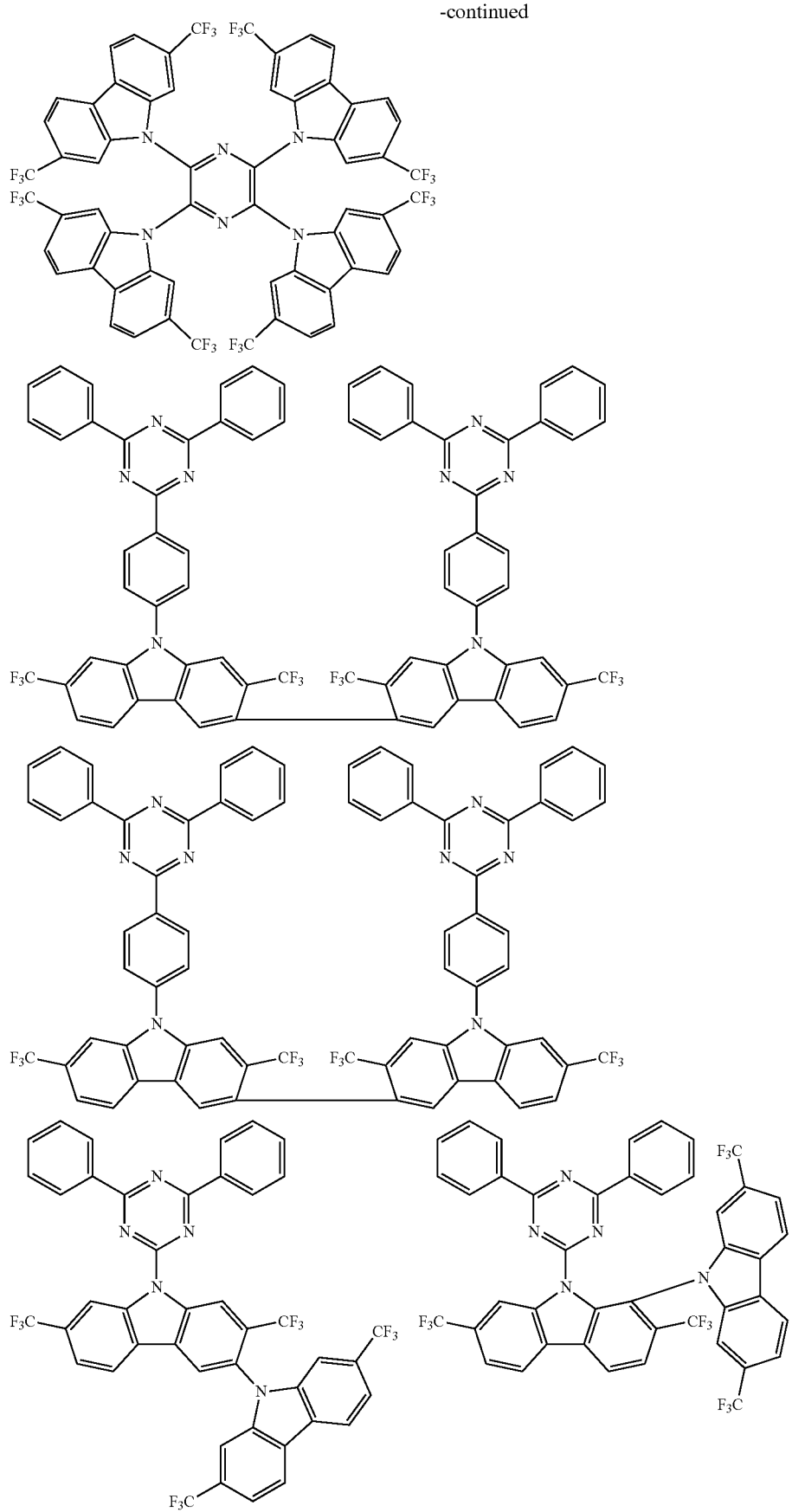

-continued
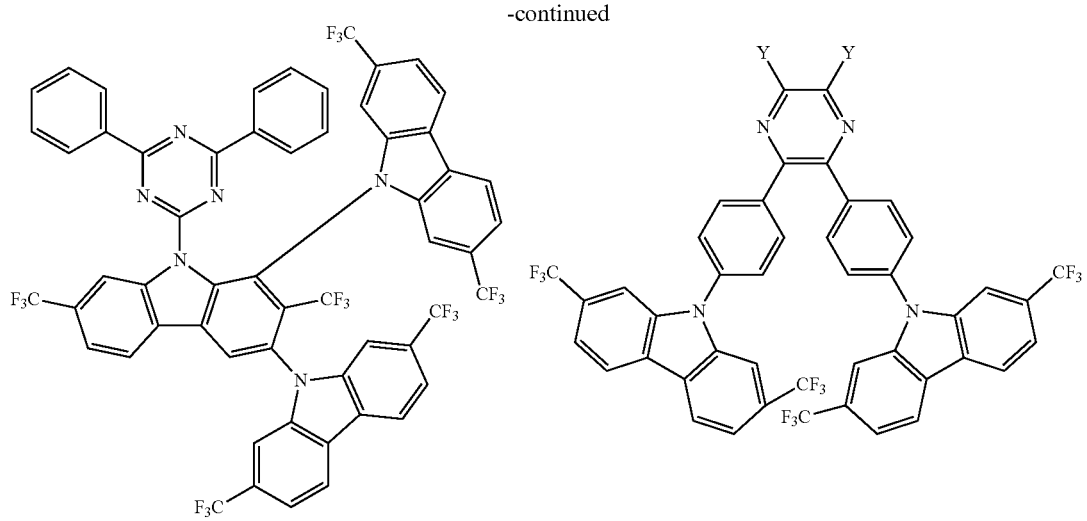
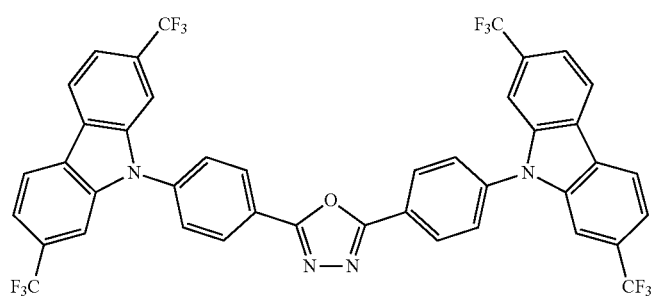
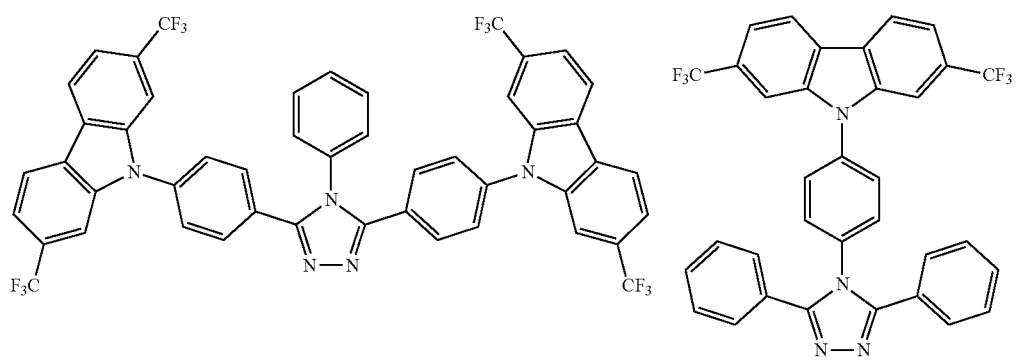
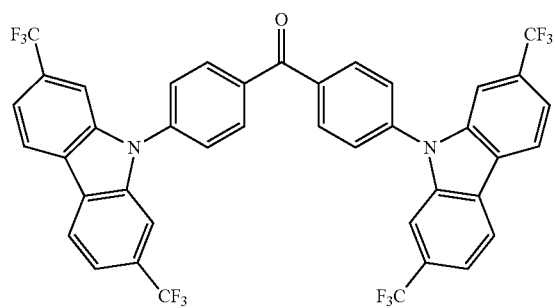

-continued
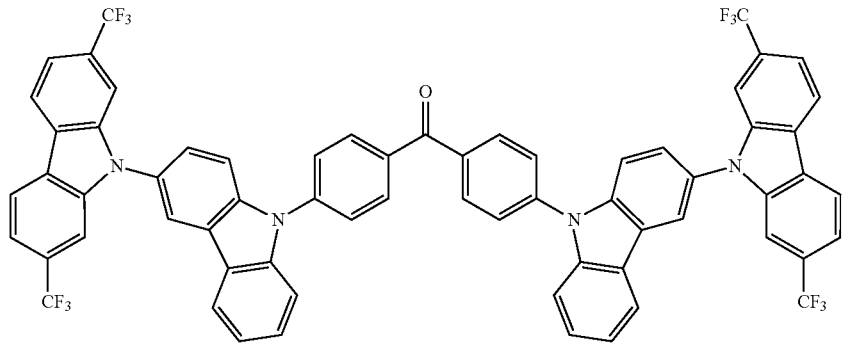
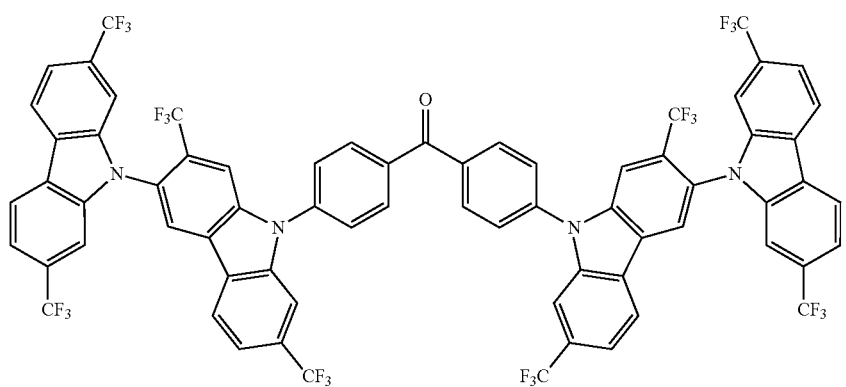
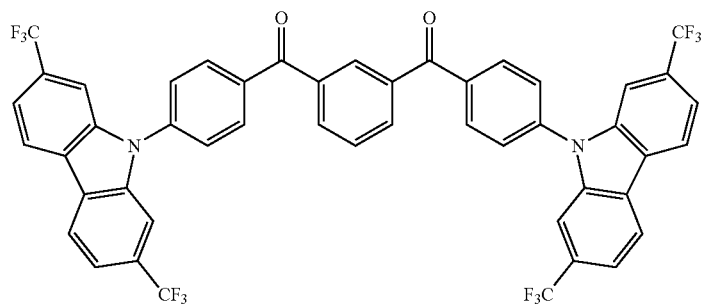
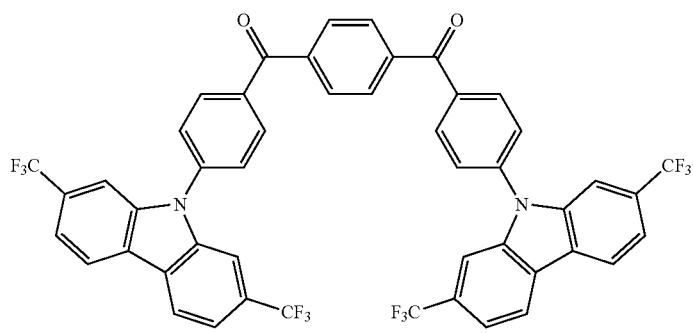

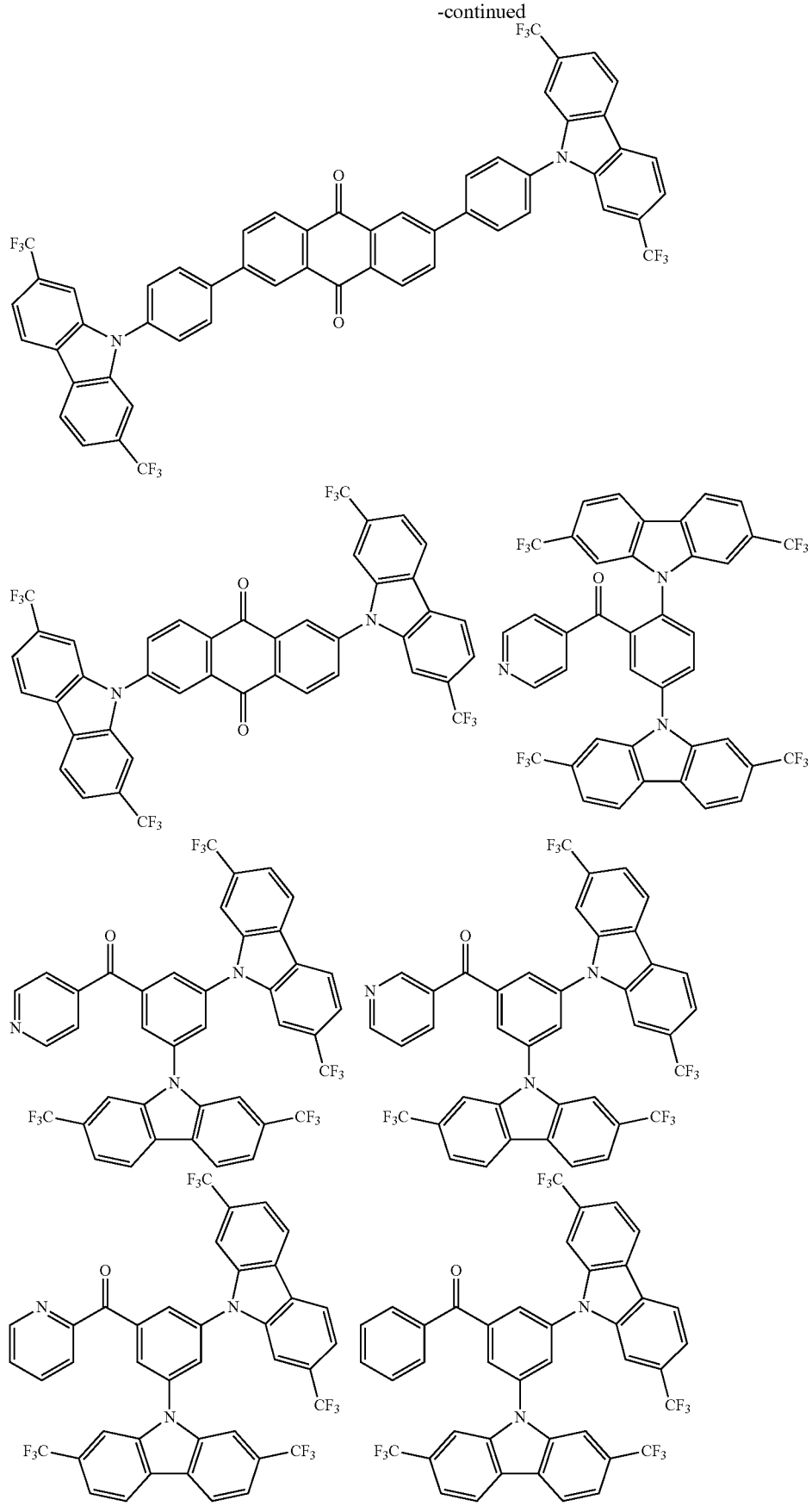

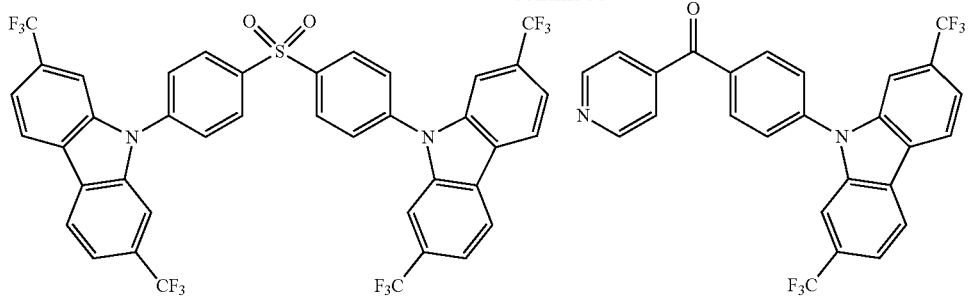
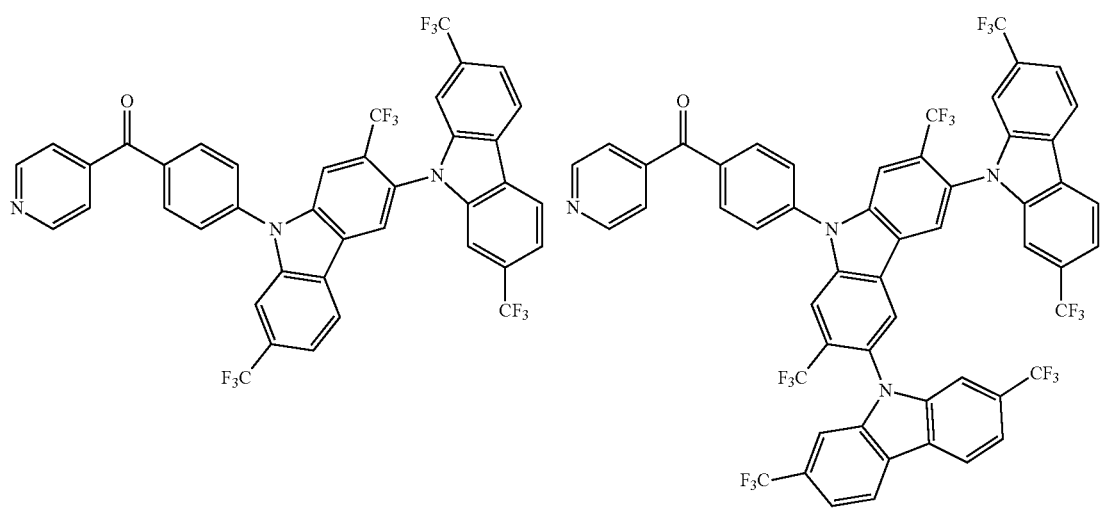
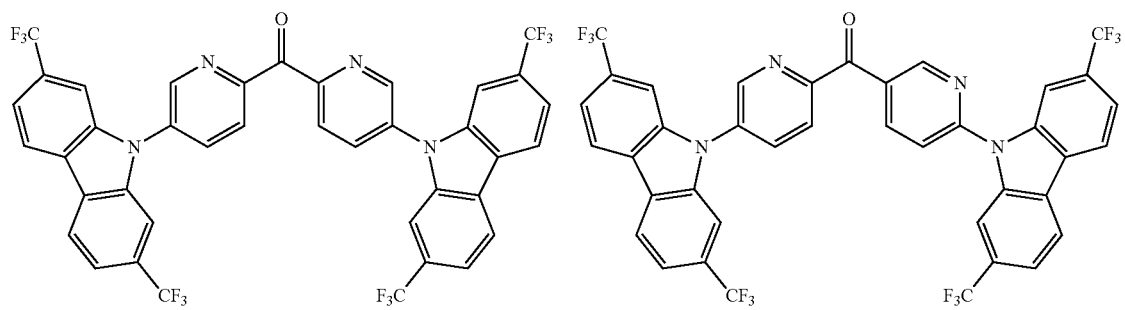
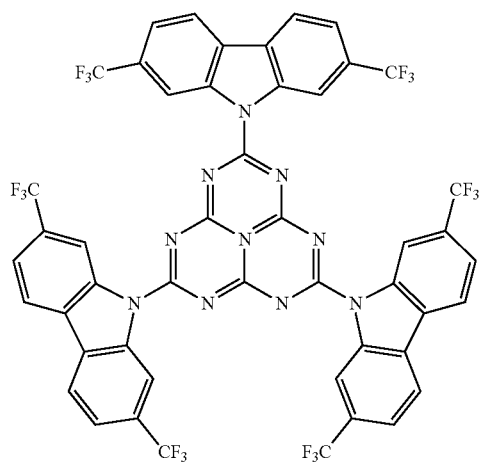

-continued
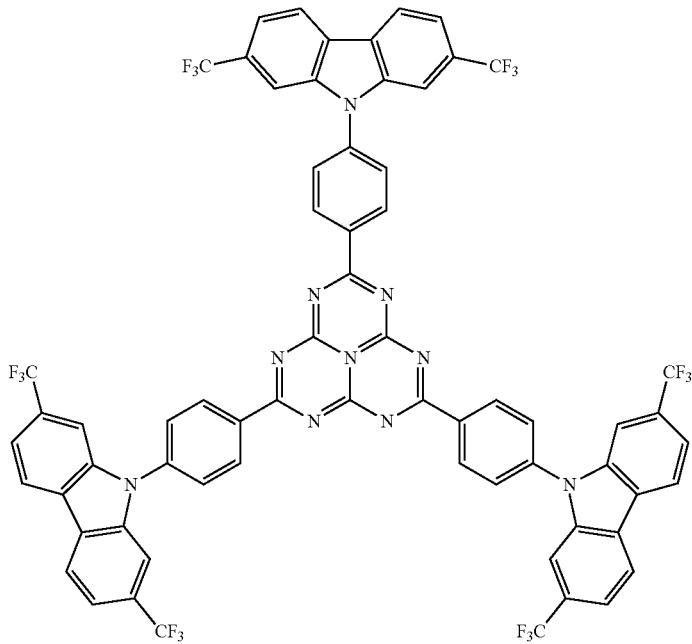
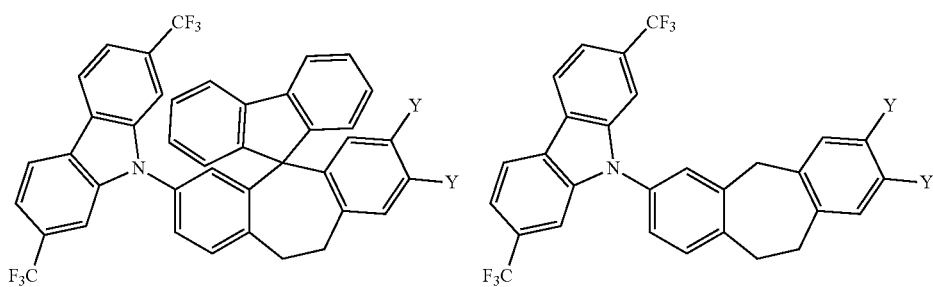
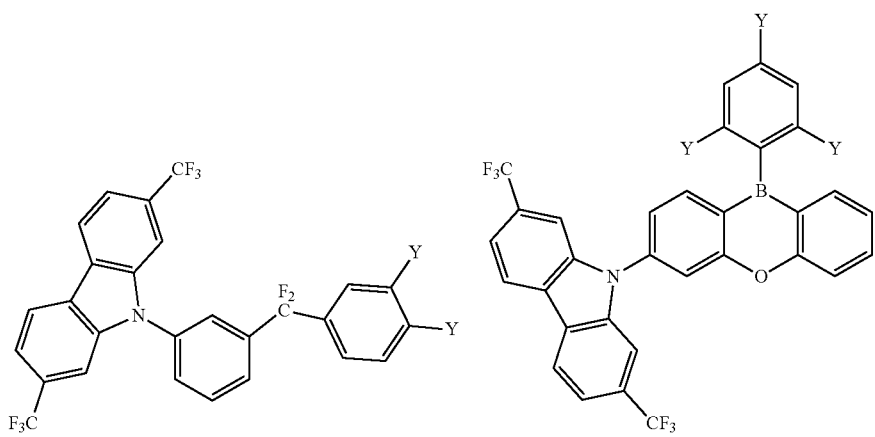

-continued
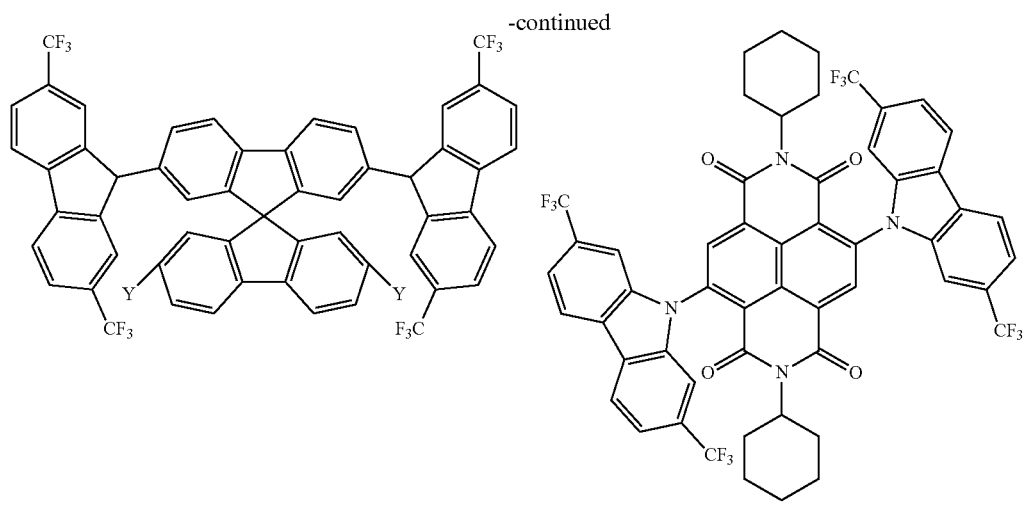
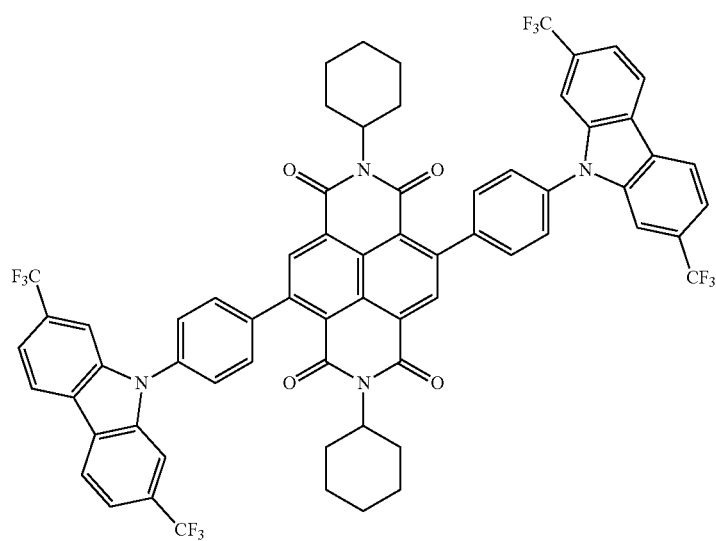
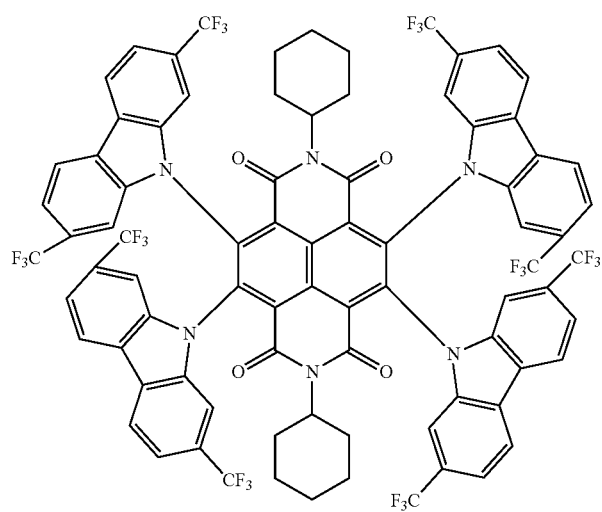

-continued
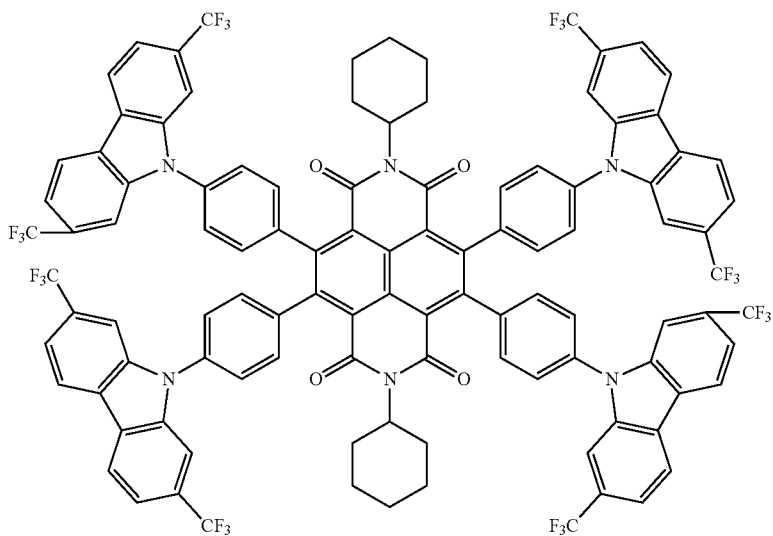
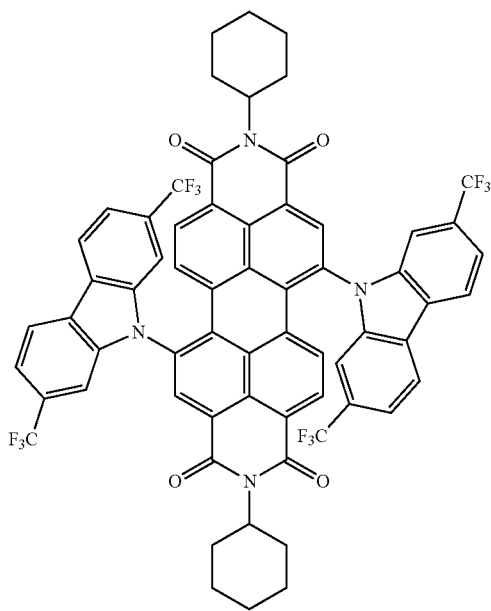

-continued
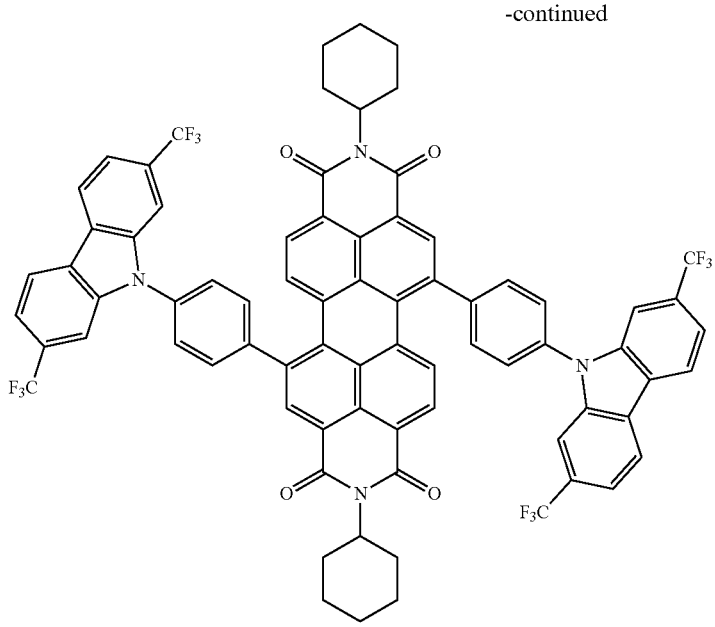
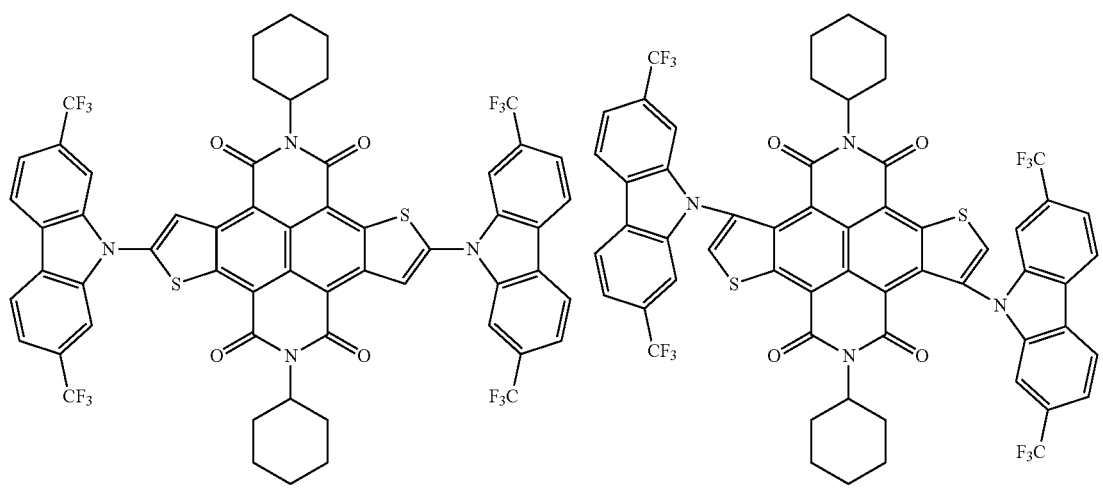
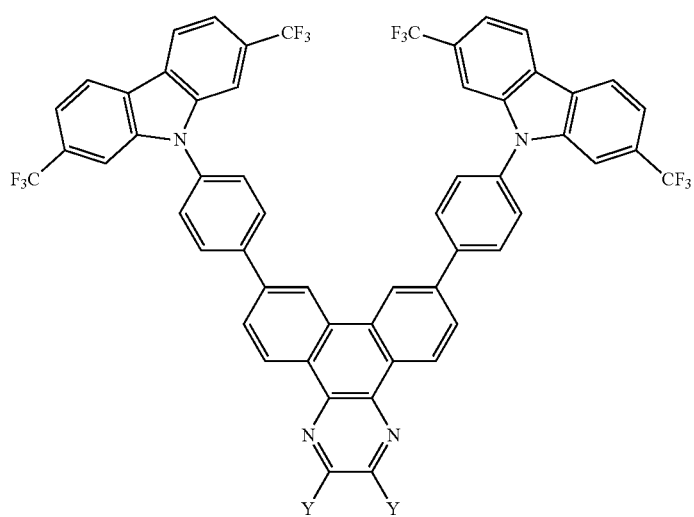

-continued
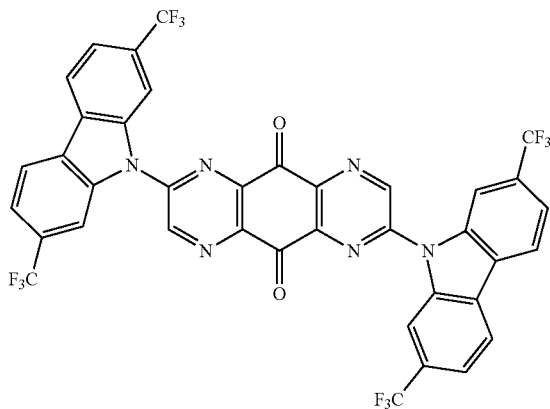
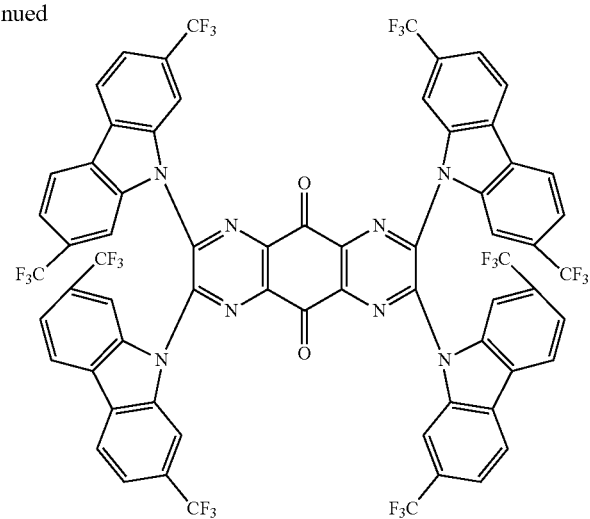
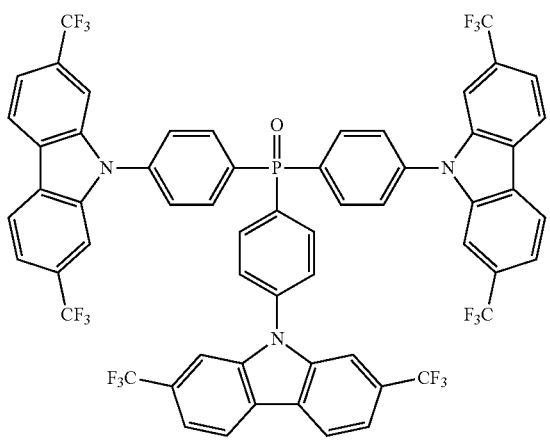
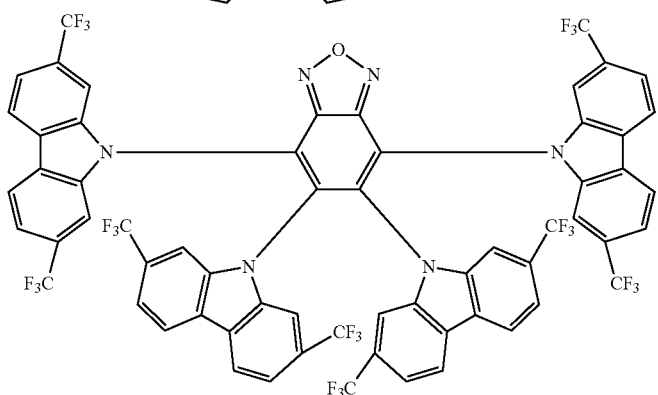
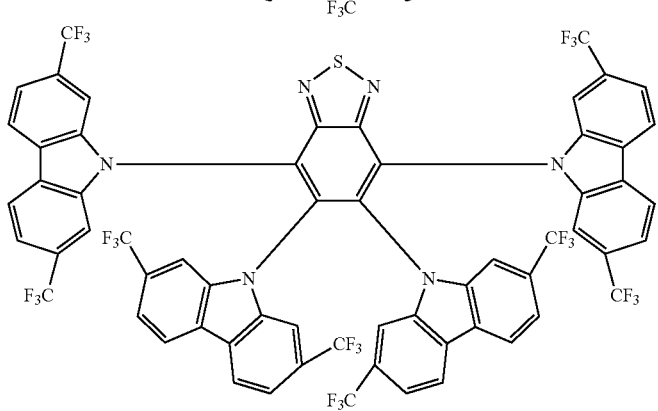

-continued

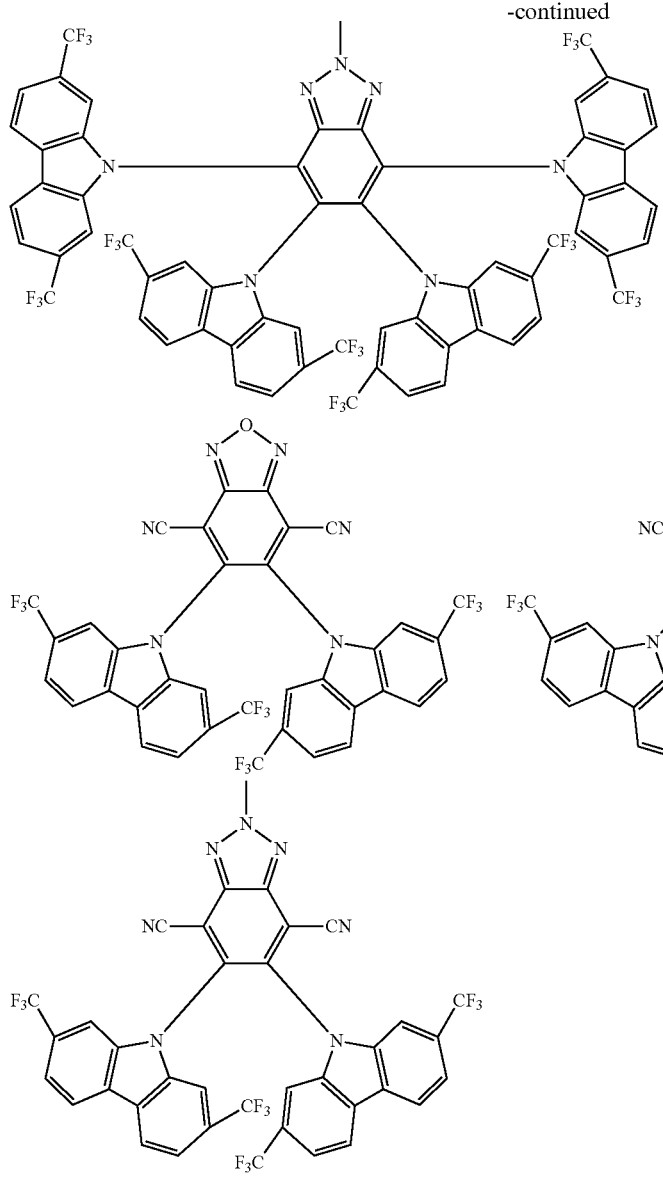
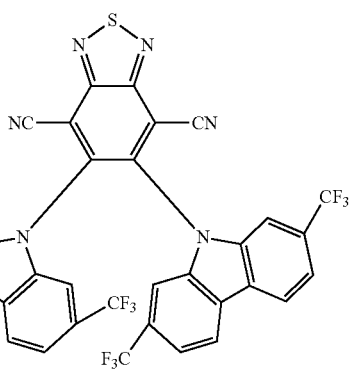
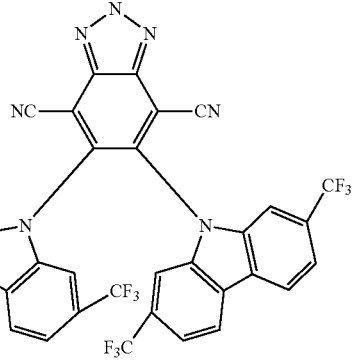

The molecular weight of the compound of the present invention is, for example, when an organic layer containing the compound of the present invention is intended to be used by forming it according to an evaporation method, preferably 2000 or less, more preferably 1650 or less. The lower limit of the molecular weight is generally 247 or more, preferably 290 or more.

Irrespective of the molecular weight thereof, the compound of the present invention may be formed into a film according to a coating method. Using a coating method, the compound having a relatively large molecular weight can be formed into a film.

Here, the compound of the present invention has a structure where a carbazol-9-yl group is substituted with a perfluoroalkyl group, and can, therefore, as compared with a case where the carbazol-9-yl group is substituted with any other substituent such as a cyano group, grow readily in a vapor phase and can dissolve in solvent. Consequently, the compound can be formed into a film of good quality according to any or a dry process of vapor deposition or a wet process of a coating method.

By application of the present invention, a compound containing a plurality of the structures that are characteristic to the compound of the present invention may be considered to be used in a light emitting layer of an organic light emitting device.

For example, a polymer produced by polymerizing a polymerizing monomer having the structure characteristic to the compound of the present invention may be considered to be used in a light emitting layer of an organic light emitting device. Specifically, it may be considered that a monomer having a polymerizing functional group in any of D and A in the formula (1) is prepared, and this is homopolymerized or is copolymerized with any other monomer to give a polymer having a recurring unit of the structure, and the resultant polymer is used in a light emitting layer of an organic light emitting device. Alternatively, it may also be considered that compounds each having the structure represented by the formula (1) are coupled to give a dimer or a trimer, and the resultant dimer or trimer is used in a light emitting layer of an organic light emitting device.

Structural examples of a recurring unit to constitute a polymer that contains the structure of represented by the formula (1) include structures having the following formula (17) or (18) in any of D and A in the formula (1).

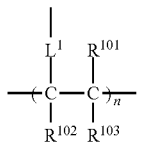

Formula (17)

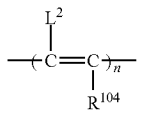

Formula (18)

In the formulae (17) and (18), $L^1$ and $L^2$ each represent a linking group. The carbon number of the liking group is preferably 0 to 20, more preferably 1 to 15, even more preferably 2 to 10. Preferably, the linking group has a structure represented by $—X^{11}-L^{11}-$. Here, $X^{11}$ represents an oxygen atom or a sulfur atom, and is preferably an oxygen atom. $L^{11}$ represents a linking group, and is preferably a substituted or unsubstituted alkylene group, or a substituted or unsubstituted arylene group, more preferably a substituted or unsubstituted alkylene group having 1 to 10 carbon atoms, or a substituted or unsubstituted phenylene group.

In the formulae (17) and (18), $R^{101}$, $R^{102}$, $R^{103}$ and $R^{104}$ each independently represent a substituent, preferably a substituted or unsubstituted alkyl group having 1 to 6 carbon atoms, a substituted or unsubstituted alkoxy group having 1 to 6 carbon atoms, or a halogen atom, more preferably an unsubstituted alkyl group having 1 to 3 carbon atoms, an unsubstituted alkoxy group having 1 to 3 carbon atoms, a fluorine atom, or a chlorine atom, and even more preferably an unsubstituted alkyl group having 1 to 3 carbon atoms or an unsubstituted alkoxy group having 1 to 3 carbon atoms.

Specific structural examples of the recurring unit include those having, as introduced into any of D and A in the formula (1), a structure represented by the following formulae (21) to (24). The number of the structures represented by the following formulae (21) to (24) to be introduced into any of D and A in the formula (1) may be 2 or more, but is preferably 1. In the following formulae (21) to (24), n represents a number of the recurring units, and the range thereof is not specifically limited.

Formula (21)

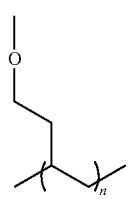

Formula (22)

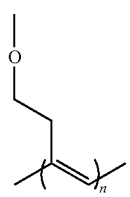

Formula (23)

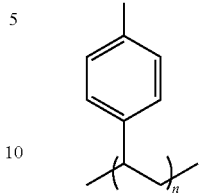

Formula (24)

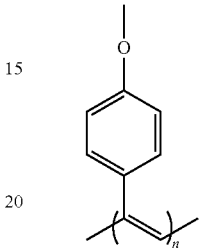

A polymer having a recurring unit containing any of these formulae (21) to (24) can be synthesized by introducing a hydroxy group into at least one of D and A in the formula (1), then reacting it, acting as a linker, with any of the following compounds to introduce a polymerizing group thereinto, and polymerizing the polymerizing group.

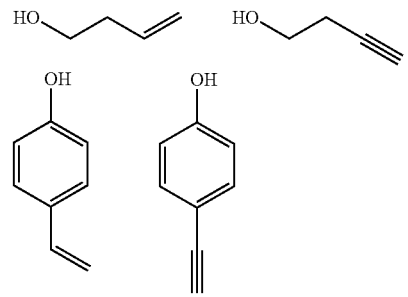

A polymer having a structure represented by the formula (1) in the molecule may be a polymer composed of a recurring unit alone having a structure represented by the formula (1), or a polymer containing a recurring unit having any other structure. The recurring unit having a structure represented by the formula (1) contained in the polymer may be of one kind alone or may also be of two or more kinds. The recurring unit not having a structure represented by the formula (1) includes those derived from monomers used in ordinary copolymerization. Examples thereof include a recurring unit derived from a monomer having an ethylenic unsaturated bond such as ethylene and styrene.

[Method for Synthesis of Compound of Invention]

The compound of the present invention mentioned hereinabove is a novel compound.

A method for synthesis of the compound of the present invention is not specifically limited. For synthesis of the compound of the present invention, known synthesis methods and conditions may be combined in any desired manner. For example, 2,7-ditrifluoromethylcarbazole and a fluoride may be coupled to synthesize the compound. Regarding concrete reaction conditions for the synthesis, Synthesis Examples to be given hereinunder may be referred to.

[Organic Light Emitting Device]

The compound of the present invention is so configured that at least a part of the carbazol-9-yl group therein and at least a part of the group having a positive Hammett constant $\sigma_p$ and, if any, the π-conjugated linking group form a π-electron conjugated system. Having such a structure, both the HOMO level and the LUMO level of the compound of the present invention are deep, and the compound is therefore considered to be prevented from being deteriorated by reaction between the radical species and the excitons formed in the light emission process with moisture and oxygen. In particular, the substituting positions of the perfluoroalkyl group in the carbazol-9-yl group in the compound are 2-position and 7-position, and therefore as compared with a case not having a perfluoroalkyl group or a case where the substituting positions of the perfluoroalkyl group are 3-position and 6-positions, the compound can realize a remarkably high emission efficiency and can emit light having a narrow full width at half maximum in the emission spectrum and having a high color purity. The reason why the compound represented by the formula (1) can realize such excellent emission characteristics is considered to be because the difference $\Delta E_{ST}$ between the excited singlet energy level $E_{S1}$ and the excited triplet energy level $E_{T1}$ thereof may be small, and the vibrational relaxation (radiationless deactivation) thereof after the compound has been in an excited state may be small.

Specifically, as shown in Examples given hereinunder, the compound 1 where the carbazol-9-yl group is substituted with a perfluoroalkyl group at the 2-position and the 7-position has a smaller $\Delta E_{ST}$ than the comparative compound 2 where the carbazol-9-yl group is substituted with perfluoroalkyl group at the 3-position and the 6-position, and the delayed fluorescent lifetime T2 of the former is longer (see Tables 1 and 3). The compound having such characteristics undergoes reverse intersystem crossing from the excited triplet state to the excited singlet state at a high possibility, and accordingly it may be presumed that the energy loss owing to radiationless deactivation from the excited triplet state of the compound can be suppressed. Consequently, it is considered that the excited triplet energy can be efficiently converted into the excited singlet energy and can be effectively utilized for fluorescence emission (delayed fluorescence emission) to attain a high emission efficiency. In addition, it is considered that the vibrational relaxation of the compound in which the carbazol-9-yl group is substituted with a perfluoroalkyl group at the 2-position and the 7-position may be small as compared with that of the compound in which the carbazol-9-yl group is substituted with a perfluoroalkyl group at the 3-position and the 6-position, and the former compound may undergo radiative deactivation from a higher excited singlet energy level relative to the ground level thereof. Consequently, it is considered that the emission spectrum of the compound of the present invention can be prevented from broadening and the compound can emit high-energy light (short-wavelength light).

As in the above, the compound of the present invention has good emission characteristics and has high lightfastness. Accordingly, the compound of the present invention is useful as a light emitting material or a host material for organic light emitting devices, and can be effectively used as a material for a light emitting layer of organic light emitting devices.

Further, the compound of the present invention includes a delayed fluorescent material (delayed fluorescent substance) that emits fluorescence (delayed fluorescence) via the above-mentioned reverse intersystem crossing along with ordinary fluorescence. Specifically, the present invention includes an aspect of an invention of a delayed fluorescent material having the structure characteristic to the present invention, an aspect of an invention of using the compound of the present invention as a delayed fluorescent material, and an aspect of an invention of a method of emitting delayed fluorescence using the compound of the present invention. An organic light emitting device using the compound as a light emitting material emits delayed fluorescence at a high emission efficiency. The principle of the device is described below with reference to an organic electroluminescent device as an example thereof.

In an organic electroluminescent device, a carrier is injected into a light emitting material from both the positive and negative electrodes to form a light emitting material in an excited state, and the material emits light. In general, in the case of a carrier-injection organic electroluminescent device, 25% of the formed excitons are excited to be in an excited singlet state, and the remaining 75% are excited in an excite triplet state. Accordingly, using phosphorescence that is emission from an excited triplet state enables higher energy utilization efficiency. However, the excited triplet state has a long lifetime, and may therefore cause energy deactivation owing to saturation of the excited state or interaction with excitons in an excited triplet state and is, therefore, in general, the quantum yield of phosphorescence is not high in many cases. On the other hand, a delayed fluorescent material may, after having undergone energy transition from the excited triplet state owing to intersystem crossing, emit fluorescence through reverse intersystem crossing into the excited singlet state owing to triplet-triplet annihilation or thermal energy absorption. In an organic electroluminescent device, above all, a thermal activation-type delayed fluorescent material that may be activated through thermal energy absorption is considered to be especially useful. In the case where a delayed fluorescent material is used in an organic electroluminescent device, the excitons in an excited singlet state emit fluorescence in an ordinary manner. On the other hand, the excitons in an excited triplet state emit fluorescence through intersystem crossing into an excited singlet state by absorbing the heat generated by the device. At this time, the emission is from the excited singlet state, and therefore although the wavelength of the emitted light is the same as that of fluorescence, the lifetime (emission lifetime) of the light resulting from reverse intersystem crossing from the excited triplet state to the excited singlet state is long than that of ordinary fluorescence or phosphorescence, and consequently, the light is observed as delayed fluorescence that is later than ordinary fluorescence. This may be defined as delayed fluorescence. Using the thermal activation-type exciton transfer mechanism of the type, the proportion of the compound in an excited singlet state, which forms only 25% in an ordinary manner, could be increased up to more than 25% via the thermal energy absorption after carrier injection. When a compound capable of emitting strong fluorescence and delayed fluorescence even at a low temperature lower than 100° C. is used in a device, sufficient intersystem crossing from an excited triplet state to an excited singlet state may occur owing to the heat of the device, thereby markedly improving the emission efficiency of the device.

Using the compound of the present invention as a light emitting material in a light emitting layer, there can be provided excellent organic light emitting devices such as organic photoluminescent devices (organic PL devices) and organic electroluminescent devices (organic EL devices). An organic photoluminescent device has a structure having at least a light emitting layer formed on a substrate. An organic electroluminescent device has a structure having at least an anode, a cathode and an organic layer formed between the anode and the cathode. The organic layer contains at least a light emitting layer, and may be formed of a light emitting layer alone, or may have one or more other organic layers than the light emitting layer. Such other organic layers include a hole transport layer, a hole injection layer, an electron blocking layer, a hole blocking layer, an electron injection layer, an electron transport layer, and an exciton blocking layer. The hole transport layer may be a hole injection transport layer having a hole injection function, and the electron transport layer may be an electron injection transport layer having an electron injection function. The organic electroluminescent device may be a bottom emission type of taking the light generated in the light emitting layer outside through the side of the substrate, or may be a top emission type of taking the light generated in the light emitting layer outside through the opposite side of the substrate. In any type, the electrode to be formed on the substrate side may be an anode or a cathode. The electrode on the side through which light is taken out is required to be transparent, but the electrode on the opposite side is not always required to be transparent. A specific example of a structure of an organic electroluminescent device is shown in FIG. 1. In FIG. 1, 1 is a substrate, 2 is an anode, 3 is a hole injection layer, 4 is a hole transport layer, 5 is a light emitting layer, 6 is an electron transport layer, and 7 is a cathode.

In the following, the members and the layers of the organic electroluminescent device are described. The description of the substrate and the light emitting layer may apply also to that of the substrate and the light emitting layer of an organic photoluminescent device.

(Substrate)

Preferably, the organic electroluminescent device of the present invention is supported by a substrate. With no specific limitation, the substrate may be any one generally used in already existing organic electroluminescent devices, and for example, those formed of glass, transparent plastics, quartz or silicon may be used here.

(Anode)

The anode of the organic electroluminescent device used is preferably formed of as an electrode material a metal, an alloy or an electroconductive compound each having a large work function (4 eV or more), or a mixture thereof. Specific examples of the electrode material include a metal, such as Au, and an electroconductive transparent material, such as CuI, indium tin oxide (ITO), $SnO_2$ and ZnO. A material that is amorphous and is capable of forming a transparent electroconductive film, such as IDIXO ($In_2O_3$—ZnO), may also be used. The anode may be formed in such a manner that the electrode material is formed into a thin film by such a method as vapor deposition or sputtering, and the film is patterned into a desired pattern by a photolithography method, or in the case where the pattern may not require high accuracy (for example, approximately 100 μm or more), the pattern may be formed with a mask having a desired shape on vapor deposition or sputtering of the electrode material. In alternative, in the case where a material capable of being applied as a coating, such as an organic electroconductive compound, is used, a wet film forming method, such as a printing method and a coating method, may be used. In the case where emitted light is to be taken out through the anode, the anode preferably has a transmittance of more than 10%, and the anode preferably has a sheet resistance of several hundred Ohm per square or less. The thickness thereof may be generally selected from a range of from 10 to 1,000 nm, and preferably from 10 to 200 nm, while depending on the material used.

(Cathode)

The cathode is preferably formed of as an electrode material a metal having a small work function (4 eV or less) (referred to as an electron injection metal), an alloy or an electroconductive compound each having a small work function (4 eV or less), or a mixture thereof. Specific examples of the electrode material include sodium, a sodium-potassium alloy, magnesium, lithium, a magnesium-cupper mixture, a magnesium-silver mixture, a magnesium-aluminum mixture, a magnesium-indium mixture, an aluminum-aluminum oxide ($Al_2O_3$) mixture, indium, a lithium-aluminum mixture, and a rare earth metal. Among these, a mixture of an electron injection metal and a second metal that is a stable metal having a larger work function than the electron injection metal, for example, a magnesium-silver mixture, a magnesium-aluminum mixture, a magnesium-indium mixture, an aluminum-aluminum oxide ($Al_2O_3$) mixture, a lithium-aluminum mixture, and aluminum, are preferred from the standpoint of the electron injection property and the durability against oxidation and the like. However, the compound represented by the formula (1) often has an extremely deep LUMO level, and therefore a metal having a large work function and is stable in air may be used. Concretely, gold or silver may be used. The cathode may be produced by forming the electrode material into a thin film by such a method as vapor deposition or sputtering. The cathode preferably has a sheet resistance of several hundred Ohm per square or less, and the thickness thereof may be generally selected from a range of from 10 nm to 5 μm, and preferably from 50 to 200 nm. For transmitting the emitted light, any one of the anode and the cathode of the organic electroluminescent device is preferably transparent or translucent, thereby enhancing the light emission luminance.

The cathode may be formed with the electroconductive transparent materials described for the anode, thereby forming a transparent or translucent cathode, and by applying the cathode, a device having an anode and a cathode, both of which have transmittance, may be produced.

(Light Emitting Layer)

The light emitting layer is a layer in which holes and electrons injected from an anode and a cathode are recombined to give excitons for light emission. A light emitting material may be used alone in the light emitting layer, but preferably, the light emitting layer contains a light emitting material and a host material. As the light emitting material, one or more selected from the compound group of the present invention may be used. In order that the organic electroluminescent device and the organic photoluminescent device of the present invention can express a high emission efficiency, it is important to confine the singlet excitons and the triplet excitons formed in the light emitting material inside the light emitting material. Accordingly, a host material is preferably used in addition to the light emitting material in the light emitting layer. The host material may be such an organic compound that at least any one of the excited singlet energy and the excited triplet energy thereof is higher than that of the light emitting material in the present invention. As a result, the single excitons and the triplet excitons formed in the light emitting material in the present invention can be confined inside the molecules of the light emitting material in the present invention and therefore the emission efficiency of the light emitting material can be sufficiently drawn forth. Needless-to-say, even though the single excitons and the triplet excitons could not be sufficiently confined, a high emission efficiency could be attained as the case may be, and therefore a host material capable of realizing a high emission efficiency can be used in the present invention with no specific limitation. In the organic light emitting device or the organic electroluminescent device of the present invention, light emission occurs from the light emitting material of the present invention contained in the light emitting layer. The light emission includes both fluorescence emission and delayed fluorescence emission. However, the light emission may also be partly from a host material.

In the case where a host material is used, the content of the compound of the present invention that is a light emitting material in the light emitting layer is preferably 0.1% by weight or more, more preferably 1% by weight or more, and is preferably 50% by weight or less, more preferably 20% by weight or less, even more preferably 10% by weight or less.

The host material in the light emitting layer is preferably an organic compound having hole transporting performance and electron transporting performance, capable of preventing prolongation of the wavelength of light emission and having a high glass transition temperature.

(Injection Layer)

The injection layer is a layer that is provided between the electrode and the organic layer, for decreasing the driving voltage and enhancing the light emission luminance, and includes a hole injection layer and an electron injection layer, which may be provided between the anode and the light-emitting layer or the hole transport layer and between the cathode and the electron transport layer. The injection layer may be provided depending on necessity.

(Blocking Layer)

The blocking layer is a layer that is capable of inhibiting charges (electrons or holes) and/or excitons present in the light-emitting layer from being diffused outside the light-emitting layer. The electron blocking layer may be disposed between the light-emitting layer and the hole transport layer, and inhibits electrons from passing through the light-emitting layer toward the hole transport layer. Similarly, the hole blocking layer may be disposed between the light-emitting layer and the electron transport layer, and inhibits holes from passing through the light-emitting layer toward the electron transport layer. The blocking layer may also be used for inhibiting excitons from being diffused outside the light-emitting layer. Thus, the electron blocking layer and the hole blocking layer each may also have a function as an exciton blocking layer. The term "the electron blocking layer" or "the exciton blocking layer" referred to herein is intended to include a layer that has both the functions of an electron blocking layer and an exciton blocking layer by one layer.

(Hole Blocking Layer)

The hole blocking layer has the function of an electron transport layer in a broad sense. The hole blocking layer has a function of inhibiting holes from reaching the electron transport layer while transporting electrons, and thereby enhances the recombination probability of electrons and holes in the light-emitting layer. As the material for the hole blocking layer, the material for the electron transport layer to be mentioned below may be used optionally.

(Electron Blocking Layer)

The electron blocking layer has the function of transporting holes in a broad sense. The electron blocking layer has a function of inhibiting electrons from reaching the hole transport layer while transporting holes, and thereby enhances the recombination probability of electrons and holes in the light-emitting layer.

(Exciton Blocking Layer)

The exciton blocking layer is a layer for inhibiting excitons generated through recombination of holes and electrons in the light-emitting layer from being diffused to the charge transporting layer, and the use of the layer inserted enables effective confinement of excitons in the light-emitting layer, and thereby enhances the light emission efficiency of the device. The exciton blocking layer may be inserted adjacent to the light-emitting layer on any of the side of the anode and the side of the cathode, and on both the sides. Specifically, in the case where the exciton blocking layer is present on the side of the anode, the layer may be inserted between the hole transport layer and the light-emitting layer and adjacent to the light-emitting layer, and in the case where the layer is inserted on the side of the cathode, the layer may be inserted between the light-emitting layer and the cathode and adjacent to the light-emitting layer. Between the anode and the exciton blocking layer that is adjacent to the light-emitting layer on the side of the anode, a hole injection layer, an electron blocking layer and the like may be provided, and between the cathode and the exciton blocking layer that is adjacent to the light-emitting layer on the side of the cathode, an electron injection layer, an electron transport layer, a hole blocking layer and the like may be provided. In the case where the blocking layer is provided, preferably, at least one of the excited singlet energy and the higher than the excited singlet energy and the excited triplet energy of the light-emitting layer, respectively, of the light-emitting material.

(Hole Transport Layer)

The hole transport layer is formed of a hole transport material having a function of transporting holes, and the hole transport layer may be provided as a single layer or plural layers.

The hole transport material has one of injection or transporting property of holes and blocking property of electrons, and may be any of an organic material and an inorganic material. Examples of known hole transport materials that may be used herein include a triazole derivative, an oxadiazole derivative, an imidazole derivative, a carbazole derivative, an indolocarbazole derivative, a polyarylalkane derivative, a pyrazoline derivative, a pyrazolone derivative, a phenylenediamine derivative, an arylamine derivative, an amino-substituted chalcone derivative, an oxazole derivative, a styrylanthracene derivative, a fluorenone derivative, a hydrazone derivative, a stilbene derivative, a silazane derivative, an aniline copolymer and an electroconductive polymer oligomer, particularly a thiophene oligomer. Among these, a porphyrin compound, an aromatic tertiary amine compound and a styrylamine compound are preferably used, and an aromatic tertiary amine compound is more preferably used. In addition, inorganic semiconductor such as molybdenum oxide may also be used as the hole transport material.

(Electron Transport Layer)

The electron transport layer is formed of a material having a function of transporting electrons, and the electron transport layer may be a single layer or may be formed of plural layers.

The electron transport material (often also acting as a hole blocking material) may have a function of transmitting the electrons injected from a cathode to a light-emitting layer. The electron transport layer usable here includes, for example, nitro-substituted fluorene derivatives, diphenylquinone derivatives, thiopyran dioxide derivatives, carbodiimides, fluorenylidenemethane derivatives, anthraquinodimethane and anthrone derivatives, oxadiazole derivatives, etc. Further, thiadiazole derivatives derived from the above-mentioned oxadiazole derivatives by substituting the oxygen atom in the oxadiazole ring with a sulfur atom, and quinoxaline derivatives having a quinoxaline ring known as an electron-attractive group are also usable as the electron transport material. Further, polymer materials prepared by introducing these materials into the polymer chain, or having these material in the polymer main chain are also usable. In addition, inorganic semiconductors such as zinc oxide may also be used as the electron transport material.

In producing the organic electroluminescent device, the compound of the present invention may be used not only in the light emitting layer but also in any other layer than the light emitting layer. In so doing, the compound of the present invention used in the light emitting layer and the compound of the invention used in any other layer than the light emitting layer may be the same or different. For example, the compound of the present invention may be used in the above-mentioned injection layer, the blocking layer, the hole blocking layer, the electron blocking layer, the exciton blocking layer, the hole transport layer, and the electron transport layer. The method for forming these layers is not specifically limited, and the layers may be formed according to any of a dry process or a wet process.

Preferred materials for use for the organic electroluminescent device are concretely exemplified below. However, the materials for use in the present invention are not limitatively interpreted by the following exemplary compounds. Compounds, even though exemplified as materials having a specific function, can also be used as other materials having any other function. R, R', $R_1$ to $R_{10}$ in the structural formulae of the following exemplary compounds each independently represent a hydrogen atom or a substituent. X represent a carbon atom or a hetero atom to form the ring skeleton, n represents an integer of 3 to 5, Y represents a substituent, and m represents an integer of 0 or more.

First, compounds preferred for use as the host material in the light emitting layer are shown below. In order to make the compounds compatible with the HOMO/LUMO level of the light emitting material to be used, a substituent may be adequately introduced into the backbone skeleton of the compounds exemplified below to thereby control the HOMO/LUMO level of the resultant host materials. For example, a cyano group or a perfluoroalkyl group may be introduced into the backbone skeleton of the compounds exemplified below to give compounds having a deepened HOMO/LUMO level, and the resultant compounds may be sued as a host material or a peripheral compound. The host material may be bipolar (capable of well leading both holes and electrons) or unipolar, but preferably has a higher excited triplet energy level $E_{T1}$ than the light emitting material. More preferably, the host material is bipolar and has a higher excited triplet energy level $E_{T1}$ than the light emitting material.

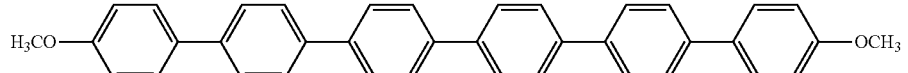
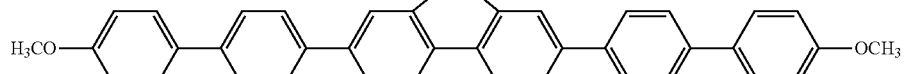

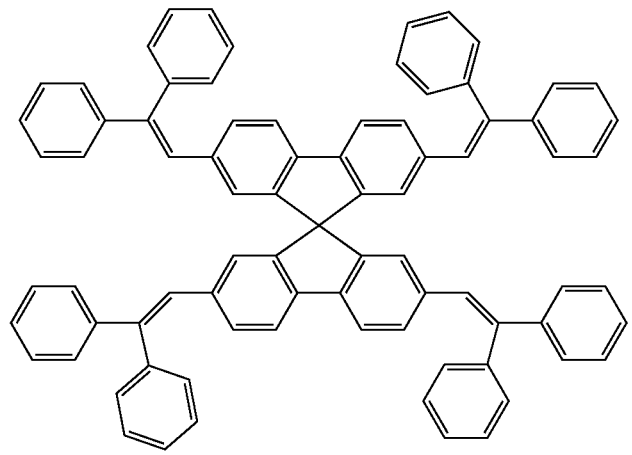

-continued
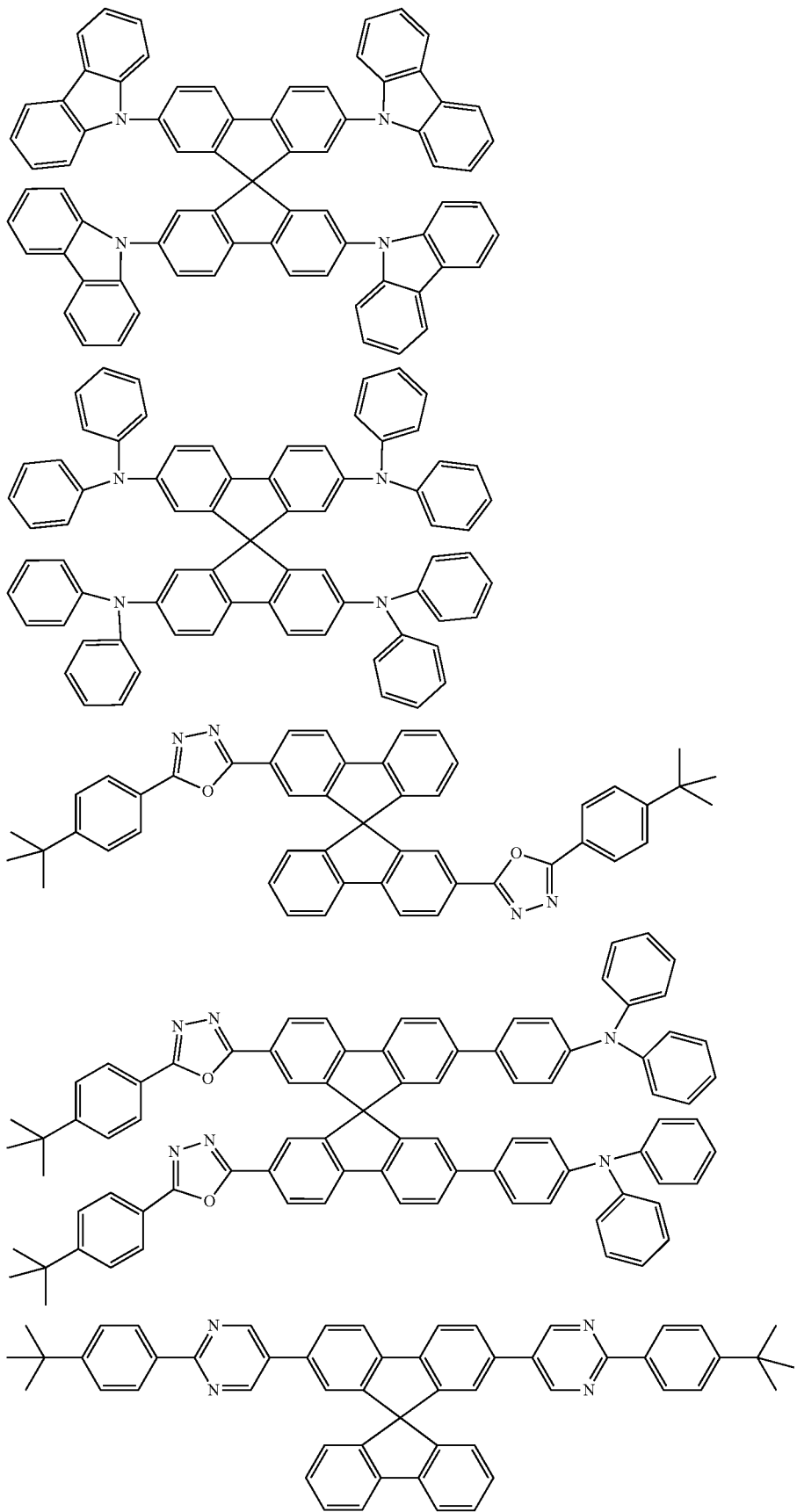

-continued
71
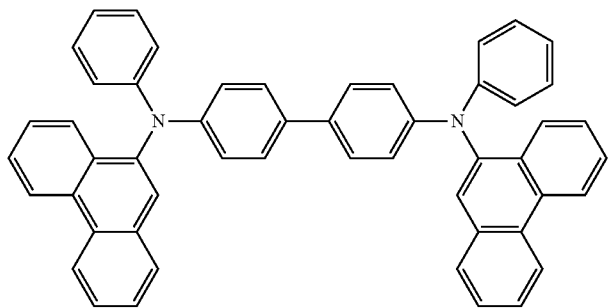
72
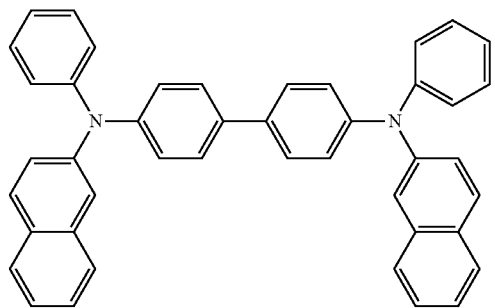
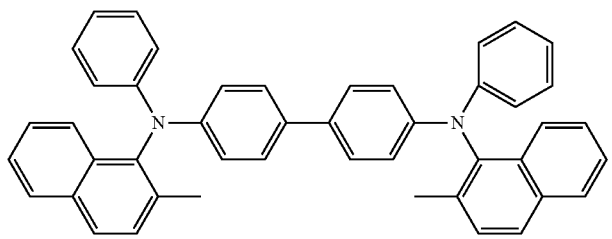
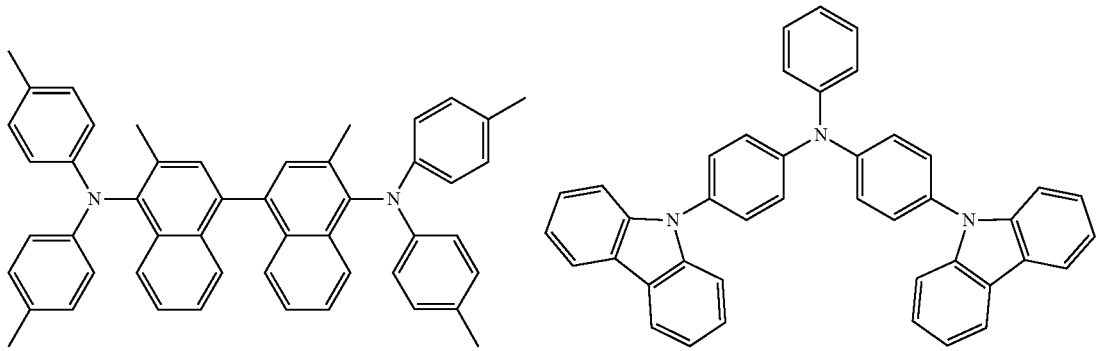
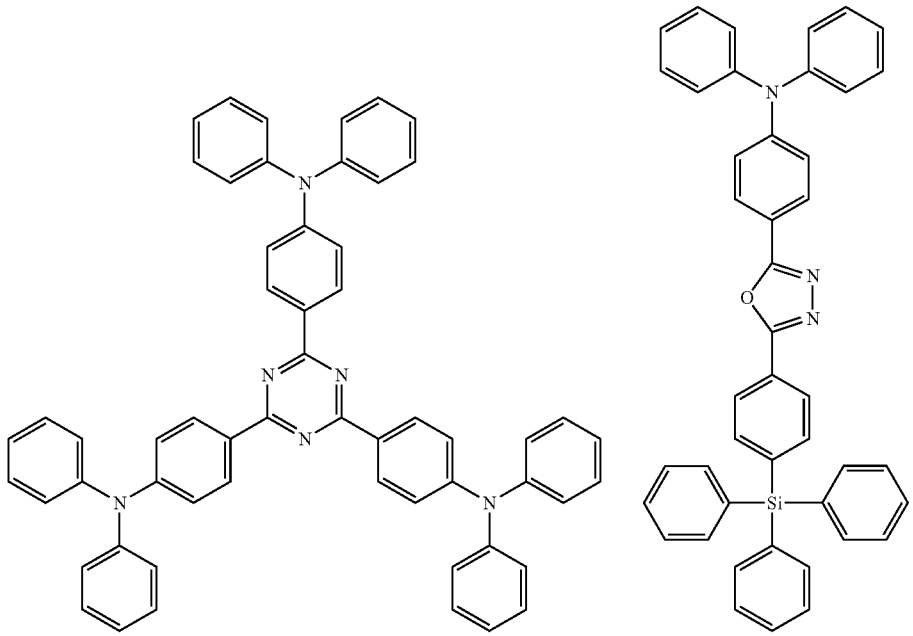

-continued
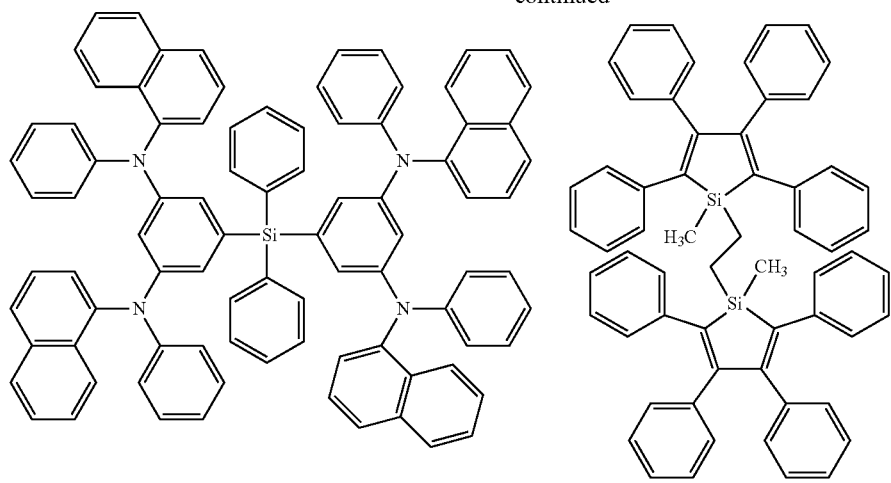
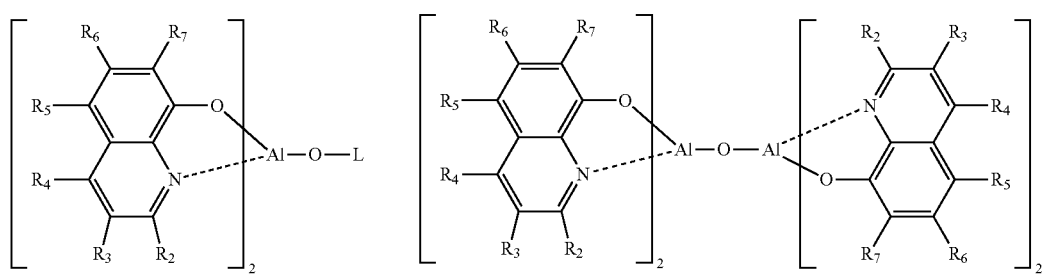
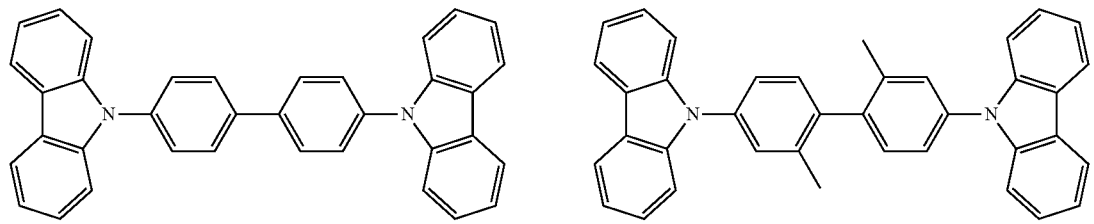
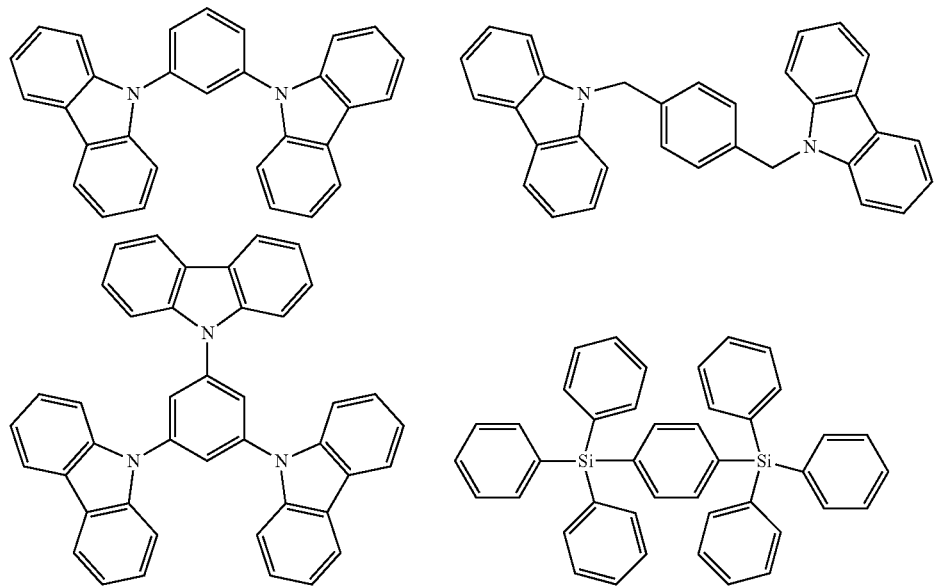

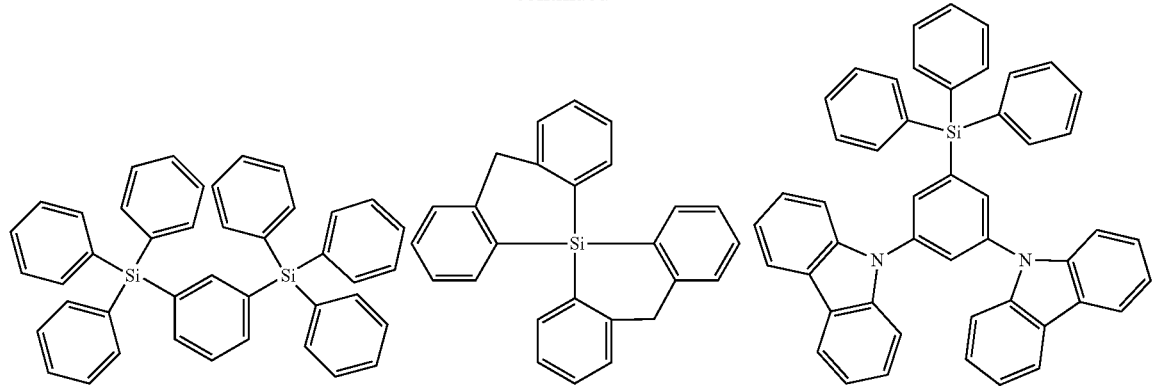
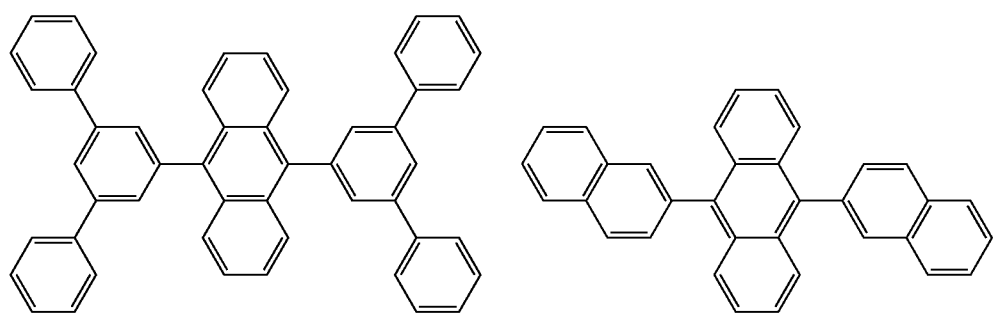
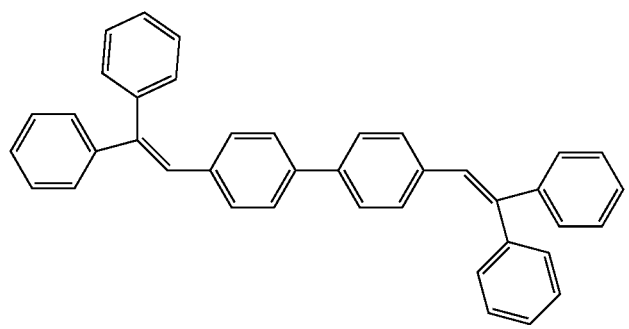
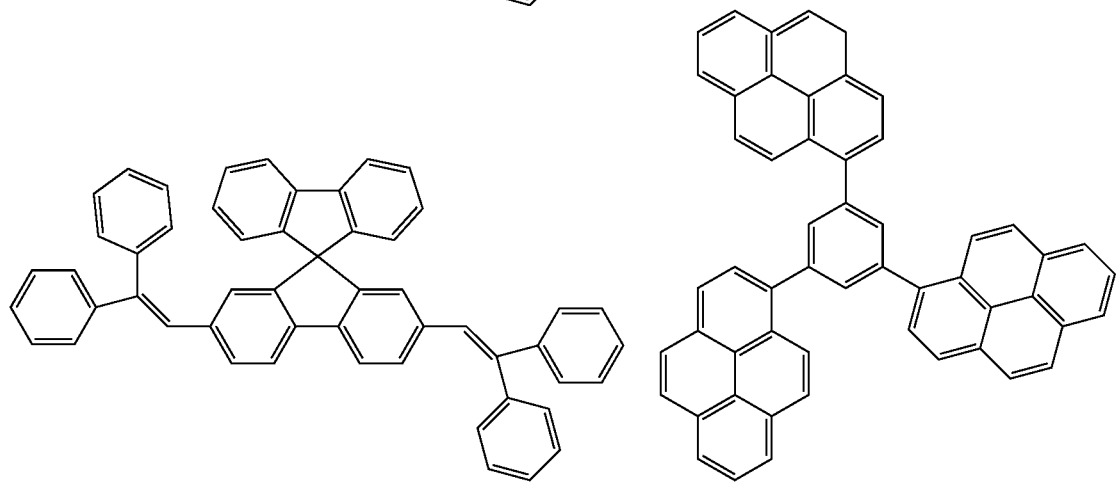

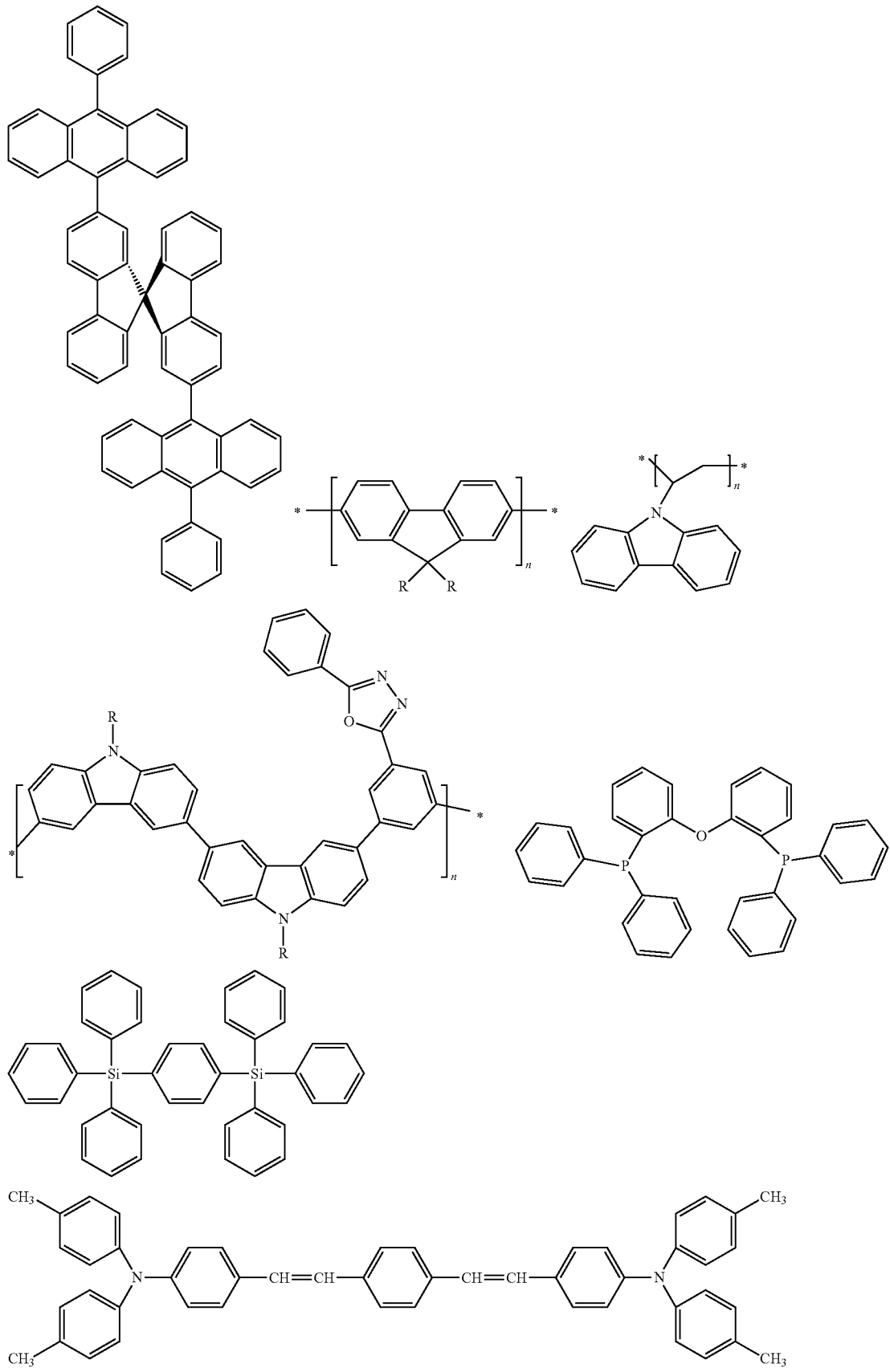

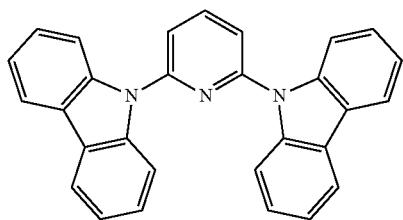
Next, preferred examples of compounds usable as a hole injection material are mentioned below.
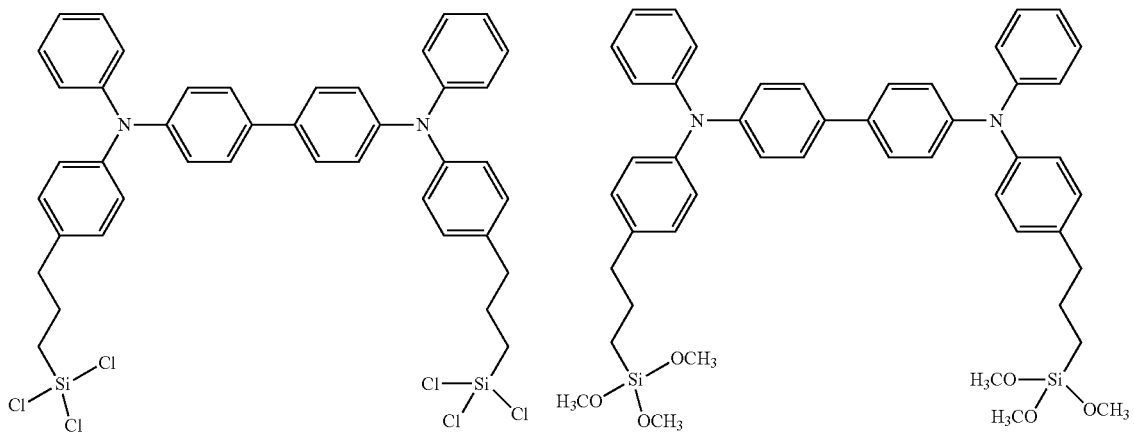
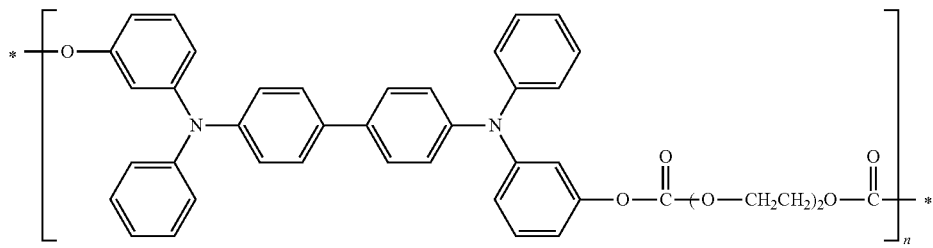
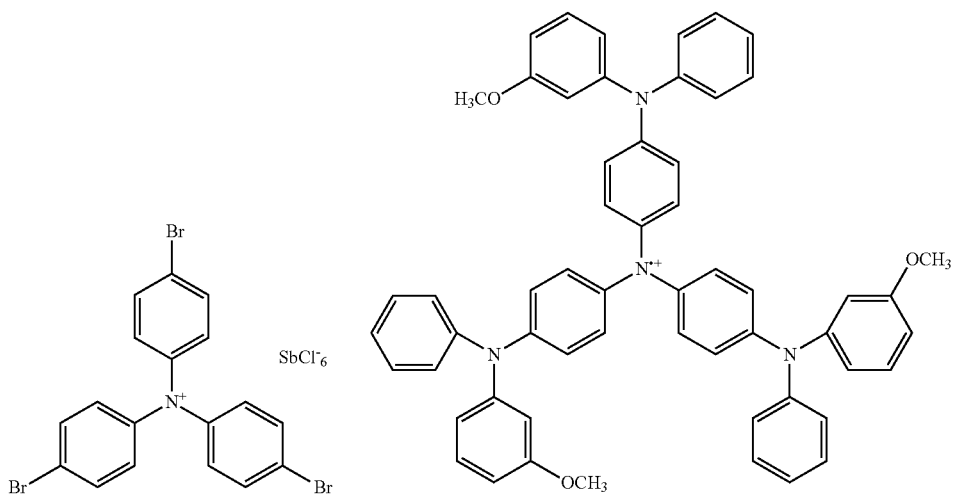

-continued
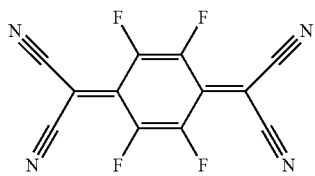
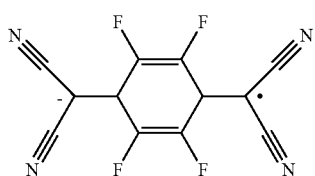
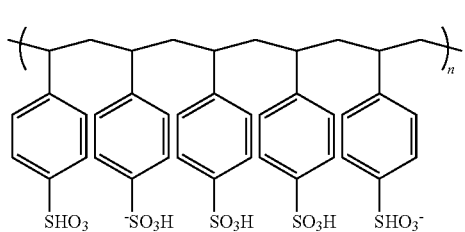
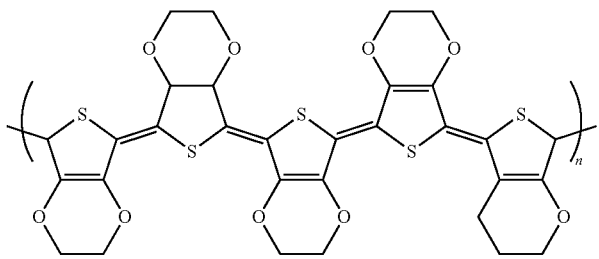
Next, preferred examples of compounds usable as a hole transport material are mentioned below.
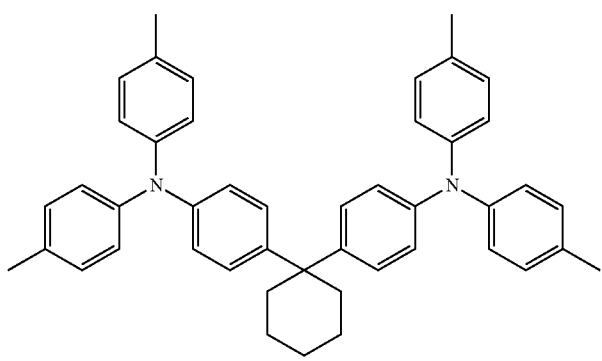
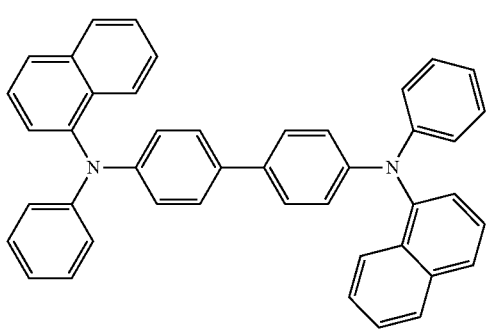

-continued
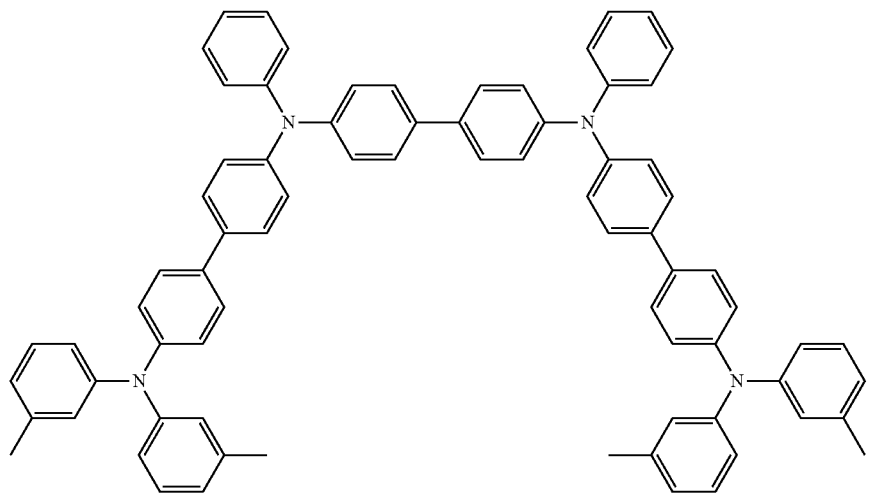
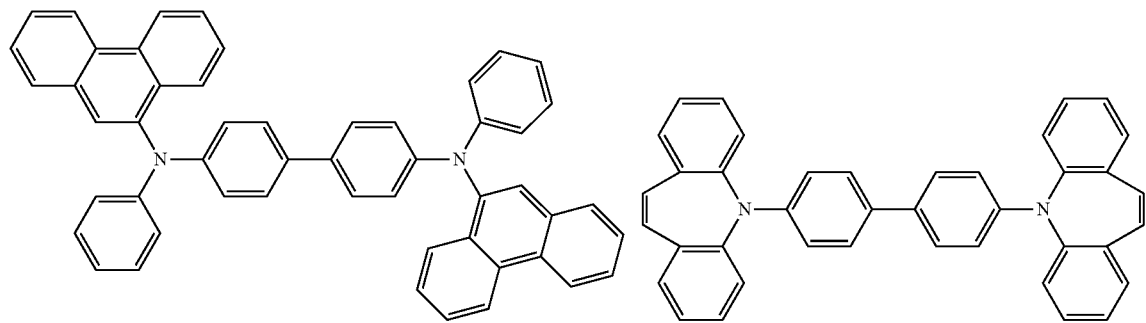
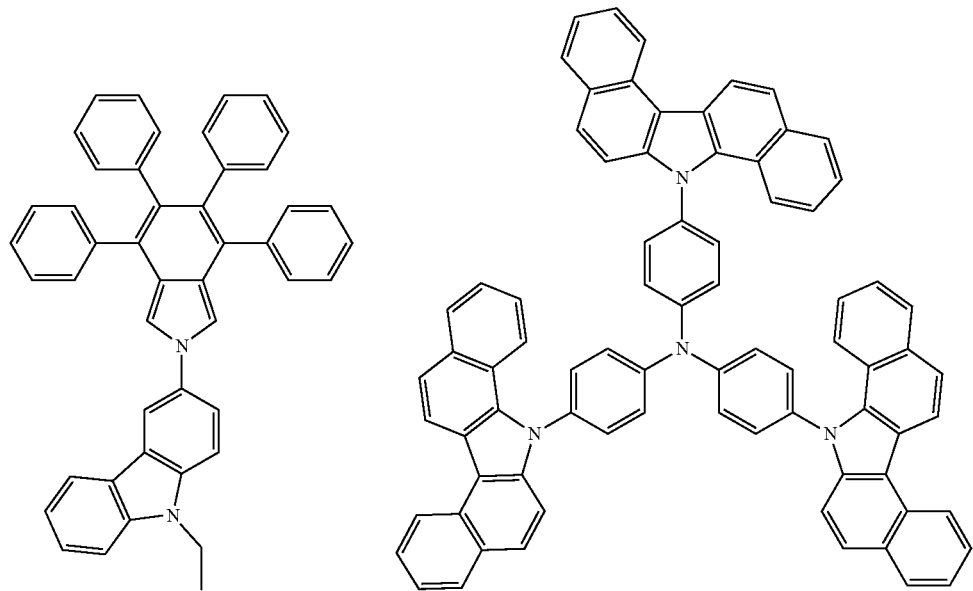

85
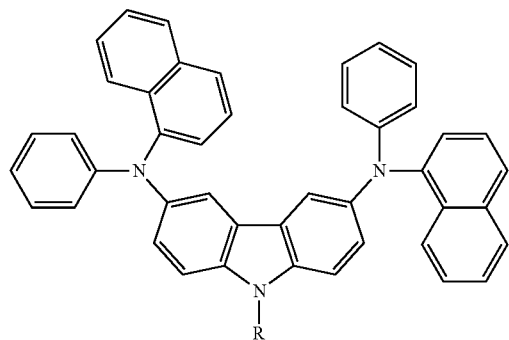
86
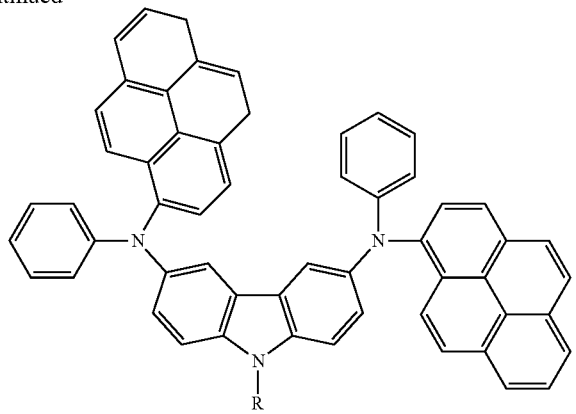
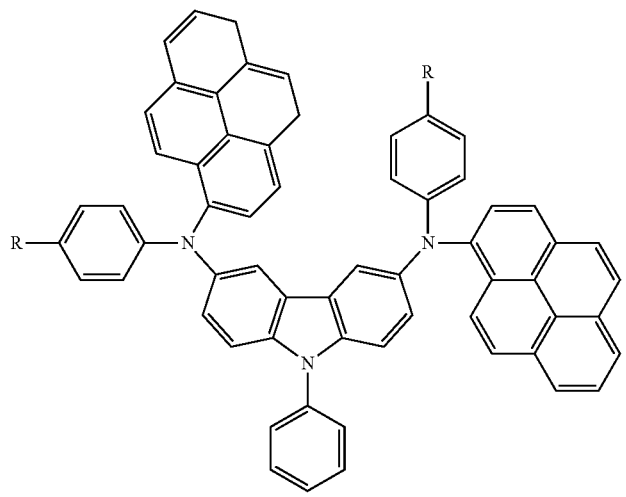
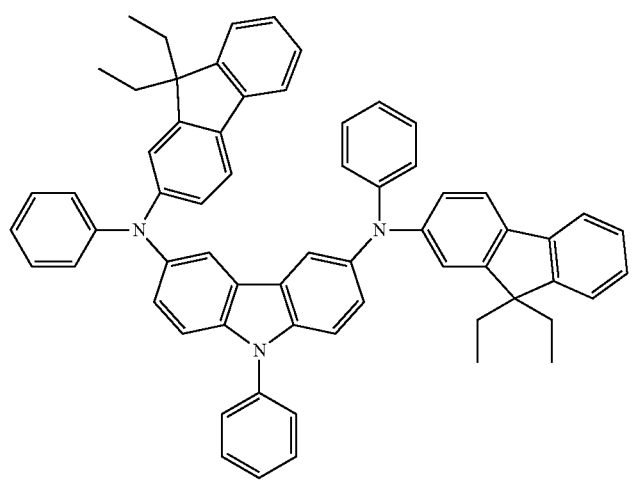

-continued
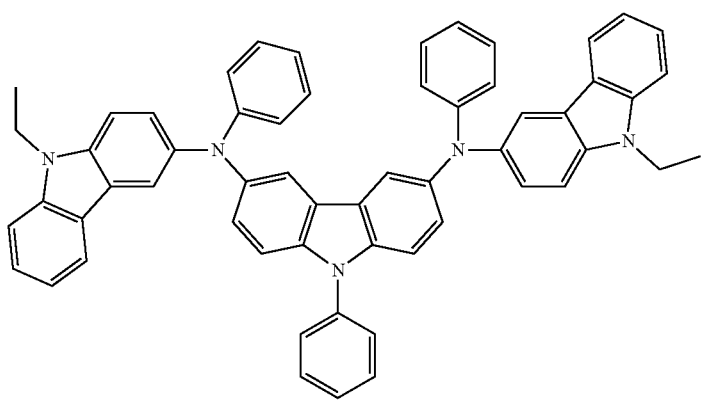
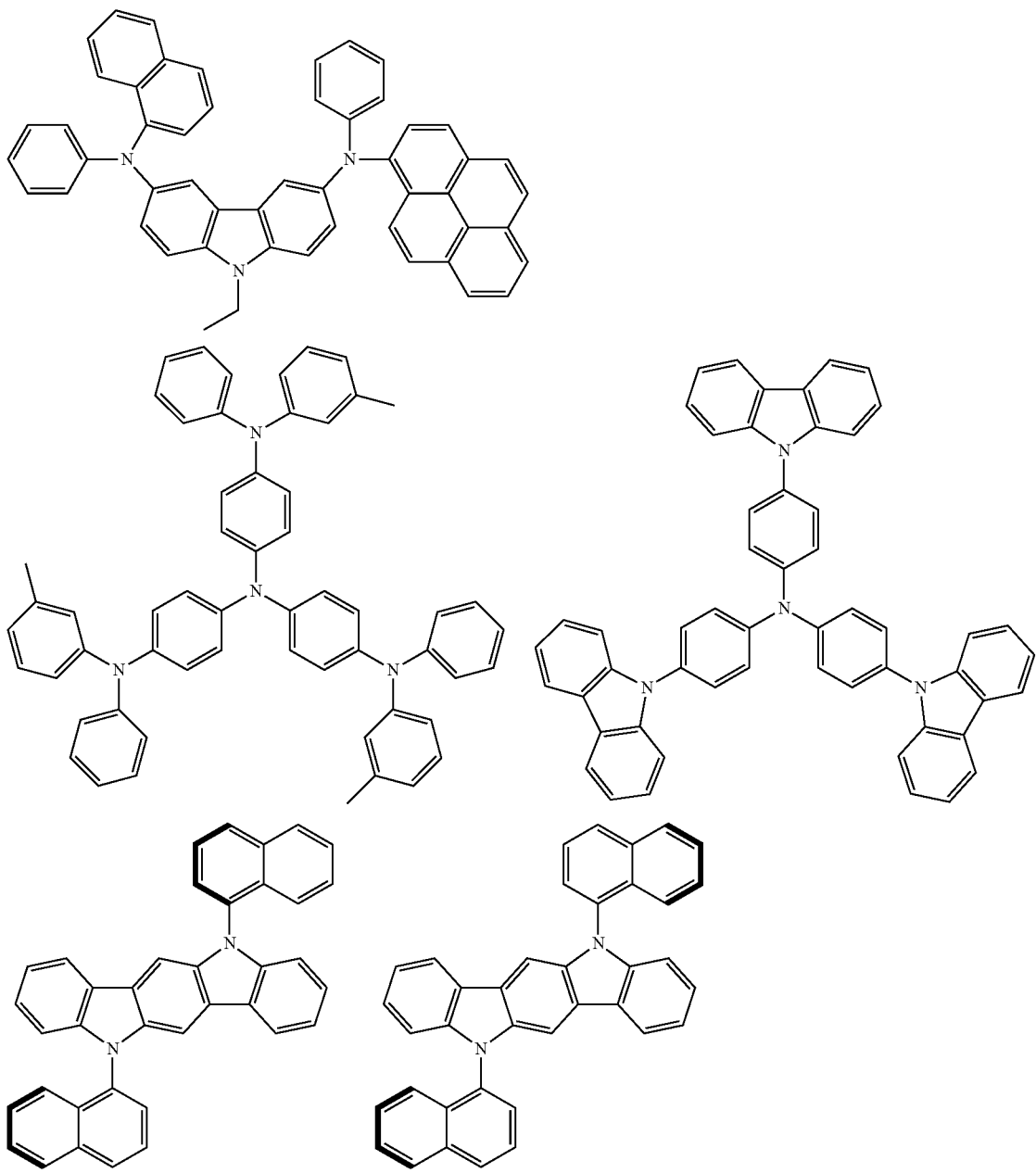

-continued
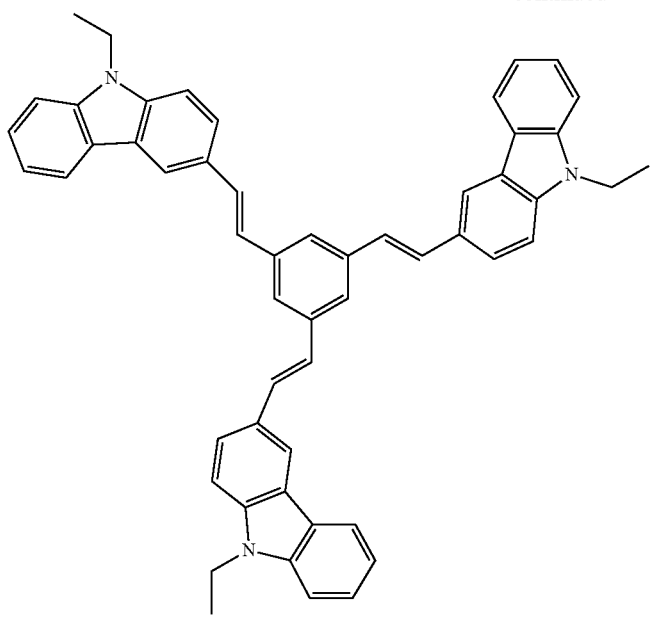
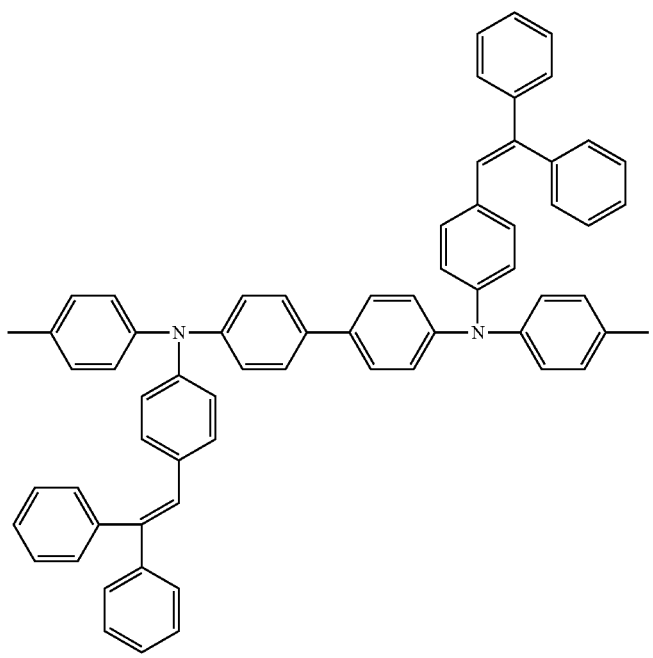
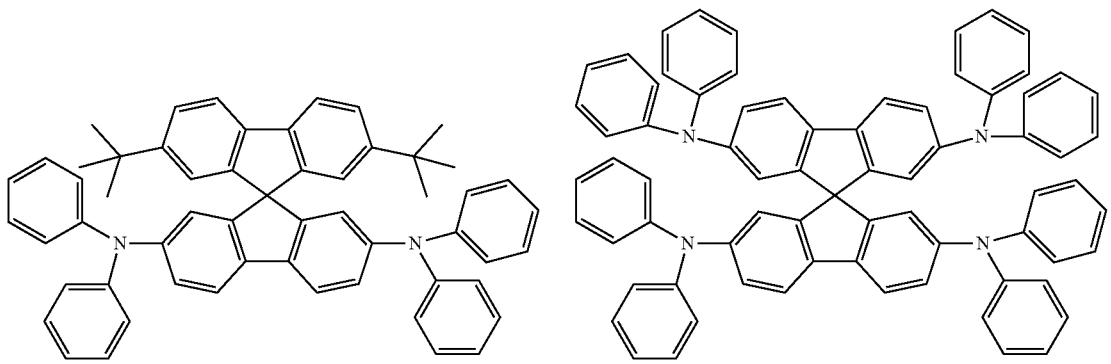

-continued
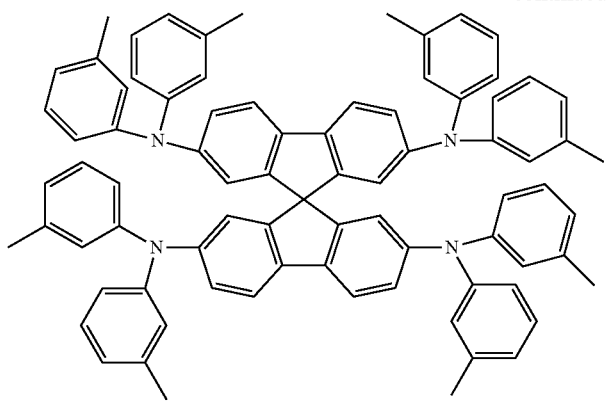
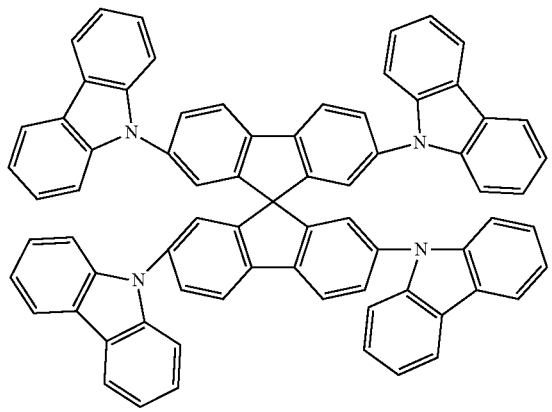
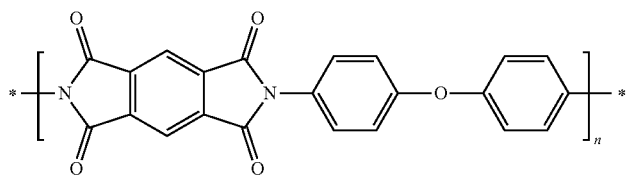
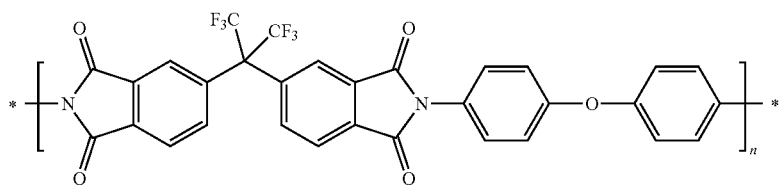
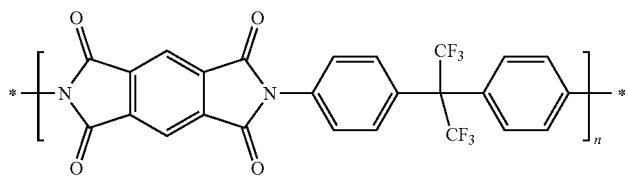
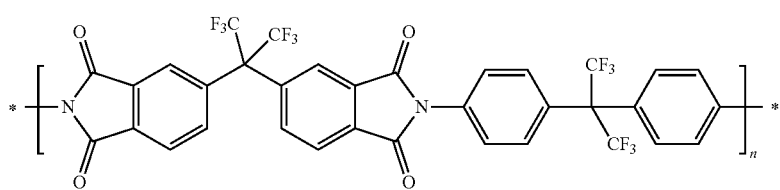

93
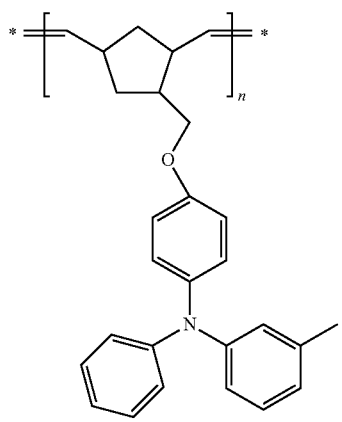
-continued
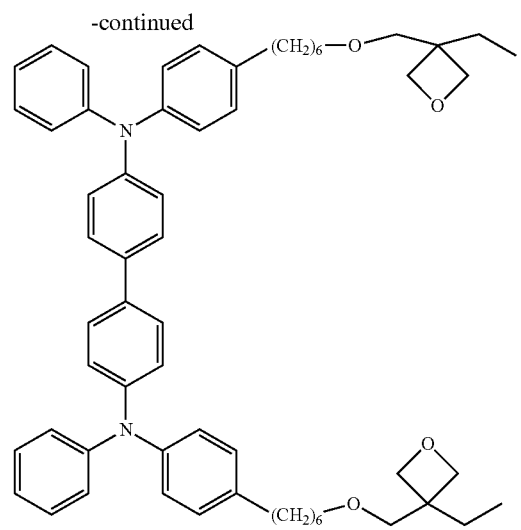
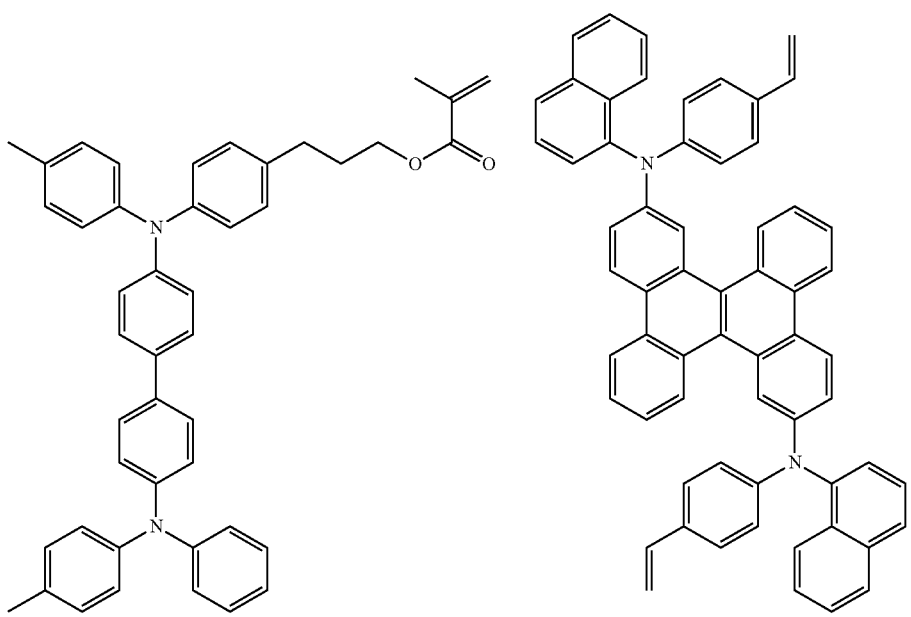
R =
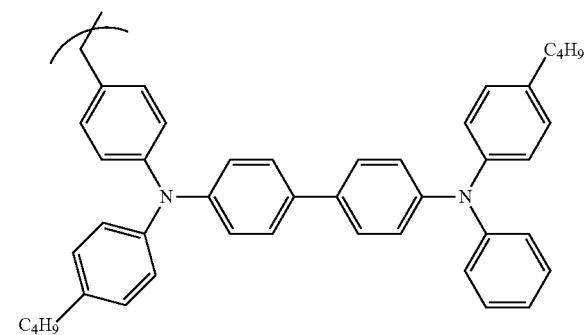

-continued
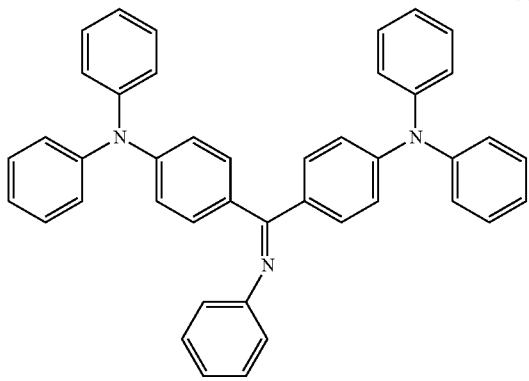
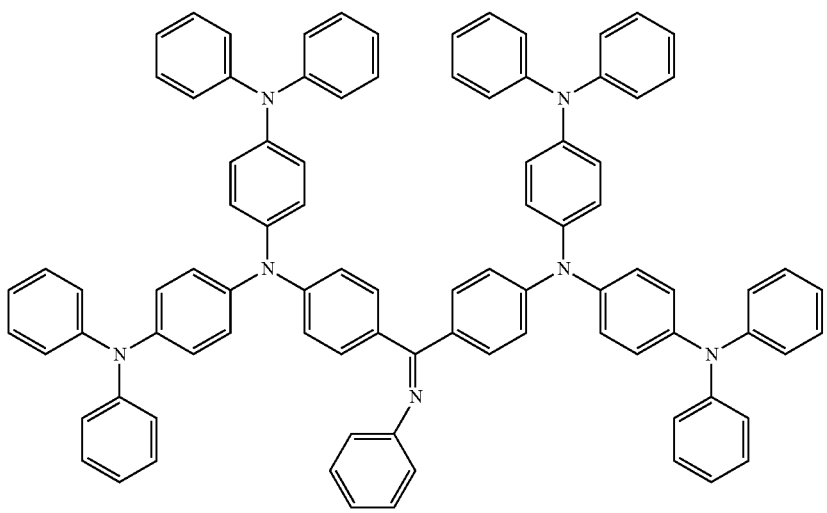
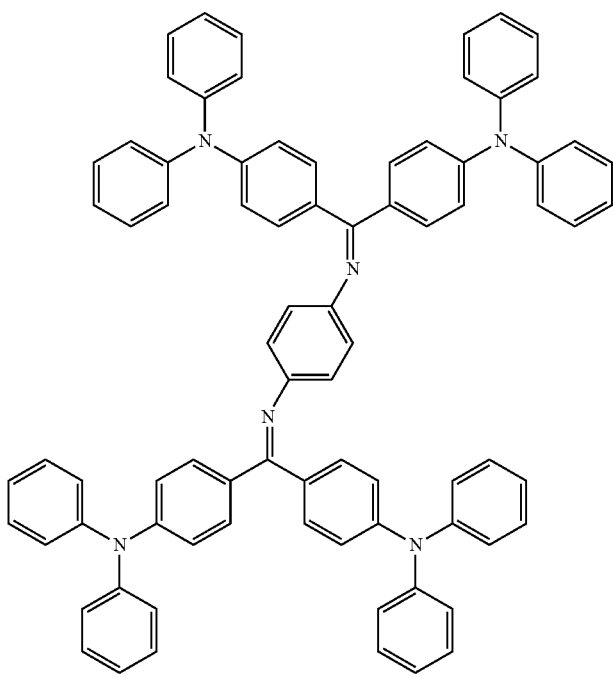

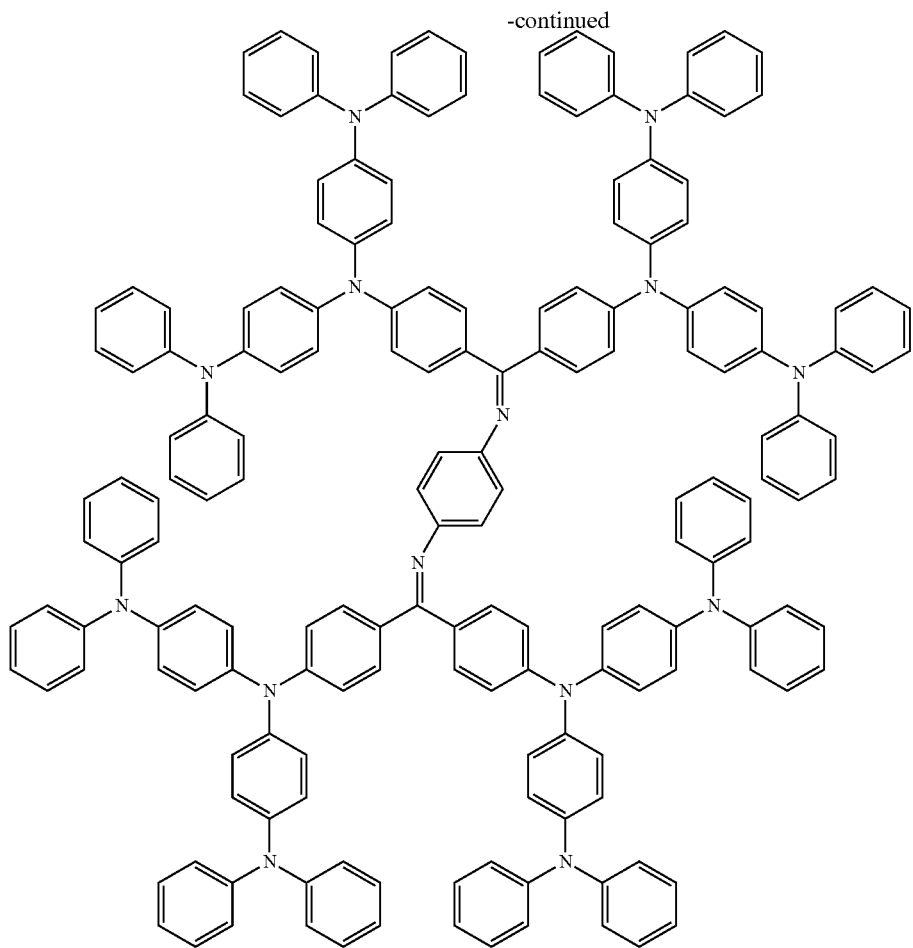
Next, preferred examples of compounds usable as an electron blocking material are mentioned below.
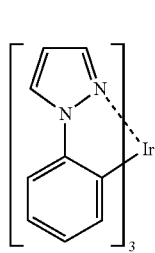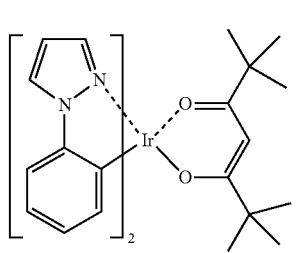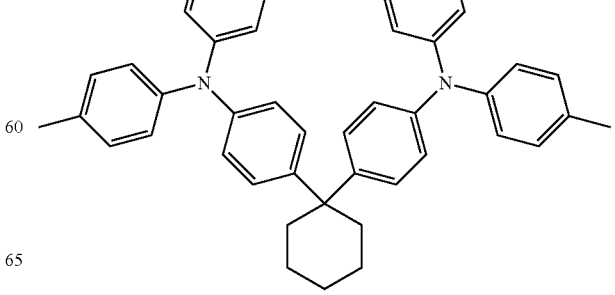

-continued
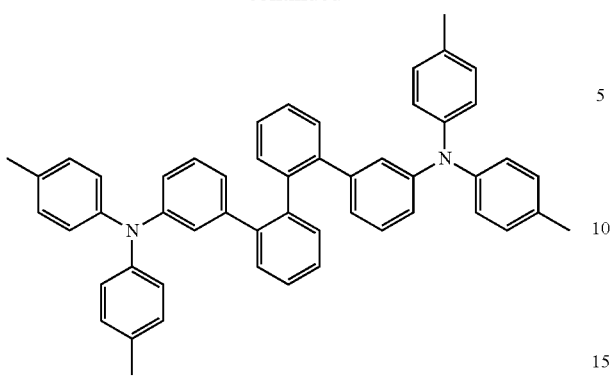
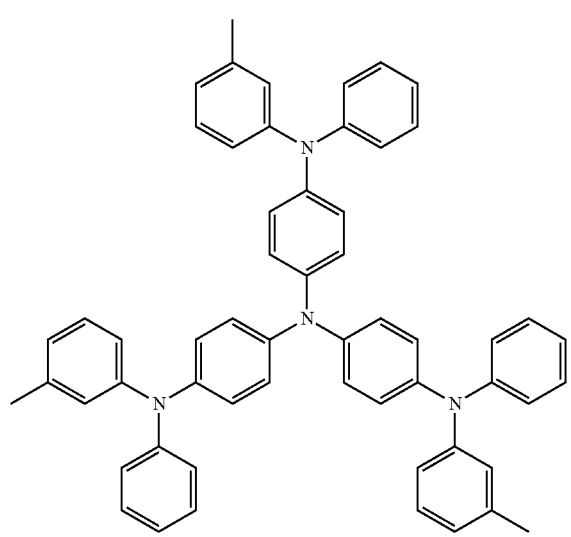
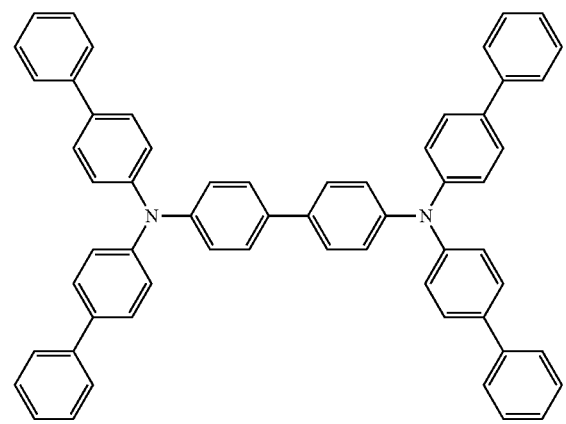 [SMILES: c1ccc(-c2ccc(N(c3ccc(-c4ccccc4)cc3)c3ccc(-c4ccc(N(c5ccc(-c6ccccc6)cc5)c5ccc(-c6ccccc6)cc5)cc4)cc3)cc2)cc1]
Next, preferred examples of compounds usable as a hole blocking material are mentioned below.
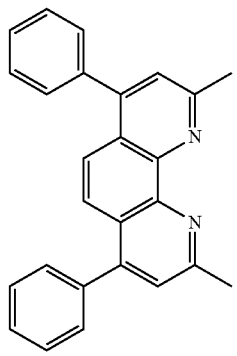
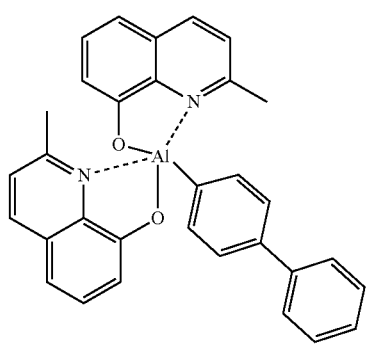
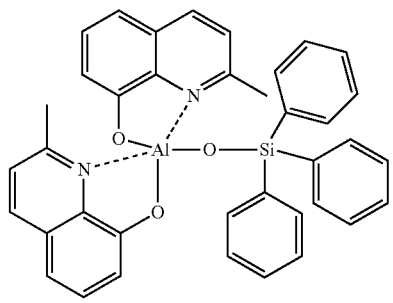
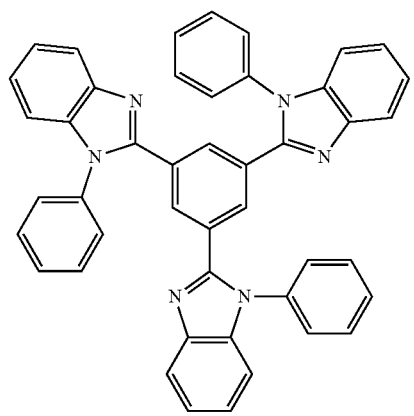

101
-continued
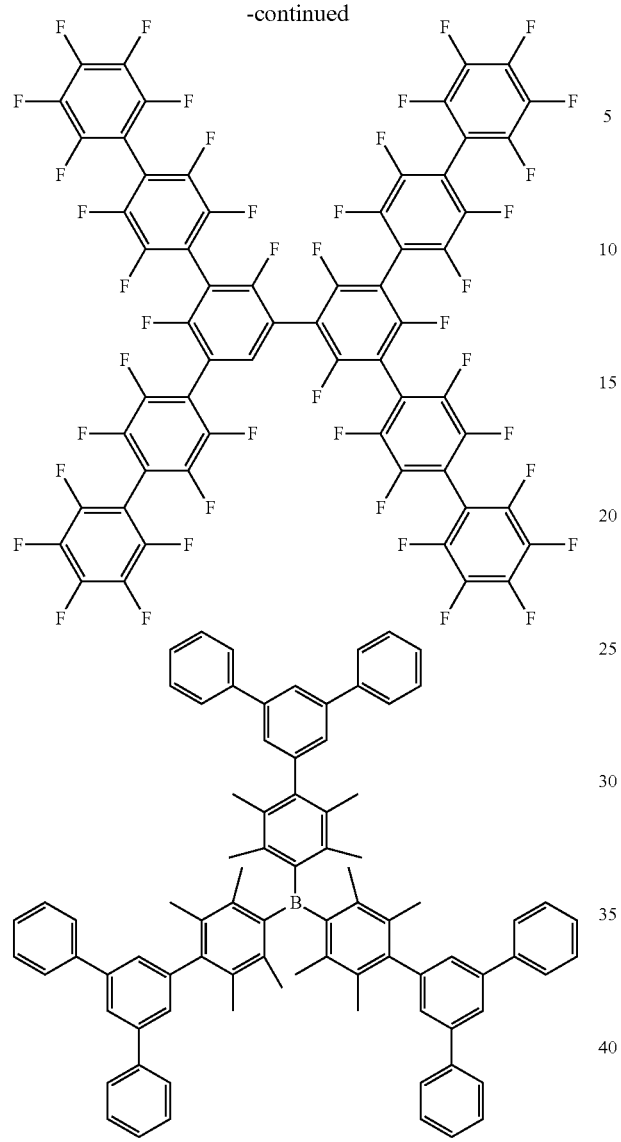
102
-continued
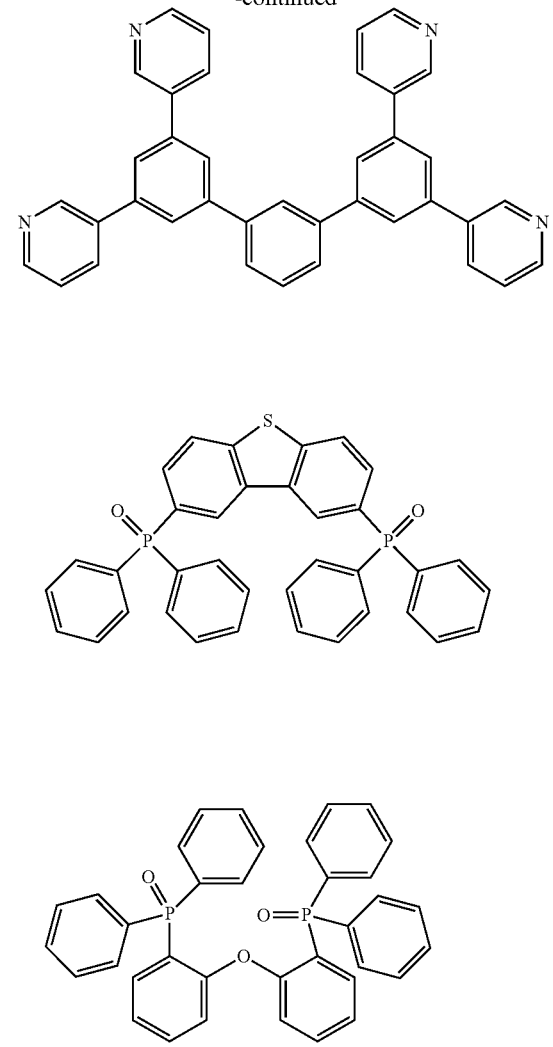
Next, preferred examples of compounds usable as an electron transport material are mentioned below.
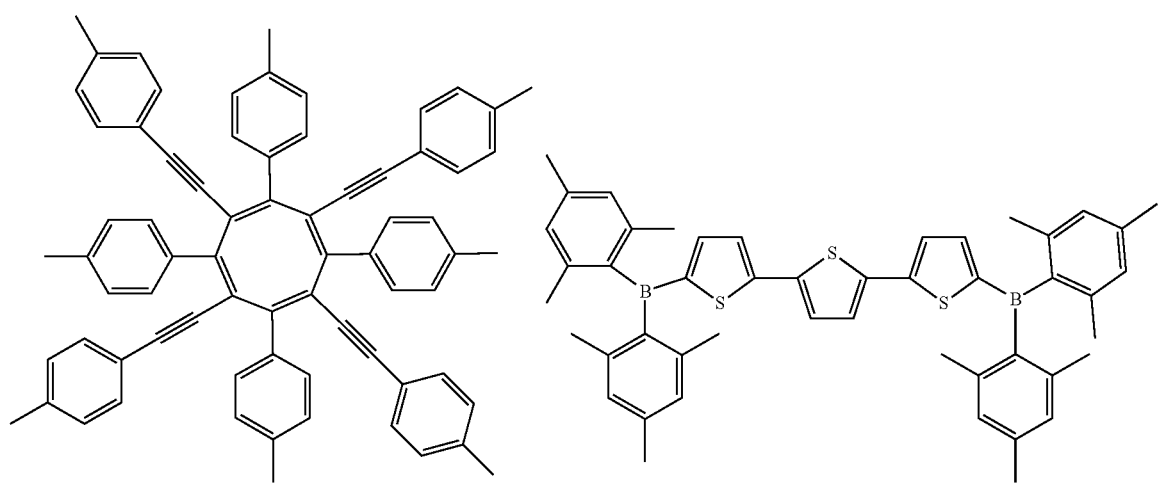

103
104
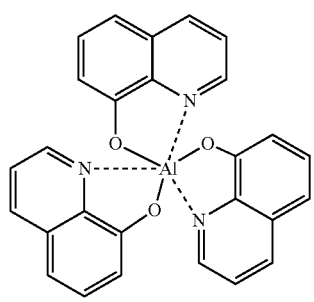
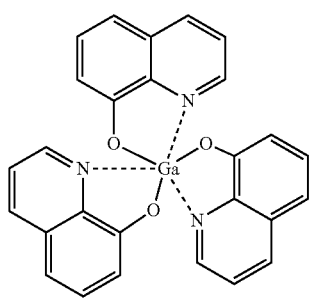
-continued
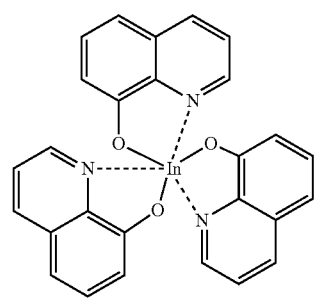
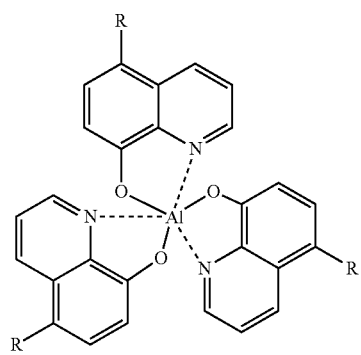
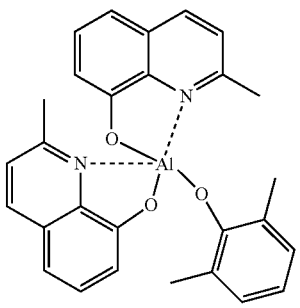
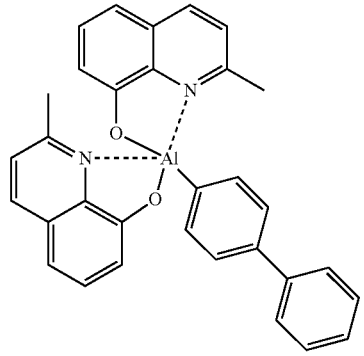
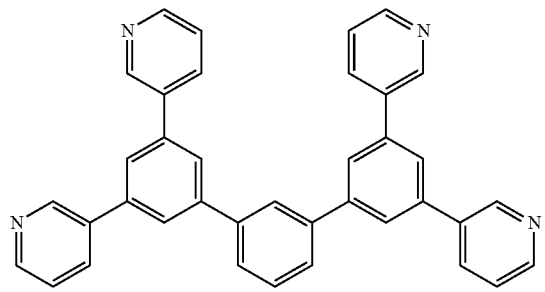
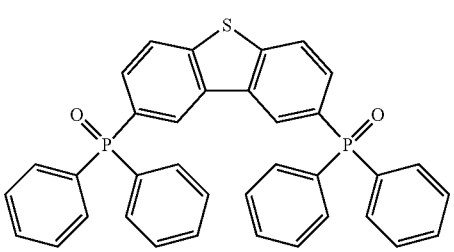
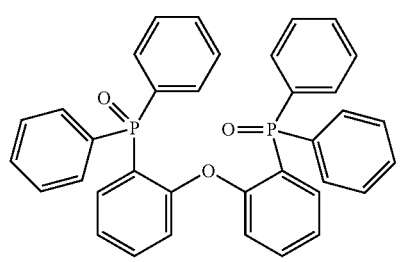
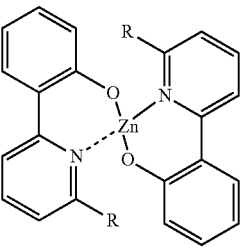
R =:
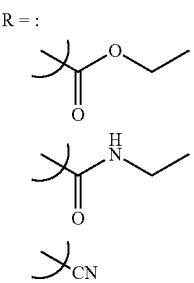
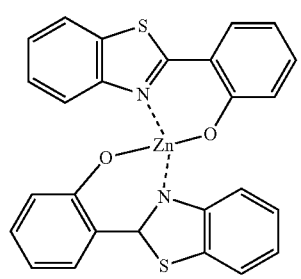
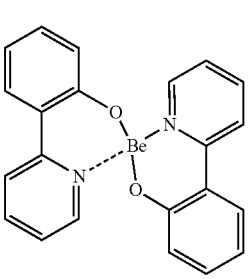
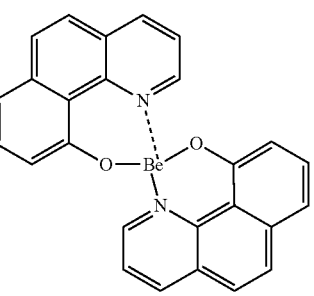

-continued
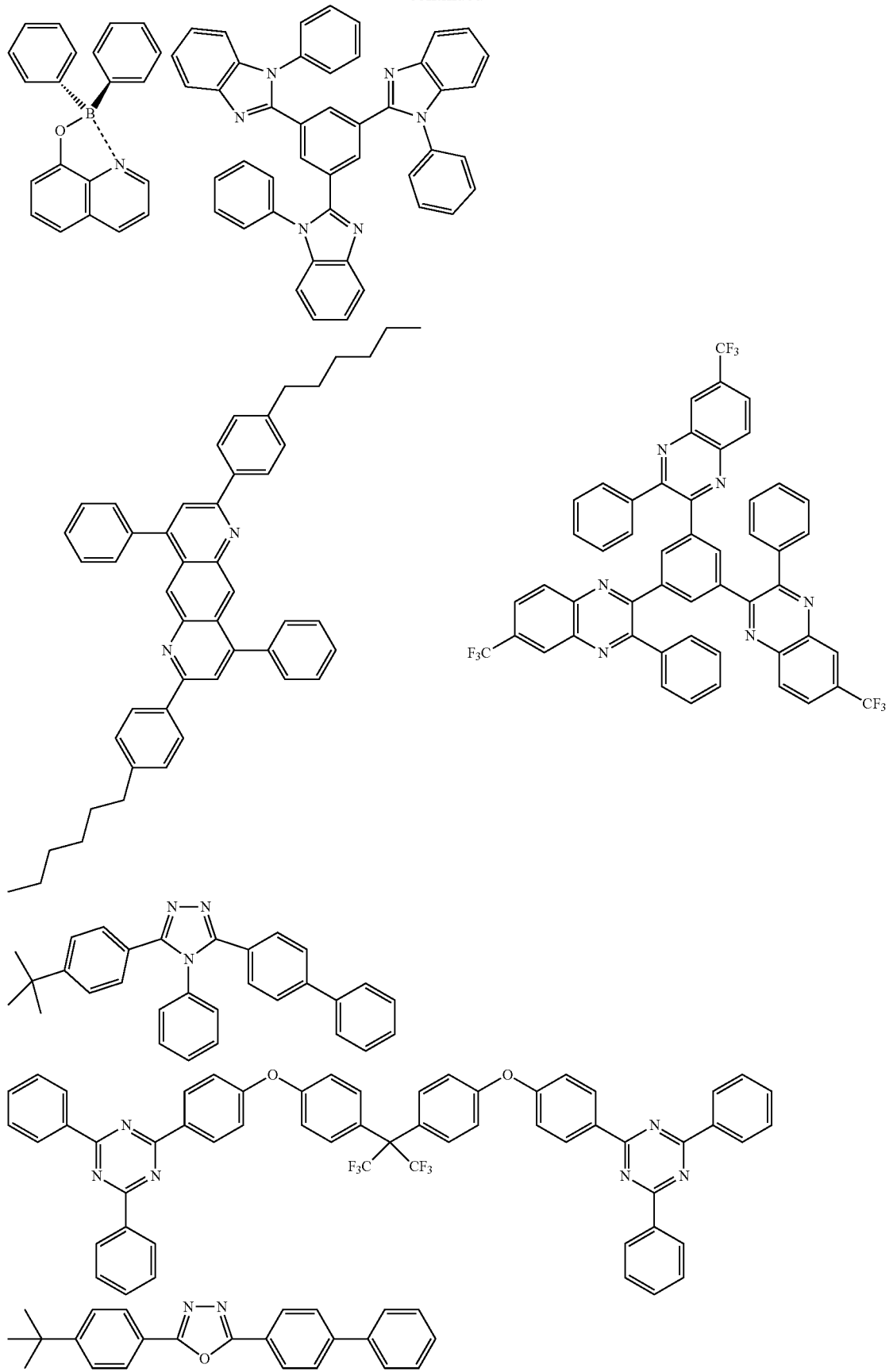

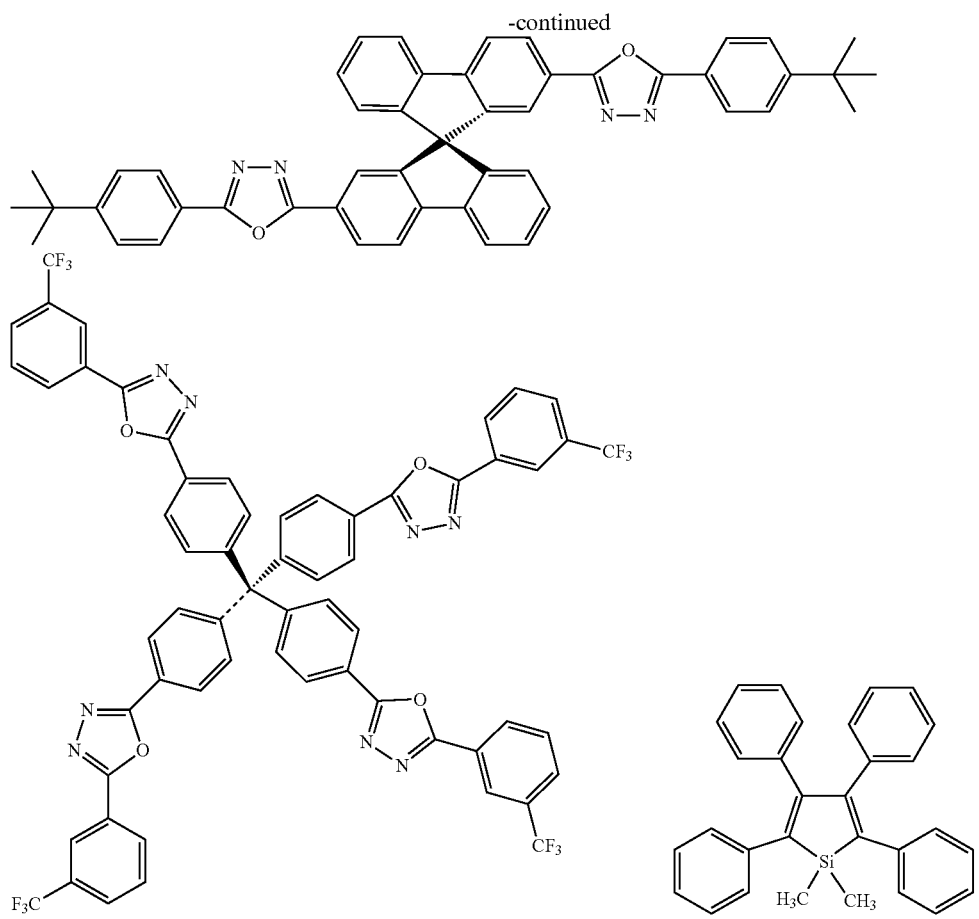
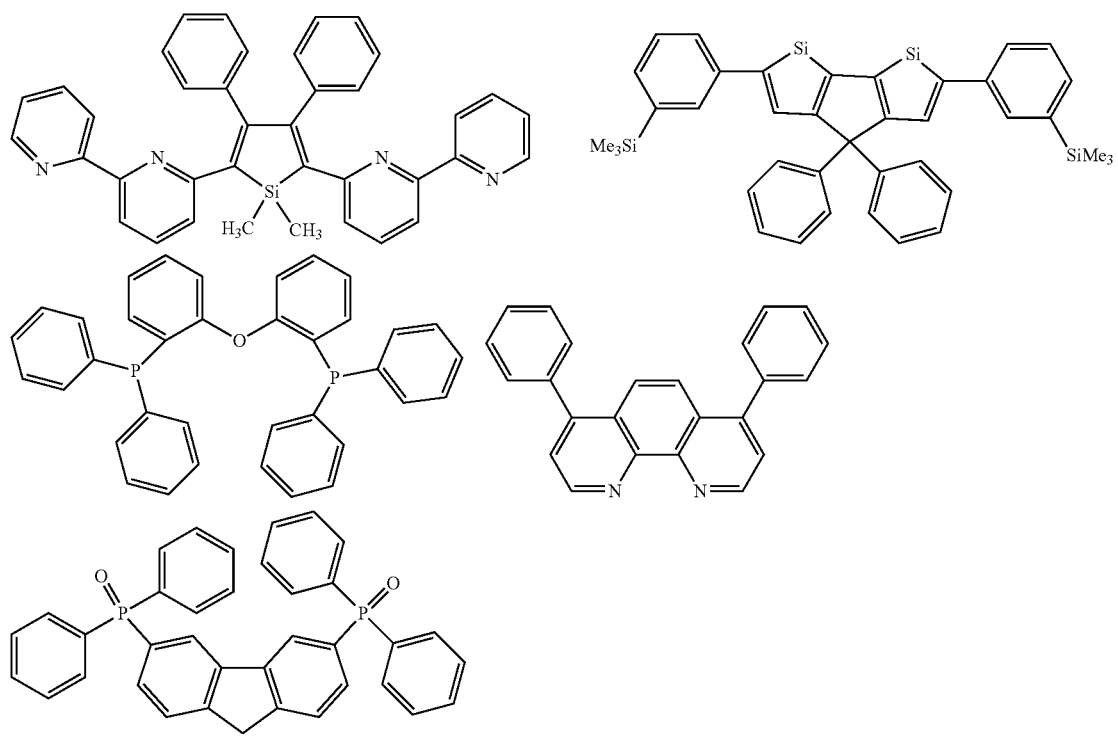

Next, preferred examples of compounds usable as an electron injection material are mentioned below.

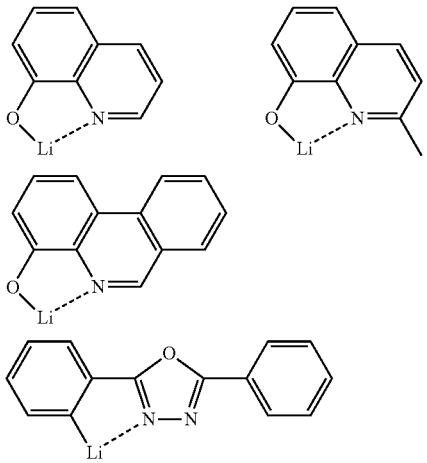

Further, examples of compounds preferred as an additive material are mentioned below. For example, the compounds may be added as a stabilizing material.

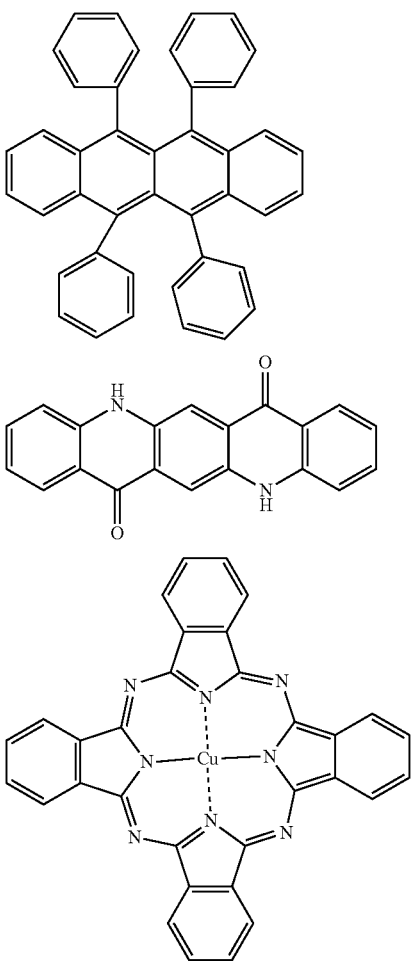

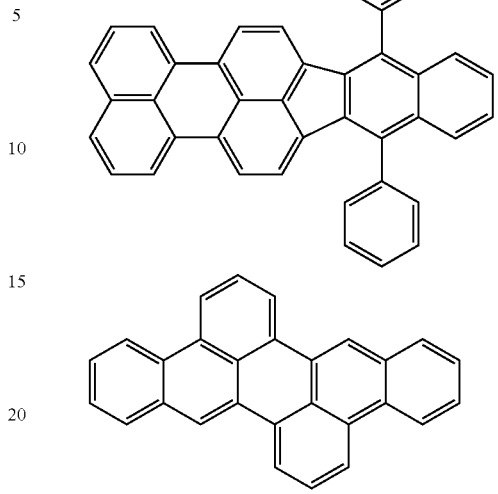

The organic electroluminescent device produced according to the above-mentioned method emits light when an electric field is applied between the anode and the cathode of the device. At this time, when the emission is by excited singlet energy, light having a wavelength depending on the energy level is confirmed as fluorescence emission and delayed fluorescence emission. On the other hand, when the emission is by excited triplet energy, light having a wavelength depending on the energy level is confirmed as phosphorescence. Ordinary fluorescence has a shorter fluorescence lifetime than delayed fluorescence emission, and the emission lifetime may be differentiated between fluorescence and delayed fluorescence.

On the other hand, regarding phosphorescence, the excited triplet energy of an ordinary organic compound such as the compound of the present invention is unstable and is converted into heat, that is, the lifetime thereof is extremely short and the compound may immediately deactivate, and consequently, the emission from the compound of the type could not almost observed at room temperature. For measuring the excited triplet energy of an ordinary organic compound, light emission from the compound under an extremely low-temperature condition may be detected and analyzed.

The organic electroluminescent device of the present invention may be applied to any of a single device, a structure with plural devices disposed in an array, and a structure having anodes and cathodes disposed in an X-Y matrix. According to the present invention, the compound of the present invention is contained in the light emitting layer to give an organic light emitting device having a greatly improved emission efficiency. The organic light emitting device such as the organic electroluminescent device of the present invention may be applied to a further wide range of purposes. For example, an organic electroluminescent display apparatus may be produced using the organic electroluminescent device of the invention, and for the details thereof, reference may be made to S. Tokito, C. Adachi and H. Murata, "Yuki EL Display" (Organic EL Display) (Ohmsha, Ltd.). In particular, the organic electroluminescent device of the invention may be applied to organic electroluminescent illuminations and backlights which are highly demanded.

EXAMPLES

The features of the present invention will be described more specifically with reference to Synthesis Examples and Examples given below. The materials, processes, procedures and the like shown below may be appropriately modified unless they deviate from the substance of the invention. Accordingly, the scope of the invention is not construed as being limited to the specific examples shown below. The HOMO level and the LUMO level were measured using an in-air photoelectron spectrometer (by Riken Keiki Co., Ltd., AC3) and a UV/Vis/NIR spectrophotometer (by PerkinElmer Corp., LAMBDA950); the time-dependent change of emission intensity was measured using a fluorescence spectrophotometer (by Horiba, Ltd., FluoroMax-4); and the emission characteristics were evaluated using an absolute external quantum efficiency measuring system (by Hamamatsu Photonics K.K., C9920-12), a spectrometer (by Hamamatsu Photonics K.K., PMA-12), a small-size fluorescent lifetime measuring device (by Hamamatsu Photonics K.K., Quantaurus-Tau C11367-21), an absolute PL quantum yield measuring device (by Hamamatsu Photonics K.K., Quantaurus-QY C11347-01), a nitrogen laser (by Lasertechnik Berlin Corp., M NL200) as an excited light source, and a streak camera (by Hamamatsu Photonics K.K., Model C4334).

In these Examples, the short lifetime ($\tau 1$) obtained by data fitting in measurement with Quantaurus-Tau was referred to as instantaneous fluorescence and the long lifetime ($\tau 2$) was as delayed fluorescence.

The difference ($\Delta E_{ST}$) between the excited singlet energy level ($E_{S1}$) and the excited triplet energy level ($E_{T1}$) was calculated as $\Delta E_{ST} = E_{S1} - E_{T1}$ in which the excited singlet energy level ($E_{S1}$) and the excited triplet energy level ($E_{T1}$) were determined according to the methods mentioned below.

(1) Excited Singlet Energy Level $E_{S1}$

A compound to be analyzed and DPEPO were co-evaporated in such a manner that the concentration of the compound to be analyzed could be 6% by weight to thereby prepare a sample having a deposited film with a thickness of 100 nm on an Si substrate. At room temperature (300 K), the fluorescent spectrum of the sample was measured. The emission immediately after excitation light incidence up to 100 nanoseconds after the light incidence was integrated to draw a fluorescent spectrum on a graph where the vertical axis indicates the emission intensity and the horizontal axis indicates the wavelength. The fluorescent spectrum indicates emission on the vertical axis and the wavelength on the horizontal axis. A tangent line was drawn to the rising of the emission spectrum on the short wavelength side, and the wavelength value λedge [nm] at the intersection between the tangent line and the horizontal axis was read. The wavelength value was converted into an energy value according to the following conversion expression to calculate $E_{S1}$.

$E_{S1}[eV]=1239.85/\lambda \text{edge}$  Conversion Expression:

For emission spectrum measurement, a nitrogen laser (MNL200, by Lasertechnik Berlin Corporation) was used as the excitation light source, and a streak camera (C4334, by Hamamatsu Photonics K.K.) was used as a detector.

(2) Excited Triplet Energy Level $E_{T1}$

The same sample as that for measurement of the excited singlet energy level $E_{S1}$ was cooled to 5 [K], and the sample for phosphorescence measurement was irradiated with excitation light (337 nm), and using a streak camera, the phosphorescence intensity thereof was measured. The emission in 1 millisecond after excitation light incidence up to 10 milliseconds after the light incidence was integrated to draw a phosphorescent spectrum on a graph where the vertical axis indicates the emission intensity and the horizontal axis indicates the wavelength. A tangent line was drawn to the rising of the phosphorescent spectrum on the short wavelength side, and the wavelength value λedge [nm] at the intersection between the tangent line and the horizontal axis was read. The wavelength value was converted into an energy value according to the following conversion expression to calculate $E_{T1}$.

$E_{T1}[eV]=1239.85/\lambda \text{edge}$  Conversion Expression:

The tangent line to the rising of the phosphorescent spectrum on the short wavelength side was drawn as follows. While moving on the spectral curve from the short wavelength side of the phosphorescent spectrum toward the maximum value on the shortest wavelength side among the maximum values of the spectrum, a tangent line at each point on the curve toward the long wavelength side was taken into consideration. With rising thereof (that is, with increase in the vertical axis), the inclination of the tangent line increases. The tangent line drawn at the point at which the inclination value has a maximum value was referred to as the tangent line to the rising on the short wavelength side of the phosphorescent spectrum.

The maximum point having a peak intensity of 10% or less of the maximum peak intensity of the spectrum was not included in the maximum value on the above-mentioned shortest wavelength side, and the tangent line drawn at the point which is closest to the maximum value on the shortest wavelength side and at which the inclination value has a maximum value was referred to as the tangent lint to the rising on the short wavelength side of the phosphorescent spectrum.

Synthesis Example 1

Sodium hydride (60 wt %, 288 mg) was put into a 200-mL eggplant flask, and washed with hexane. Tetrahydrofuran (60 mL) and 2,7-ditrifluoromethylcarbazole (1.82 g) were added thereto and stirred at room temperature for 1 hour, and then tetrafluoroisophthalonitrile (240 mg) was added and further stirred at room temperature for 22 hours. Water (50 mL) was added and the precipitate was taken out through filtration. The resultant precipitate was purified through silica gel column chromatography to give a compound 1 (1.5 g, yield 94%).

A $^1$H NMR spectrum of a DMSO-d6 solution of the compound 1 is shown in FIG. 2.

Synthesis Example 2

Sodium hydride (60 wt %, 288 mg) was put into a 200-mL eggplant flask, and washed with hexane. Tetrahydrofuran (60 mL) and 2,7-ditrifluoromethylcarbazole (1.82 g) were added thereto and stirred at room temperature for 1 hour, and then tetrafluoroterephthalonitrile (240 mg) was added and further stirred at room temperature for 22 hours. Water (50 mL) was added and the precipitate was taken out through filtration. The resultant precipitate was purified through silica gel column chromatography to give a compound 2 (1.45 g, yield 91%).

A $^1$H NMR spectrum of a DMSO-d6 solution of the compound 1 is shown in FIG. 3.

Synthesis Example 3

Cesium carbonate (2.45 g), 2,7-ditrifluoromethylcarbazole (1.52 g), and perfluoroparaxylene (286 mg) were put into a 200-mL eggplant flask, and dimethyl sulfoxide (40 mL) was added thereto and stirred at room temperature for 12 hours. Water (20 mL) was added and the precipitate was taken out through filtration. The resultant precipitate was purified through silica gel column chromatography to give a compound 3 (1.2 g, yield 84%).

The compound 3 was insoluble in an ordinary heavy solvent, and was identified through high-resolution mass spectrometry and elementary analysis.

Synthesis Example 4

Sodium hydride (60 wt %, 240 mg) was put into a 200-mL eggplant flask, and washed with hexane. N-methyl-2-pyrrolidone (60 mL) and 2,7-ditrifluoromethylcarbazole (1.52 g) were added thereto and stirred at room temperature for 1 hour, and then 2,4-diphenyl-6-(3,4,5-trifluorophenyl)-1,3,5-triazine (510 mg) was added and stirred at 100° C. for 16 hours. Water (50 mL) was added and the precipitate was taken out through filtration. The resultant precipitate was purified through silica gel column chromatography to give a compound 4 (1.12 g, yield 69%).

A $^1$H NMR spectrum of a DMSO-d6 solution of the compound 4 is shown in FIG. 4.

2,4-Diphenyl-6-(3,4,5-trifluorophenyl)-1,3,5-triazine was synthesized with reference to Adv. Mater. 2015, 27, 5861-5867.

The HOMO level and the LUMO level, and the lowest excited triplet energy level $E_{T1}$, and $\Delta E_{ST}$ of the compound 1 and the compound 2 synthesized in Synthesis Examples are shown in Table 1. Compounds (comparative compounds 1 to 6) used for comparison in these Examples are shown below, and the HOMO level and the LUMO level, and the lowest excited triplet energy level $E_{T1}$, and $\Delta E_{ST}$ of the comparative compounds 1, 2 and 4 are shown in Table 1.

Compound 1

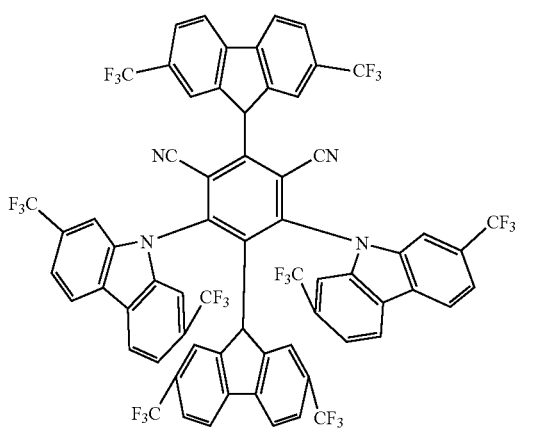

Compound 2

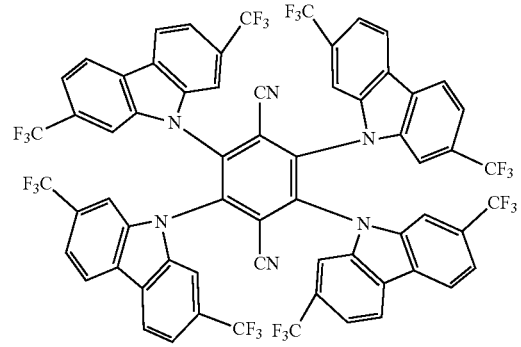

Compound 3

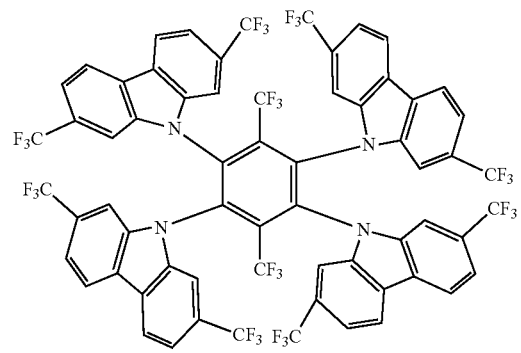

Compound 4

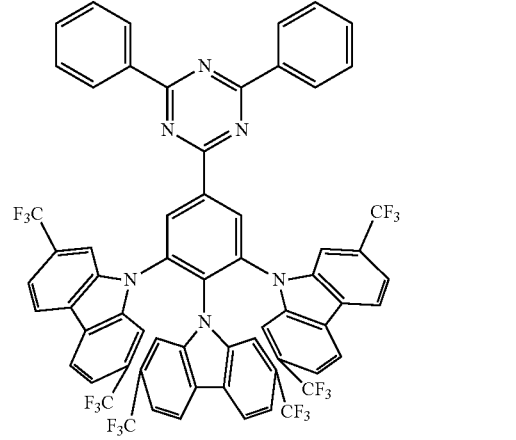

Comparative Compound 1

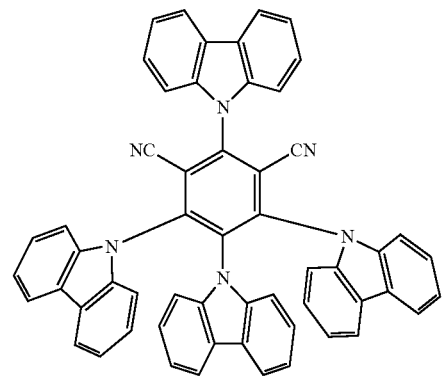

Comparative Compound 2
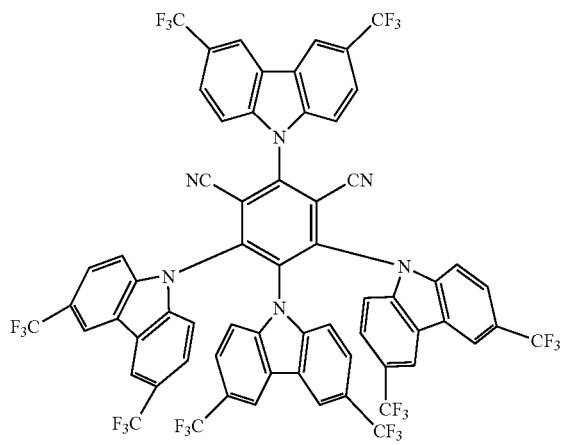
Comparative Compound 3
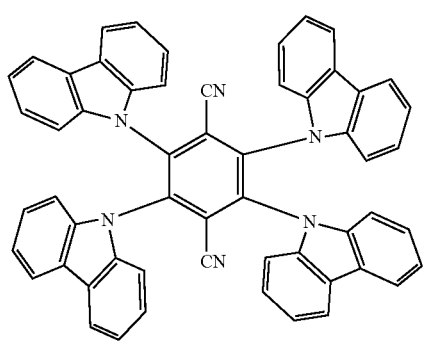
Comparative Compound 4
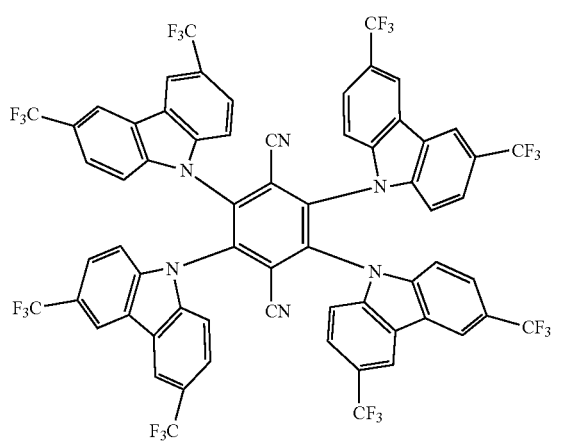
Comparative Compound 5
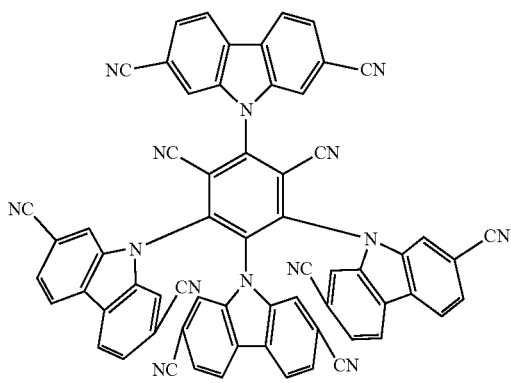
Comparative Compound 6
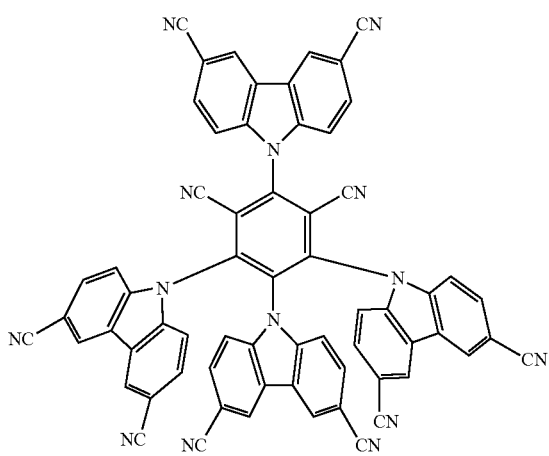
Comparative Compound 7
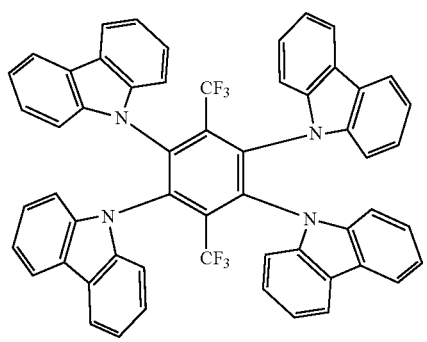

-continued

Comparative Compound 8

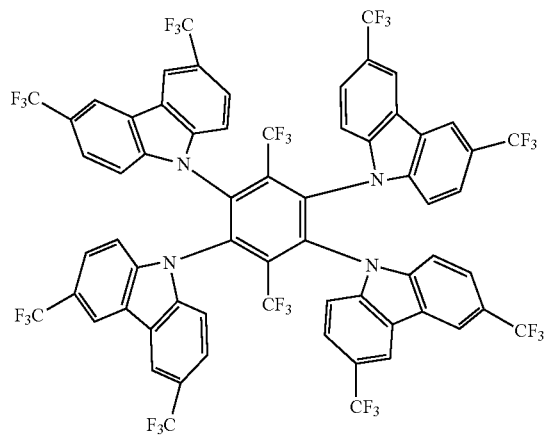

Comparative Compound 9

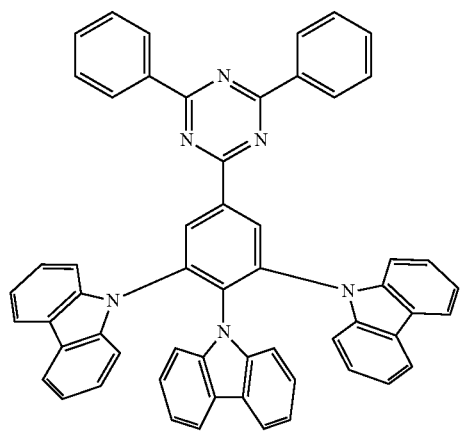

Comparative Compound 10

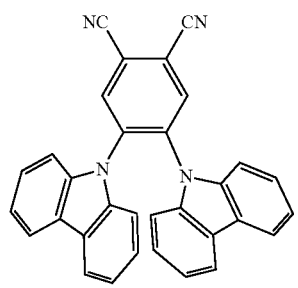

-continued

Comparative Compound 11

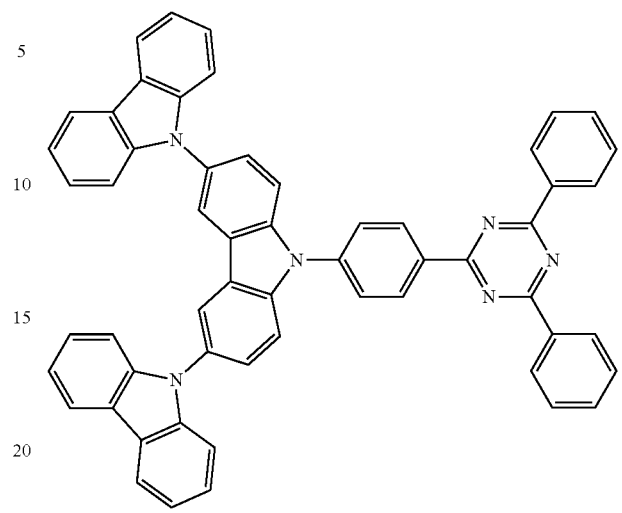

TABLE 1

| | HOMO Level | LUMO Level | $E_{T1}$ | $\Delta E_{ST}$ |
|---|---|---|---|---|
| Compound 1 | −6.6 eV | −3.7 eV | 2.88 eV | 33 meV |
| Comparative Compound 1 | −5.8 eV | −3.4 eV | 2.72 eV | — |
| Comparative Compound 2 | −6.6 eV | −3.7 eV | 2.90 eV | 41 meV |
| Compound 2 | −6.6 eV | −3.95 eV | 2.64 eV | — |
| Comparative Compound 4 | −6.6 eV | −3.95 eV | 2.70 eV | — |

As shown in Table 1, the compounds 1 and 2 and the comparative compounds 2 and 4 in which the carbazol-9-yl group is substituted with a perfluoroalkyl group have both a low HOMO level and a low LUMO level as compared with the comparative compound 1 in which the carbazol-9-yl group is not substituted with a perfluoroalkyl group. From this, it is known that when a perfluoroalkyl group is introduced into the carbazol-9-yl group of an aromatic ring substituted with a carbazol-9-yl group and an acceptor group, both the HOMO level and the LUMO level of the compound lower. However, $\Delta E_{ST}$ of the comparative compound 2 in which a perfluoroalkyl group is introduced into the carbazol-9-yl group but the substituting positions thereof are 3-position and 6-position is larger than that of the compound 1 in which the substituting positions are 2-position and 7-position. This suggests that the compound in which a perfluoroalkyl group has been introduced into the 3-position and the 6-position of the carbazol-9-yl group therein could hardly undergo reverse intersystem crossing from the excited triplet state to the excited singlet state as compared with the compound 1 in which a perfluoroalkyl group has been introduced into the 2-position and the 7-position of the carbazol-9-yl group.

[Production of Organic Photoluminescent Device and Evaluation of Emission Characteristics Thereof]

Example 1

A toluene solution of the compound 1 (concentration $10^{-5}$ mol/L) was prepared.

A thin film (single film) of the compound 1 was formed in a thickness of 100 nm on a quartz substrate, through vapor deposition in a vacuum degree of $10^{-5}$ Pa order to produce an organic photoluminescent device.

Apart from this, the compound 1 and DPEPO were vapor-deposited on a quartz substrate from different evaporation sources in a vacuum degree of $10^{-5}$ Pa order thereby forming a thin film (doped film) in which the concentration of the compound 1 was 10% by weight, in a thickness of 100 nm to produce an organic photoluminescent device.

Further apart from this, a thin film of the compound 1 was vapor-deposited on a quartz substrate in a thickness of 100 nm in a vacuum degree of $10^{-5}$ Pa order, and in a glove box, the thin film was sealed up with glass and a UV-curable resin to produce a sealed device.

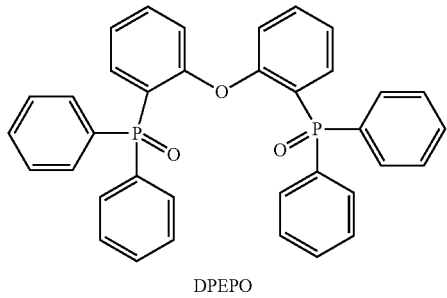 [SMILES: O=P(c1ccccc1)(c1ccccc1)c1ccccc1Oc1ccccc1P(=O)(c1ccccc1)c1ccccc1]

DPEPO

Example 2

In the same manner as in Example 1 except that the compound 2 was used in place of the compound 1, a toluene solution, a single film and a doped film with the compound 2 were formed to produce organic photoluminescent devices.

Example 3

In the same manner as in Example 1 except that the compound 3 was used in place of the compound 1, a toluene solution, a single film and a doped film with the compound 3 were formed to produce organic photoluminescent devices.

Example 4

In the same manner as in Example 1 except that the compound 4 was used in place of the compound 1, a toluene solution, a single film and a doped film with the compound 4 were formed to produce organic photoluminescent devices.

Comparative Examples 1 to 4, and 7 to 9

In the same manner as in Example 1 except that the comparative compounds 1 to 4 and 7 to 9 were used in place of the compound 1, toluene solutions, single films and doped films with the comparative compounds 1 to 4 and 7 to 9 were formed to produce organic photoluminescent devices.

Comparative Examples 5 and 6

In the same manner as in Example 1 except that the comparative compound 5 and 6 were used in place of the compound 1 and acetone was used in place of toluene, acetone solutions, single films and doped films with the comparative compounds 5 and 6 were formed to produce organic photoluminescent devices.

Comparative Examples 10 and 11

In the same manner as in Example 1 except that the comparative compound 10 and 11 were used in place of the compound 1, sealed devices with the comparative compounds 10 and 11 were produced.

The toluene solutions, the acetone solutions, the single films and the doped films produced in Examples and Comparative Examples were analyzed with excitation light (340 nm for the toluene solutions, 360 nm for the acetone solutions, 340 to 360 nm for the single films, 280 nm for the doped films) to measure the emission maximum wavelength and the photoluminescence quantum yield (PL quantum yield) thereof. The measure results are shown in Table 2. Table 2 also shows the full width at half maximum of the emission peak observed with the toluene solutions, the acetone solutions and the doped films produced in Examples and Comparative Examples. Here, for measurement of the photoluminescence quantum yield, the toluene solutions and the acetone solutions were analyzed under two conditions, one with no nitrogen bubbling and the other after nitrogen bubbling, while the single films and the doped films were analyzed in an argon atmosphere. In addition, the toluene solutions, the single films and the doped films with any of the compound 1 and the comparative compound 2 were analyzed for measurement of the instantaneous fluorescence lifetime T1 and the delayed fluorescence lifetime T2 with 340-nm excitation light, and the doped films with any of the compound 1 and the comparative compound 2 were for measurement of the lowest excited singlet energy level $E_{S1}$ and $\Delta E_{ST}$, and all the measurement results are shown in Table 3.

The doped film with the compound 1 was analyzed at a temperature of 5 K, 100 K, 200 K or 300 K for measurement of the transient decay curve of 460-nm emission with 337-nm excitation light, and the measurement results are shown in FIG. 5; the DPEPO films doped with any of the compound 1 and the comparative compound 2 were analyzed for measurement of the photoluminescence quantum yield (PLQY) of instantaneous fluorescence and delayed fluorescence, and the measurement results are shown in FIG. 6; and the DPEPO films doped with any of the compound 2 and the comparative compound 4 were analyzed for measurement of the photoluminescence quantum yield (PLQY) of instantaneous fluorescence and delayed fluorescence, and the measurement results are shown in FIG. 7. In FIGS. 6 and 7, "total" means the total of the photoluminescence quantum yield of instantaneous fluorescence and delayed fluorescence.

The sealed devices with any of the compound 1, and the comparative compounds 10 and 11 were continuously irradiated with 365-nm excitation light in air to measure the time-dependent change of emission intensity thereof, and the measurement results are shown in FIG. 8.

TABLE 2

| | | Solution | | | | Single Film | | Doped Film | | |
|---|---|---|---|---|---|---|---|---|---|---|
| | | Emission | Full Width | PL Quantum Yield | | Emission | PL | Emission | Full Width | PL |
| | | Maximum Wavelength | at Half Maximum | no nitrogen bubbling | nitrogen bubbling | Maximum Wavelength | Quantum Yield | Maximum Wavelength | at Half Maximum | Quantum Yield |
| Example 1 | Compound 1 | 465 nm | 62 nm | 13% | 98% | 503 nm | 71% | 473 nm | 75 nm | 80% |
| Comparative Example 1 | Comparative Compound 1 | 507 nm | 86 nm | 25% | 94% | 553 nm | 50% | 517 nm | 98 nm | 80% |
| Comparative Example 2 | Comparative Compound 2 | 485 nm | 87 nm | 28% | 90% | 515 nm | 21% | 482 nm | 94 nm | 50% |
| Comparative Example 5 | Comparative Compound 5 | 504 nm | 112 nm | 24% | 52% | 496 nm | — | 470 nm | 95 nm | 40% |
| Comparative Example 6 | Comparative Compound 6 | 501 nm | 100 nm | 48% | 60% | 510 nm | — | 475 nm | 91 nm | 40% |
| Example 2 | Compound 2 | 512 nm | 74 nm | 33% | 99% | 516 nm | 63% | 511 nm | 82 nm | 86% |
| Comparative Example 3 | Comparative Compound 3 | 535 nm | 91 nm | 24% | 72% | 587 nm | 8% | 544 nm | 97 nm | 40% |
| Comparative Example 4 | Comparative Compound 4 | 515 nm | 87 nm | 38% | 77% | 546 nm | 30% | 511 nm | 90 nm | 63% |
| Example 7 | Compound 3 | 475 nm | 94 nm | — | 94% | 489 nm | 54% | 486 nm | 92 nm | 72% |
| Comparative Example 7 | Comparative Compound 7 | 520 nm | 128 nm | — | 32% | 518 nm | 23% | 503 nm | 93 nm | 41% |
| Comparative Example 8 | Comparative Compound 8 | 491 nm | 113 nm | — | 72% | 482 nm | 60% | 478 nm | 100 nm | 70% |
| Example 4 | Compound 4 | — | — | — | — | 416 nm | 82% | 408 nm | 84 nm | 99% |
| Comparative Example 9 | Comparative Compound 9 | — | — | — | — | — | — | 456 nm | 91 nm | 99% |

In the Table, "-" means no measurement.

TABLE 3

| | Toluene Solution | | Single Film | | Doped Film | | | |
|---|---|---|---|---|---|---|---|---|
| Compound | Fluorescence Lifetime T1 | Delayed Fluorescence Lifetime T2 | Fluorescence Lifetime T1 | Delayed Fluorescence Lifetime T2 | Fluorescence Lifetime T1 | Delayed Fluorescence Lifetime T2 | $E_{S1}$ | $\Delta E_{ST}$ |
| Compound 1 | 4 ns | 14.2 us | 8.5 ns | 2.9 us | 6.0 ns | 8.5 us | 2.88 eV | 33 meV |
| Comparative Compound 2 | 15 ns | 7.6 us | 10 ns | 1.58 us | 9.6 ns | 4.2 us | 2.88 eV | 41 meV |

As shown in Table 2, the toluene solutions and the acetone solutions of Examples 1 and 2 and Comparative Examples 1 to 6 with nitrogen bubbling all have a higher photoluminescence quantum yield than those with no nitrogen bubbling. This may be considered because, owing to nitrogen bubbling, quenching of triplet excitons by oxygen could be suppressed to promote reverse intersystem crossing from the excited triplet state to the excited singlet state. This indicates that the compounds 1 and 2 and the comparative compounds 1 to 6 all can emit delayed fluorescence via reverse intersystem crossing.

In addition, as in Table 2, the organic photoluminescent devices with any of the compounds 1 and 2 where the carbazol-9-yl group is substituted with a perfluoroalkyl group at the 2-position and the 7-position tended to have, as compared with the organic photoluminescent devices with any of the comparative compounds 1 and 3 where the carbazol-9-yl group is unsubstituted and the comparative compounds 2 and 4 where the carbazol-9-yl group is substituted with a perfluoroalkyl group at the 3-position and the 6-position, a higher photoluminescence quantum yield, a shorter emission wavelength, and a higher color purity (that is, a narrower full width at half maximum in the emission spectrum) in any form of toluene solutions, single films and doped films. Here, the devices with any of the compounds 1 and 2 where the carbazol-9-yl group is substituted with a perfluoroalkyl group at the 2-position and the 7-position have a short emission wavelength and have a narrow full width at half maximum in the spectrum, and the reason may be presumed to be because the vibrational relaxation of the compounds 1 and 2 state may be small after having been in an excited state and therefore the compounds may deactivate from an excited singlet energy level that is higher than the ground level to emit high-energy light (short-wavelength light). Also as in Table 3, the organic photoluminescent device with the compound 1 has a longer delayed fluorescence lifetime T2 than the organic photoluminescent device with the comparative compound 2.

Further as in FIGS. 6 and 7 showing the temperature dependency of the photoluminescence quantum yield of delayed fluorescence, there is seen no difference in the low-temperature region, but in high-temperature region higher than 200 K, there is admitted the temperature dependency of the photoluminescence quantum yield in every case, and obviously, the organic photoluminescent devices with any of the compound 1 and the compound 2 have a higher photoluminescence quantum yield than the organic photoluminescent devices with any of the comparative compound 2 and the comparative compound 4. This indicates that these compounds are all activation-type delayed fluorescent materials and that reverse intersystem crossing to be induced by heat could more readily occur in the compounds 1 and 2 than in the comparative compounds 2 and 4. The tendency of easiness in reverse intersystem crossing is supported by the smaller $\Delta E_{ST}$ of the compound 1 than that of the comparative compound 2 (see Table 1).

On the other hand, in Table 2, the characteristics of the comparative compound 5 where the carbazol-9-yl group is substituted with a cyano group at the 2-position and the 7-position and the comparative compound 6 where the carbazol-9-yl group is substituted with a cyano group at the 3-position and the 6-position are compared with the characteristics in Example 1 (compound 1) and Comparative Example 2 (comparative compound 2), it is known that the emission wavelength is shortened also in the case having a cyano group like in the case having a perfluoroalkyl group, but the photoluminescence quantum yield in the former case is extremely low and the substituent has few influences on the full width at half maximum in the emission spectrum. A perfluoroalkyl group and a cyano group are both electron-attracting substituents having a positive Hammett constant $\sigma_p$, but it is known that in the case having a perfluoroalkyl group, the optical characteristics improve but in the case having a cyano group, the optical characteristics worsen.

From the above-mentioned results, it is known that when a perfluoroalkyl group is introduced into the 2-position and the 7-position of the carbazol-9-yl group of a compound in which the aromatic ring is substituted with a carbazol-9-yl group and an acceptor group, the resultant compound can realize a high emission efficiency and can shorten the emission wavelength. In addition, FIG. 8 confirms that the compound 1 is excellent in lightfastness.

Further, from performance comparison between Examples 3 and 4, and Comparative Examples 7, 8 and 9 in Table 2, the tendency of the emission characteristics to improve is recognized not only in the case where the acceptor unit is a cyanobenzene but also in the case where the acceptor unit is a structure having a perfluoroalkyl group-substituted aromatic ring or a hetero ring such as a triazine.

[Production of Organic Electroluminescent Device and Evaluation of Emission Characteristics Thereof]

Example 5

On a glass substrate having, as formed thereon, an anode of indium tin oxide (ITO) having a thickness of 100 nm, thin films were layered through vapor deposition in a vacuum degree of $10^{-5}$ Pa order. First, on ITO, NPD was formed in a thickness of 30 nm, and on this, mCP was formed in a thickness of 10 mm. Next, the compound 1 and PPT were co-deposited from different evaporation sources to form a layer having a thickness of 20 nm to be a light emitting layer. At this time, the concentration of the compound 1 was 5% by weight. Next, PPT was formed in a thickness of 40 nm, and on this, lithium fluoride (LiF) was vacuum-deposited in 0.8 nm, and then aluminum (Al) was deposited thereon in a thickness of 100 nm to form a cathode. According to the process, an organic electroluminescent device was produced using the compound 1.

FIG. 9 shows the current density-voltage-luminance characteristic of the thus-produced organic electroluminescent device. The organic electroluminescent device has an emission maximum wavelength at 460 nm, as shown in FIG. 10, and the chromaticity coordinate thereof (x, y) is (0.15, 0.15). The organic electroluminescent device attained an external quantum efficiency of more than 14%, and was confirmed to be an excellent device.

Comparative Example 12

An organic electroluminescent device was produced in the same manner as in Example 5 except that the comparative compound 2 was used in place of the compound 1.

The current density-voltage-luminance characteristic of the thus-produced organic electroluminescent device is shown in FIG. 9. As shown in FIG. 10, the emission maximum wavelength of the organic electroluminescent device is 470 nm, and the chromaticity coordinate thereof (x, y) is (0.15, 0.23). As compared with that of the organic electroluminescent device of Example 3, the emission wavelength of this device was long. In addition, the maximum external quantum efficiency of this device was less than 10%, and was significantly lower than that of the organic electroluminescent device of Example 3.

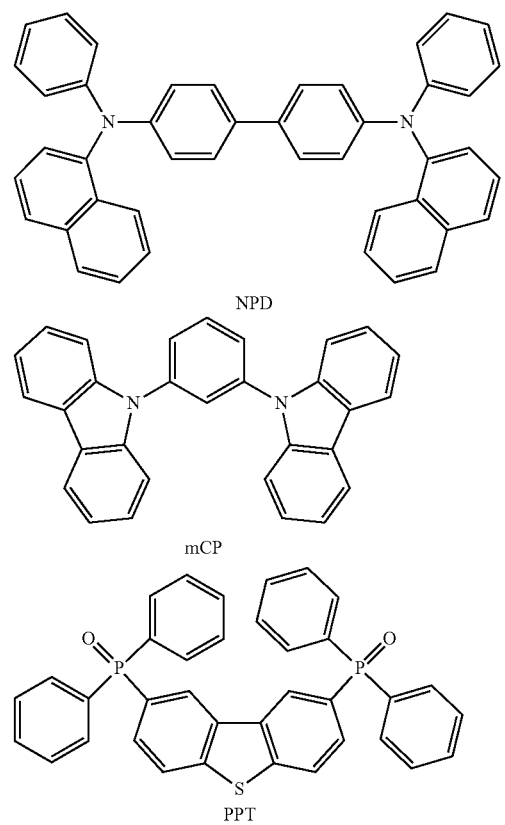

INDUSTRIAL APPLICABILITY

Of the compound of the present invention, the HOMO level and the LUMO level are both deep, and the compound has excellent emission characteristic and high lightfastness. Consequently, the compound of the present invention is useful as a light emitting material for organic light emitting devices. In addition, the organic light emitting device of the present invention contains the compound of the type, and therefore can realize excellent emission characteristics. Accordingly, the industrial applicability of the present invention is great.

REFERENCE SIGNS LIST

1 Substrate
2 Anode
3 Hole Injection Layer
4 Hole Transport Layer
5 Light Emitting Layer
6 Electron Transport Layer
7 Cathode

The invention claimed is:

1. A compound represented by the following formula (2):

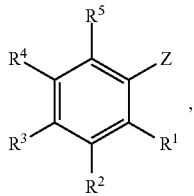

Formula (2)

wherein Z represents a cyano group, a perfluoroalkyl group, a substituted or unsubstituted triazinyl group, or a substituted or unsubstituted pyrimidinyl group, at least one of $R^1$, $R^2$, $R^3$, $R^4$ and $R^5$ represents a carbazol-9-yl group substituted with a perfluoroalkyl group at the 2-position and the 7-position, and the remaining $R^1$, $R^2$, $R^3$, $R^4$ and $R^5$ each independently represent a hydrogen atom or a substituent, provided that when one of $R^1$, $R^2$, $R^3$, $R^4$ and $R^5$ is a cyano group, a perfluoroalkyl group, a substituted or unsubstituted triazinyl group, or a substituted or unsubstituted pyrimidinyl group, then the group is identical to Z, provided that at least one of the following conditions is satisfied:
<1> at least three of $R^1$, $R^2$, $R^3$, $R^4$ and $R^5$ is a carbazol-9-yl group substituted with a perfluoroalkyl group at the 2-position and the 7-position,
<2> $R^2$ is a cyano group or a perfluoromethyl group,
<3> $R^3$ is a cyano group or a perfluoromethyl group, and
<4> at least one of $R^1$, $R^2$, $R^3$, $R^4$ and $R^5$ is a carbazol-9-yl group substituted with a perfluoroalkyl group at the 2-position and the 7-position and substituted with a carbazolyl group at at least one of the 1-position, 3-position, 4-position, 5-position, 6-position and 8-position.

2. The compound according to claim 1, wherein $R^2$ in the formula (2) is a cyano group or a perfluoromethyl group.

3. The compound according to claim 2, wherein $R^1$, $R^3$, $R^4$ and $R^5$ each represent a carbazol-9-yl group substituted with a perfluoroalkyl group at the 2-position and the 7-position.

4. The compound according to claim 1, wherein $R^3$ in the formula (2) is a cyano group or a perfluoromethyl group.

5. The compound according to claim 4, wherein $R^1$, $R^2$, $R^4$ and $R^5$ in the formula (2) each are a carbazol-9-yl group substituted with a perfluoroalkyl group at the 2-position and the 7-position.

6. The compound according to claim 1, wherein the carbazol-9-yl group substituted with a perfluoroalkyl group at the 2-position and the 7-position has a structure represented by the following formula (11):

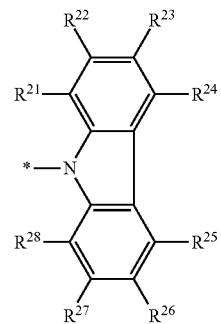

Formula (11)

wherein * represents a bonding site to the benzene ring of the formula (2), $R^{21}$, $R^{23}$, $R^{24}$, $R^{25}$, $R^{26}$ and $R^{28}$ each independently represent a hydrogen atom or a substituent, and $R^{22}$ and $R^{27}$ each represent a perfluoroalkyl group.

7. The compound according to claim 6, wherein at least one of $R^{21}$, $R^{23}$, $R^{24}$, $R^{25}$, $R^{26}$ and $R^{28}$ in the formula (11) is a substituted or unsubstituted carbazolyl group.

8. The compound according to claim 7, wherein $R^{23}$ in the formula (11) is a substituted or unsubstituted carbazolyl group.

9. The compound according to claim 7, wherein $R^{23}$ and $R^{26}$ in the formula (11) each are a substituted or unsubstituted carbazolyl group.

10. The compound according to claim 7, wherein the carbazolyl group is substituted with a cyano group.

11. An organic light emitting device comprising the compound according to claim 1.

12. An organic light emitting device comprising a light emitting layer comprising the compound according to claim 1 on a substrate.

13. The organic light emitting device according to claim 11, which emits delayed fluorescence.

14. The organic light emitting device according to claim 11, which is an organic electroluminescent device.

* * * * *